United States Patent [19]

Fujimoto et al.

[11] 4,058,622
[45] Nov. 15, 1977

[54] SUBSTITUTED PHENYL ACETATE, INSECTICIDAL COMPOSITION AND METHOD OF USE

[75] Inventors: Keimei Fujimoto, Kobe; Nobuo Ohno, Toyonaka; Yoshitoshi Okuno, Toyonaka; Toshio Mizutani, Toyonaka; Isao Ohno, Minoo; Masachika Hirano, Toyonaka; Nobushige Itaya, Ikeda; Takashi Matsuo, Amagasaki, all of Japan

[73] Assignee: Sumitomo Chemical Company, Limited, Osaka, Japan

[21] Appl. No.: 557,694

[22] Filed: Mar. 12, 1975

Related U.S. Application Data

[63] Continuation-in-part of Ser. No. 378,301, July 11, 1973, Pat. No. 3,996,244.

[30] Foreign Application Priority Data

July 11, 1972 Japan .................................. 47-69805
Apr. 19, 1973 Japan .................................. 48-44809

[51] Int. Cl.² ........................ A01N 9/24; C07C 69/76

[52] U.S. Cl. ........................................ 424/308; 560/81; 560/122; 560/128; 560/125; 560/221; 560/105; 560/104; 560/55; 560/51; 560/8; 560/100; 560/9; 260/326 A; 260/326 S; 260/326.42; 260/347.4; 260/464; 260/465 D; 260/465.4; 424/274; 424/304; 424/305; 424/309; 424/314

[58] Field of Search ................. 260/476 R; 424/308

[56] References Cited

U.S. PATENT DOCUMENTS

3,968,124  7/1976  Mizutani et al. ................. 260/476 R

FOREIGN PATENT DOCUMENTS

2,335,347  2/1974  Germany .......................... 260/476

*Primary Examiner*—Jane S. Myers
*Attorney, Agent, or Firm*—Sughrue, Rothwell, Mion, Zinn and Macpeak

[57] ABSTRACT

Substituted acetate compounds represented by the formula

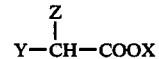

which are useful as pesticides and pesticidal compositions containing the substituted acetate compounds as active ingredients, as well as processes for preparing the compounds and the compositions are disclosed.

5 Claims, No Drawings

SUBSTITUTED PHENYL ACETATE, INSECTICIDAL COMPOSITION AND METHOD OF USE

CROSS-REFERENCE TO RELATED APPLICATIONS

This is a continuation-in-part application of copending application, Ser. No. 378,301, filed July 11, 1973 now U.S. Pat. No. 3,996,244.

BACKGROUND OF THE INVENTION

1. Field of the Invention

This invention relates to a pesticide, and more particularly, this invention relates to substituted acetate compounds of the formula (I) hereinafter described useful for controlling arthropods, pesticidal compositions containing as active ingredients at least one substituted acetate compound of the formula (I), as well as processes for preparing the substituted acetate compounds and the pesticidal compositions.

2. Description of the Prior Art

Since BHC and DDT have been developed, remarkable advances have been made in organic agricultural agents such as phosphorus agents, carbamates, pyrethroids and the progress of such organic agricultural agents now establishes a certain close correlation between the consumed quantity of pesticides and the harvested quantity of crops. However, on the other hand, these agricultural agents have caused pollution due to environmental contamination and at present there are many problems such as the accumulation of toxicity and the chronic toxicity as well as the generation of a wide variety of pesticide-resistant noxious insects. The desirable requirements for pesticides are, therefore, that the active pesticides exhibit a low toxicity, a low residual and a rapid decomposition and they are converted into non-toxic materials upon entrance into one of the biological cycles of the ecological system. In particular, compounds containing no heavy metals nor halogen atoms and composed mainly of carbon, hydrogen and oxygen are considered to be advantageous as agricultural agents.

The active groups of the pesticides presently used include organic phosphorus compounds, carbamates, chrysanthemic acid esters, organochloric compounds, etc., and most of the researchers in this field now endeavour to develop new types of pesticides by considering the superiority or inferiority of each of the above active groups and screening various synthetic derivatives retaining only the superiority of the known pesticides.

The present inventors considered that each of the above well-known active groups has certain properties as basic pesticidal characteristics inherent to the specific active group and that the disadvantages associated with the specific active group would not be eliminated unless departing from the above specific properties. As a result of extensive research for active groups having novel chemical structures, the present inventors found the new and useful acetic acid esters represented by the formula (I) described below.

SUMMARY OF THE INVENTION

The substituted acetate compounds of this invention are represented by the formula:

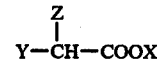

wherein Y represents a substituted aromatic group or an usaturated alicyclic group having an appropriate plane and is selected from the group consisting of the formulae

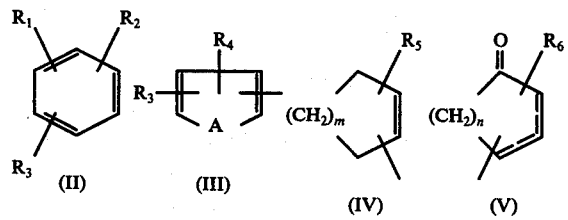

in which $R_1$ and $R_2$ are individually hydrogen, halogen, cyano, nitro, lower alkyl, lower alkenyl, lower alkynyl, lower alkoxy, lower alkoxyalkyl, halogen-substituted lower alkyl, halogen-substituted lower alkenyl, halogen-substituted kower alkynyl, lower alkylthio, lower alkysulfoxyl, acyl, acyloxy, lower alkoxycarbonyl, lower alkenyloxycarbonyl, or lower alkynyloxycarbonyl group or can combine to form a methylenedioxy, tetramethylene or trimethylene group; $R_3$ and $R_4$ are individually hydrogen, halogen, cyano, nitro, lower alkyl, lower alkenyl, lower alkynyl, lower alkoxy, lower alkoxyalkyl, halogen-substituted lower alkyl, halogen-substituted lower alkenyl, halogen-substituted lower alkynyl, lower alkylthio, lower alkylsulfoxyl, acyl, acyloxy, lower alkoxycarbonyl, lower alkenyloxycarbonyl or lower alkynyloxycarbonyl group; A represents an oxygen atom or a sulfur atom; $R_5$ represents hydrogen, halogen, cyano, nitro or lower alkyl group; $m$ is an integer of from 1 to 3; $R_6$ represents hydrogen, halogen, cyano, nitro or lower alkyl group; $n$ is an integer of from 1 to 3; and the dotted line in the formula (V) represents a double bond present at a position conjugated or non-conjugated with the ketone (C=O), or Y represents a substituted ethylene group of the formula (VI)

in which $R_7$, $R_8$ and $R_9$ constitute a plane together with the double bond at the $\beta$-$\gamma$ position of the ester group, and are individually hydrogen, lower alkyl, lower alkenyl, lower alkynyl, halogen, acyl or acyloxy; Z represents a straight or branched lower alkyl, lower alkenyl, lower alkynyl, lower alkoxy, cyano, halogen-substituted lower alkyl, halogen-substituted lower alkenyl group or an alicyclic group having 3 to 7 carbon atoms; X represents a group corresponding to an alcohol moiety of the ester-type insecticides which are known as pyrethroid insecticides, and is selected from the group consisting of the formulae

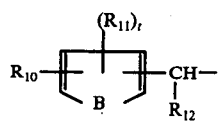  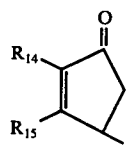 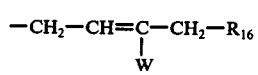

(VII)　　　(VIII)　　(IX)　　　(X)

in which $R_{10}$ represents an allyl, propargyl, benzyl, thenyl, furylmethyl, phenoxy or phenylthio group; $R_{11}$ represents hydrogen, methyl, trifluoromethyl or halogen, $R_{10}$ and $R_{11}$ may, when they are bonded to each other at terminals, form a trimethylene or tetramethylene group; $R_{12}$ represents hydrogen, ethynyl or cyano; $t$ is an integer of from 1 to 2; B represents an oxygen or sulfur atom or a —CH=CH— group; $R_{13}$ represents phthalimide, thiophthalimide, di- or tetrahydrophthalimide or dialkylmaleimide; $R_{14}$ represents allyl, propargyl, benzyl or alkadienyl; $R_{15}$ represents hydrogen or methyl; $R_{16}$ represents phenyl, thienyl or furyl; and W represents methyl or halogen. Preferred compounds within the formula (I) are as follows:

1. compounds of the formula;

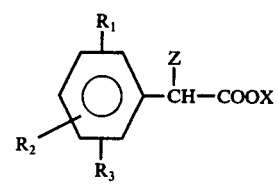

wherein $R_1$ is a member selected from the group consisting of hydrogen, methoxy, ethoxy, acetoxy, methylsulfinyl, $C_1$-$C_4$ alkyl, trifluoromethyl, allyl, acetyl, ethoxycarbonyl, methylenedioxy, methylthio, trimethylene, tetramethylene, chlorine, fluorine, iodine, isopropenyl, propargyl, methoxymethyl, ethoxymethyl, chloroethylene, chloroallyl, butyryl, butylthio, allyloxycarbonyl, nitro and methoxycarbonyl; $R_2$ is a member selected from the group consisting of hydrogen, methyl, methoxy, chlorine and bromine; $R_3$ is hydrogen or methyl; Z is a member selected from the group consisting of $C_1$-$C_4$ alkyl, ethoxy, allyl, bromoethyl, cyclohexyl, cyclopropylmethyl, isopropenyl, propargyl, trifluoromethyl and cyano; and X is a member selected from the group consisting of:

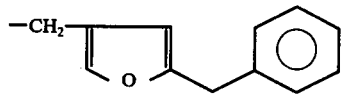 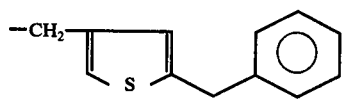

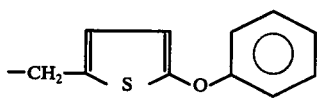 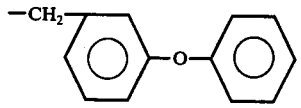

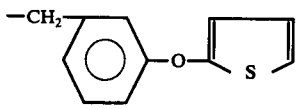 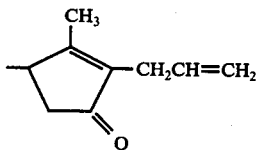

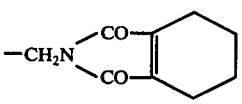 

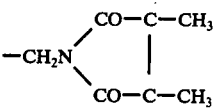 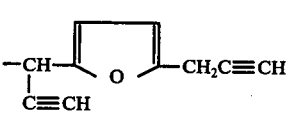

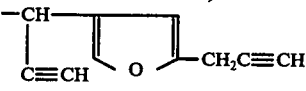 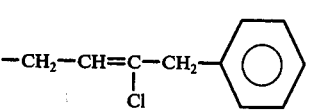

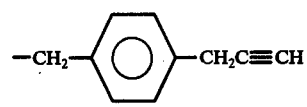,
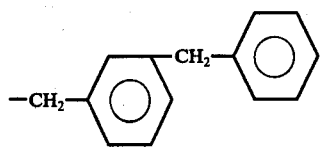,
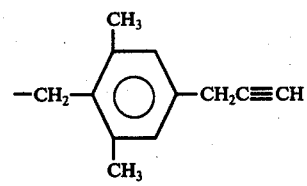,
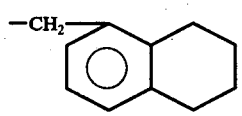,
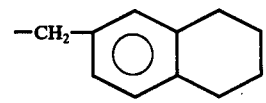,
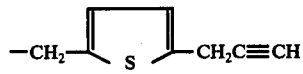,
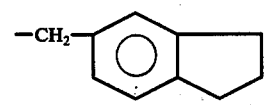,
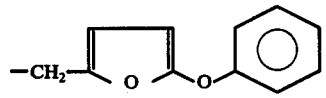,
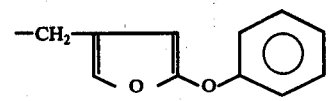,
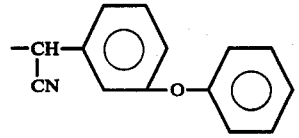,
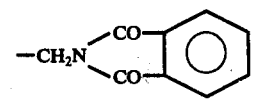,
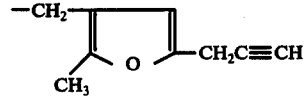,
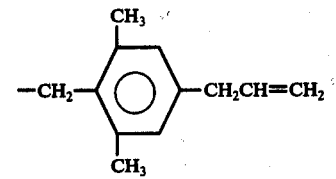,
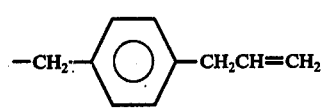,
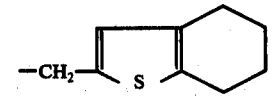,
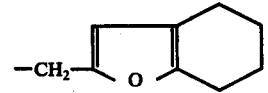,
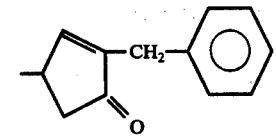,
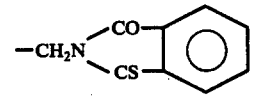,
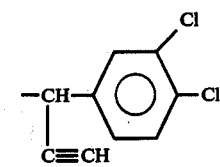,
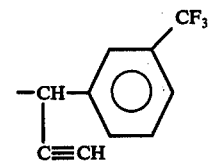,
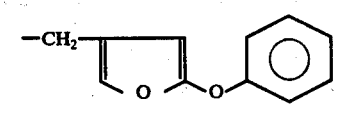,
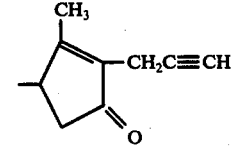,

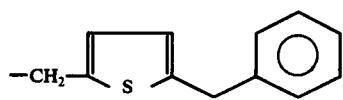 , 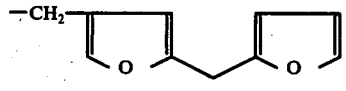 ,

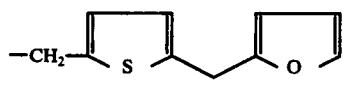 , 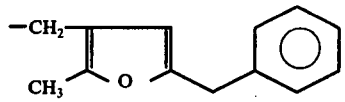

and

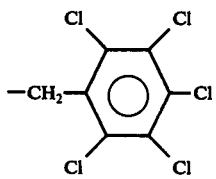

2. compounds of the formula;

wherein $R_3$ is a member selected from the group consisting of hydrogen, methyl, allyl, methoxycarbonyl and acetyl; $R_4$ is hydrogen; Z is a member selected from the group consisting of ethyl, propyl and allyl; and X is a member selected from the group consisting of

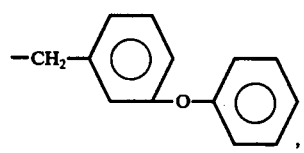 ,

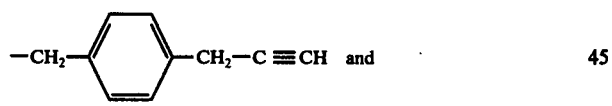 ,

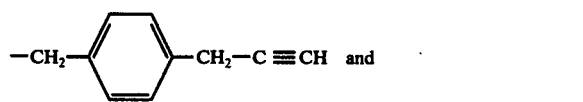 and

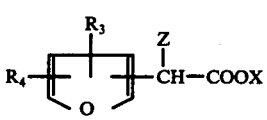 .

3. compounds of the formula;

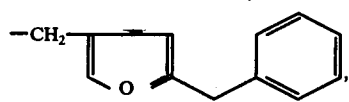

wherein $R_3$ is a member selected from the group consisting of hydrogen, methyl, allyl, methoxycarbonyl and butyryl; $R_4$ is hydrogen; Z is ethyl or propyl; X is a member selected from the group consisting of

 ,

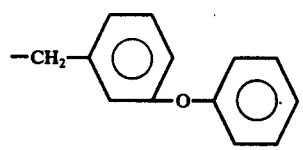 and

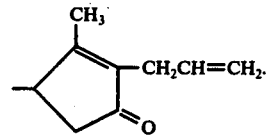

4. compounds of the formula;

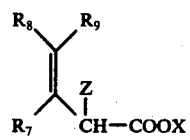

wherein $R_7$ is a member selected from the group consisting of hydrogen, methyl and ethyl; $R_8$ is hydrogen or methyl; $R_9$ is methyl; Z is $C_1$-$C_3$ alkyl; and X is a member selected from the group consisting of

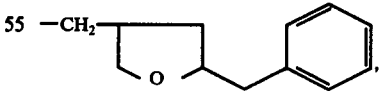 ,

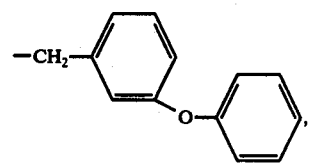 ,

 and

-continued

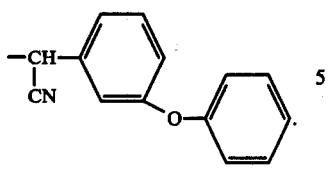

5. compounds of the formula;

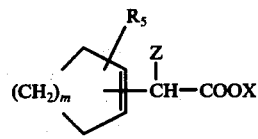

wherein $R_5$ is hydrogen or methyl; $m$ is an integer of 1 or 2; Z is a member selected from the group consisting of methyl, propyl, allyl and propargyl; X is a member selected from the group consisting of

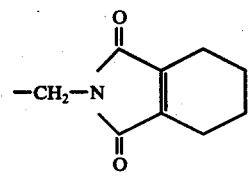

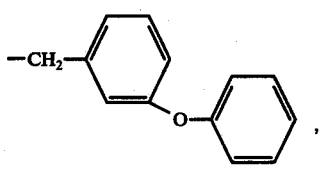

and

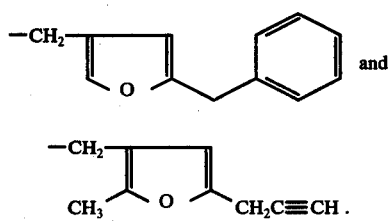

6. compounds of the formula;

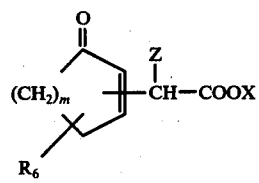

wherein $R_6$ is methyl, $n$ is an integer of 1, Z is ethyl or propyl; X is a member selected from the group consisting of

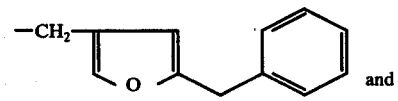 and

-continued

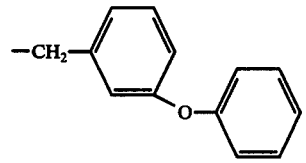

7. Compounds of the formula

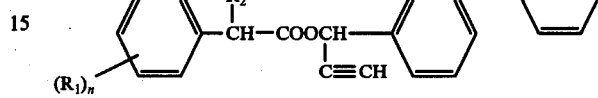

wherein $R_1$, which may be the same or different, is halogen, $C_1$-$C_4$ alkyl, $C_1$-$C_4$ alkoxyl, methylenedioxy; $n$ is 1 or 2; $R_2$ is $C_1$-$C_4$ alkyl; and A is oxygen or —$CH_2$—.

Among the present compounds, the phenylacetic acid esters, prepared by reacting phenylacetic acid derivatives of the formula;

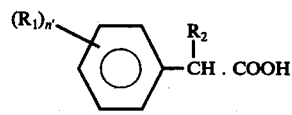

wherein $R_1$ represents a straight or branched chain alkyl group having 1 to 5 carbon atoms, a straight or branched chain alkoxy group having 1 to 5 carbon atoms, a halogen atom or a thiomethyl group and two of $R_1$ may form a trimethylene —$(CH_2)_3$— or tetramethylene —$(CH_2)_4$— or a methylenedioxy —O—$CH_2$—O— group; $n'$ is an integer of from 1 to 4; and $R_2$ represents a straight or branched chain alkyl group having 3 to 5 carbon atoms, an allyl group, a propargyl group or an isopropenyl group; with a pyrethroid alcohol, have prominent effects to injurious insects and low toxicity to mammals. And, therefore, the above mentioned phenylacetic acids are important as intermediates of the present invention.

The compounds of this invention have various advantages broadly and also exhibit strong selectivity, and the chemical structure retaining only properties advantageous as agricultural agents can be considered depending upon the specific type of the compounds of this invention.

Hithertofore, esters which are considered to be pesticidal active groups, for example, phosphoric acid esters and chrysanthemic acid esters are believed to have their activities in the basic structures of phosphoric acid and cyclopropanecarboxylic acid, respectively. These esters contain a S (or O) atom bonded to a pentavalent phosphorus by a double bond as an essential structure of the phosphoric acid esters and a three-membered ring as an essential structure of the chrysanthemic acid esters, respectively, and the pesticidal activity tends to be strengthened or weakened depending upon the type of moieties present around the above essential structure as a nucleus.

In the compounds of this invention, the acid moiety represented by the formula (XI)

$$\overset{Z}{\underset{|}{Y-CH.COOH}} \quad (XI)$$

is considered to be an important active basic structure, and its essential structure is completed by a hydrogen atom at α-position of the ester group, an appropriate substituent (Z) and a substituent (Y) which are characterized in its plane structure. On the other hand, the alcohol moiety of the ester corresponds to the alcohol moiety of the well-known chrysanthemic acid esters as shown by the examples of compounds described below, but, in accordance with the present invention, it was found that highly active pesticides can be prepared by esterification of the acids represented by the formula (XI) with the above alcohol moiety and that the compounds having a surprisingly high selectivity can be prepared by using an appropriate combination of an acid moiety and an alcohol moiety. However, the order of activity of the ester composed of the known alcohol and the known acid cannot be applied as it is to the evaluation of the activity of the esters in accordance with the present invention since the esters of this invention exhibit activities entirely different from those of the known esters. Accordingly, the esters composed of the acid used in the present invention and the alcohol which has been found to form a highly active ester in the known pesticides do not necessarily exhibit an excellent activity.

In addition, in accordance with the present invention, various advantages such as immediate onset of action, permeability, transfer into living plants, residual activity, pesticidal activity, metamorphosis disturbance, sterilization, prohibition of egg-laying can freely be controlled by appropriately selecting a combination of an acid of the present invention and a wide variety of alcohols. Also, with respect to the spectrum of pesticidal activity, the compounds of this invention exhibit a selective or non-selective activity on injurious insects, ticks and mites, such orders as Coreoptera, Lepidoptera, Diptera, Orthoptera, Hemiptera and Acarina depending upon the specific combination of acid and alcohol according to the present invention. Furthermore, the compounds of the present invention are expected to be useful for controlling noxious insects such as nematoda. Other important features of the compounds of this invention are that they are active against noxious insects which are resistant to the pesticides presently used because their basic structures differ from these of the known pesticides to which the insects are resistant, and that they are totally low toxic to mammals including man as indicated by the Experiments shown below.

As the result of the present invention, the substituted acetate compounds of the formula,

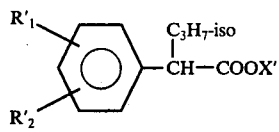

wherein $R'_1$ represents straight or branched chain alkyl having 1 to 4 carbon atoms, halogen or alkoxy having 1 to 4 carbon atoms; $R'_2$ represents hydrogen or a group which completes, together with $R'_1$, methylenedioxy; and X' represents a group of the formula,

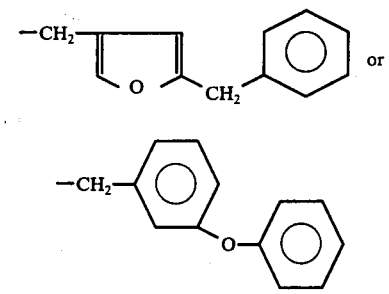

are more excellent in insecticidal effect, killing effect and knock down effect than the other substituted acetate compounds of the formula (I).

In order to make the above fact clearer, the superiority of the compounds represented by the formula (I') in biological effects is shown below with reference to Experimental Examples. But the other compounds of the formula (I) and their geometrical isomers and optical isomers display superior effects to the known insecticidal agents.

In preparing the substituted acetic acid esters represented by the formula (I), an acid represented by the formula $$\overset{Z}{\underset{|}{Y-CH-COOH}} \quad (XI)$$

wherein Y and Z are as defined above, or a reactive derivative thereof is reacted with an alcohol represented by the formula $$X - OH \quad (XII)$$

wherein X is as defined above, or a halide or sulfoxylate thereof.

The term "reactive derivative" of the acid used herein refers to an acid halide, an acid anhydride, an ester with an alcohol having a low boiling point, and an alkali metal salt, a silver salt or an organic tertiary base salt of the acid.

The substituted acetic acid ester represented by the formula (I) include optical isomers due to the carbon atom at α-position, and it is to be understood that the present invention contemplates including such optical isomers.

In carrying out the production of the substituted acetic acid esters of the formula (I), the esterification between the acid (XI) and the alcohol (XII) can advantageously be accomplished by reacting the reactants in an appropriate inert solvent at room temperature or an elevated temperature under an appropriate dehydrating condition, e.g., in the presence of cyclohexylcarbodiimide. When an acid halide is used as a reactive derivative of the acid (XI), the desired ester can be obtained in high yield by reacting the alcohol (XII) and the acid halide at room temperature using an acid acceptor, for example, an organic tertiary amine such as pyridine, triethylamine and the like. The acid halides which can be used in the process of this invention may be any type of halide within the scope of this invention, but an acid chloride is generally preferred. The presence of an inert solvent is not essential in the esterification reaction, but it is generally preferred to use a solvent in order to assure a smooth reaction. Any solvent which is inert to the reactants and the ester product may be used and a preferred inert solvent includes benzene, toluene and petroleum benzine. When an ester of the acid (XI) and a low boiling point alcohol, e.g., methanol, ethanol and the like is used as a reactive derivative of the acid, the desired ester (I) can be obtained in high yield by heat-reacting the ester and the alcohol (XII) with heating in the presence of an appropriate organic base catalyst, preferably, an alkali metal alkoxide corresponding to the low boiling alcohol of the ester used or sodium hydride in an inert solvent such as toluene while removing a low boiling alcohol liberated during the reaction from the reaction system by a fractional distillation column.

In an alternative esterification precedure using an acid anhydride as a reactive derivative of the acid (XI), the desired ester can be obtained by reacting the acid anhydride with the alcohol (XII) at room temperature without using specific reaction aids. In this case, it is preferred to heat the reaction system and to use a solvent such as toluene, xylene and the like in order to ensure a smooth reaction, but the heating and the use of solvent are not critical in this procedure.

When a halide or sulfoxylate of the above alcohol (XII) is used, the acid (XI) is generally employed in the form of an alkali metal salt, a silver salt or an organic tertiary base salt. These salts may be formed in situ by adding simultaneously the acid (XII) and the corresponding base to the reaction system. In this case, a solvent such as benzene, acetone, dimethylformamide and the like is preferably used, and the reaction is preferably conducted by heating the reaction system at or below the boiling point of the solvent used. A preferred halogen for the halide of alcohol (XII) includes chlorine and bromine.

Representative examples of the compounds of this invention are illustrated below, but the present invention is not limited thereto.

| Compound No. | |
|---|---|
| 1. | 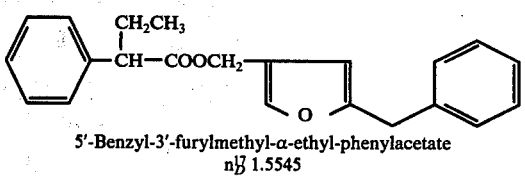<br>5'-Benzyl-3'-furylmethyl-α-ethyl-phenylacetate<br>$n_D^{27}$ 1.5545 |
| 2. | 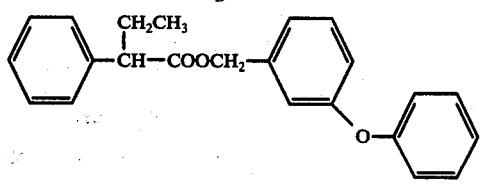<br>3'-Phenoxybenzyl-α-ethylphenylacetate<br>$n_D^{27}$ 1.5712 |
| 3. | 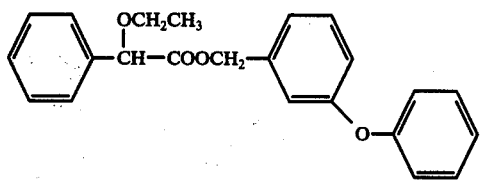<br>3'-Phenoxybenzyl-α-ethoxyphenylacetate<br>$n_D^{24}$ 1.5275 |
| 4. | 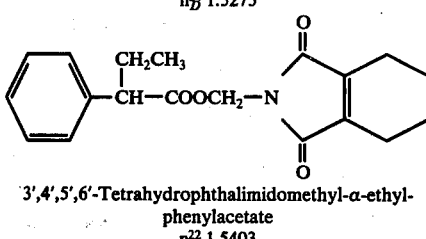<br>3',4',5',6'-Tetrahydrophthalimidomethyl-α-ethyl-phenylacetate<br>$n_D^{27}$ 1.5403 |
| 5. | 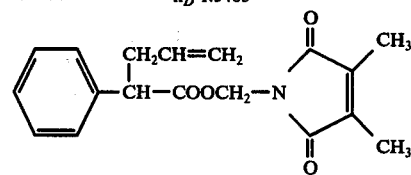<br>Dimethylmaleimidomethyl-α-allylphenylacetate<br>$n_D^{27}$ 1.5349 |
| 6. | 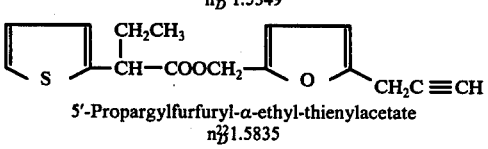<br>5'-Propargylfurfuryl-α-ethyl-thienylacetate<br>$n_D^{21}$ 1.5835 |

| Compound No. | |
|---|---|
| 7. | 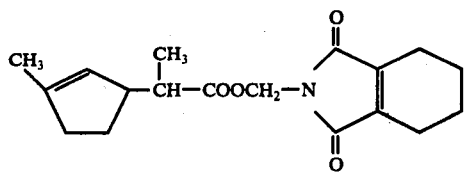<br>3',4',5',6'-Tetrahydrophthalimidomethyl-2-(3''-methyl-2''-cyclopentene-1'''-yl)-propionate<br>$n_D^{22}$ 1.5648 |
| 8. | 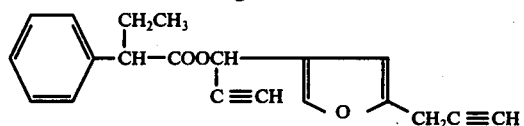<br>5'-Propargyl-α'-ethynyl-3'-furylmethyl-α-ethyl-phenylacetate<br>$n_D^{24.5}$ 1.5310 |
| 9. | 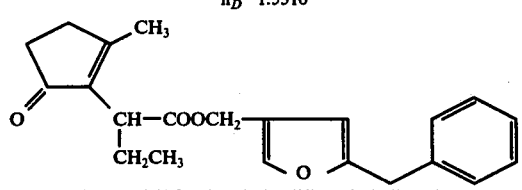<br>5'-Benzyl-3'-furylmethyl-2-(3''-methyl-2''-cyclopentenone-2''-yl)-butyrate<br>$n_D^{22}$ 1.5123 |
| 10. | 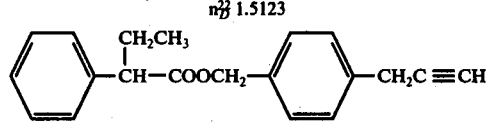<br>4'-Propargylbenzyl-α-ethylphenylacetate<br>$n_D^{23}$ 1.5039 |
| 11. | 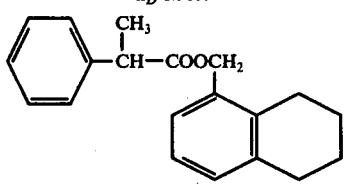<br>5'-(1',2',3',4'-Tetrahydronaphthalenyl)-methyl-α-methylphenlacetate<br>$n_D^{24}$ 1.5536 |
| 12. | 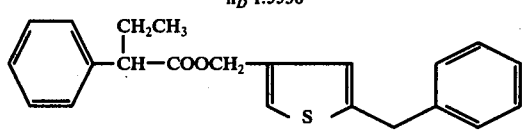<br>5'-Benzyl-3'-thenyl-α-ethylphenylacetate<br>$n_D^{22}$ 1.5488 |
| 13. | 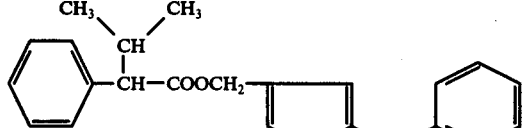<br>5'-Benzyl-3'-thenyl-α-isopropyl-phenylacetate<br>$n_D^{22}$ 1.5613 |
| 14. | 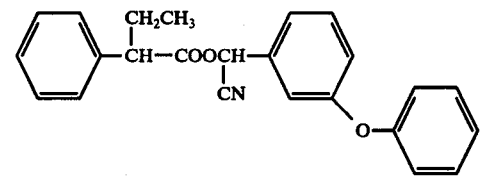<br>3'-Phenoxy-α'-cyanobenzyl-α-ethylphenylacetate<br>$n_D^{22}$ 1.5638 |
| 15. | 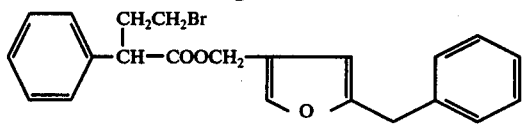 |

| Compound No. | |
|---|---|
| | 5'-Benzyl-3'-furylmethyl-α-(2''-bromoethyl)-phenylacetate<br>$n_D^{23}$ 1.5911 |
| 16. | 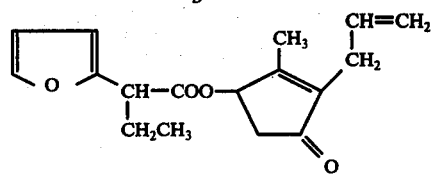<br>2'-Allyl-3'-methyl-2'-cyclopentene-1'-one-4''-yl-α-ethyl-2-furylacetate<br>$n_D^{22}$ 1.5118 |
| 17. | 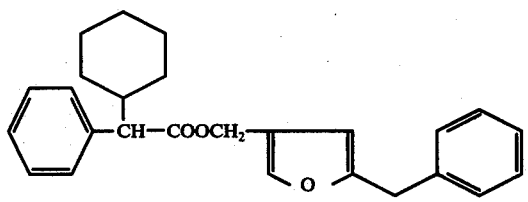<br>5-Benzyl-3'-furylmethyl-α-cyclohexyl-phenylacetate<br>m.p. 51 – 53° C |
| 18. | 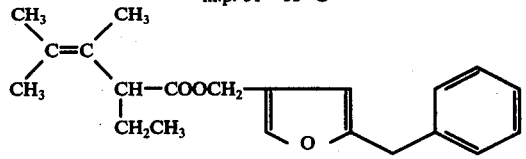<br>5'-Benzyl-3'-furylmethyl-2-ethyl-3,4-dimethyl-3-pentenoate<br>$n_D^{23}$ 1.5417 |
| 19. | 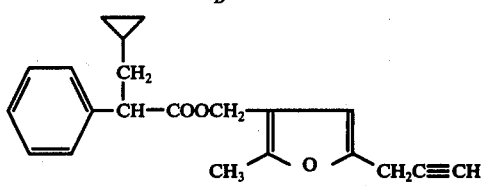<br>5'-Propargyl-2'-methyl-3'-furylmethyl-α-cyclopropylmethylphenylacetate<br>$n_D^{24}$ 1.5632 |
| 20. | 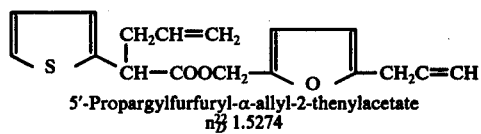<br>5'-Propargylfurfuryl-α-allyl-2-thenylacetate<br>$n_D^{23}$ 1.5274 |
| 21. | 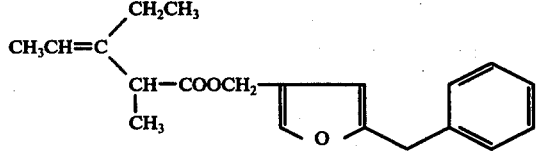<br>5'-Benzyl-3'-furylmethyl-2-methyl-3-ethyl-3-(cis,trans)-pentenoate<br>$n_D^{21}$ 1.5693 |
| 22. | 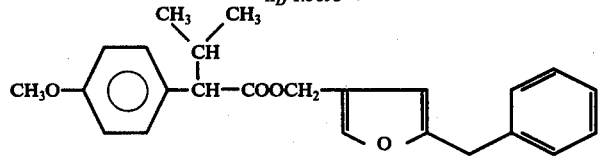<br>5'-Benzyl-3'-furylmethyl-α-isopropyl-4-methoxyphenylacetate<br>$n_D^{17}$ 1.5470 |
| 23. | 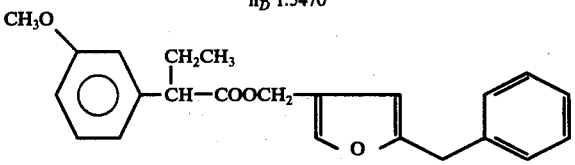<br>5'-Benzyl-3'-furylmethyl-α-ethyl-3-methoxyphenyl-acetate |

| Compound No. | |
|---|---|
| 24. | 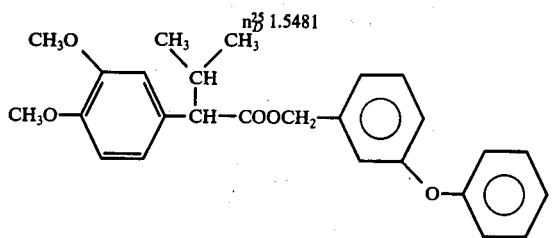
3'-Phenoxybenzyl-α-isopropyl-3,4-dimethoxyphenyl-
acetate
$n_D^{25}$ 1.5655 |
| 25. | 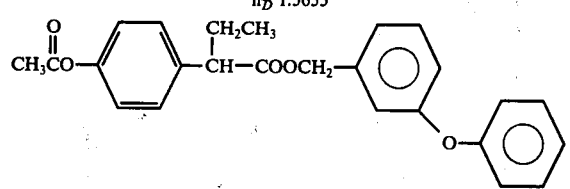
3'-Phenoxybenzyl-α-ethyl-4-acetoxyphenylacetate
$n_D^{25}$ 1.5621 |
| 26. | 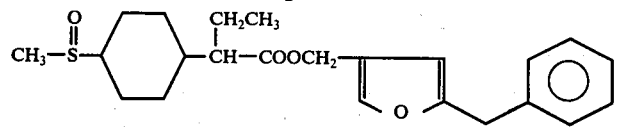
5'-Benzyl-3'-furylmethyl-α-ethyl-4-methylsulfoxy-
phenylacetate
$n_D^{25}$ 1.5448 |
| 27. | 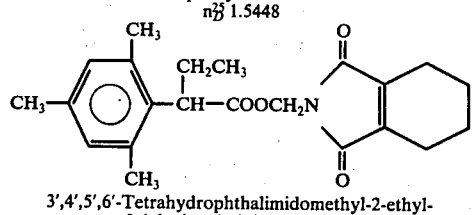
3',4',5',6'-Tetrahydrophthalimidomethyl-2-ethyl-
2,4,6-trimethylphenylacetate
$n_D^{25}$ 1.5399 |
| 28. | 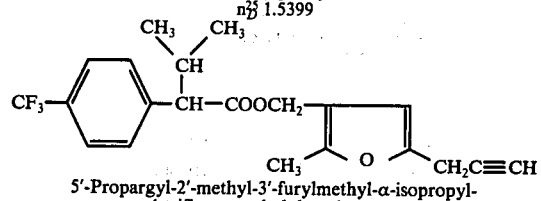
5'-Propargyl-2'-methyl-3'-furylmethyl-α-isopropyl-
4-trifluoromethylphenylacetate
$n_D^{25}$ 1.5368 |
| 29. | 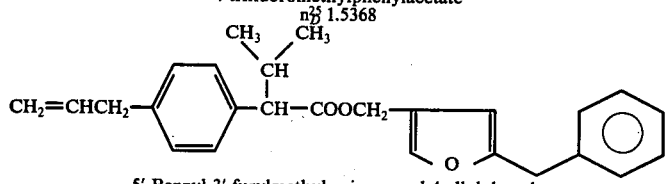
5'-Benzyl-3'-furylmethyl-α-isopropyl-4-allylphenyl-
acetate
$n_D^{25}$ 1.5277 |
| 30. | 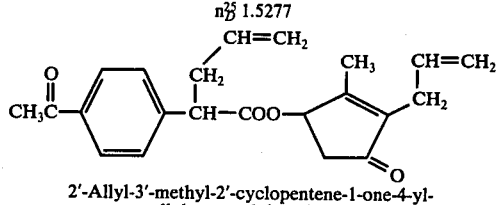
2'-Allyl-3'-methyl-2'-cyclopentene-1-one-4-yl-
α-allyl-p-acetylphenylacetate
$n_D^{25}$ 1.5566 |
| 31. | 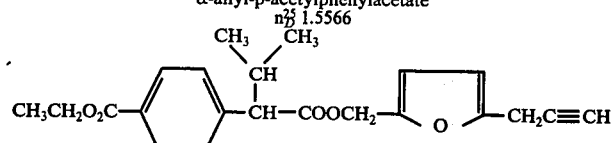
5'-Propargylfurfuryl-α-isopropyl-4-carbethoxy-
phenylacetate |

| Compound No. | |
|---|---|
| 32. | 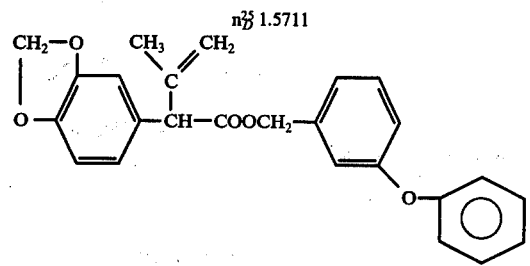<br>3'-Phenoxybenzyl-α-isopropenyl-3,4-methylenedioxyphenylacetate<br>$n_D^{25}$ 1.5325 |
| 33. | 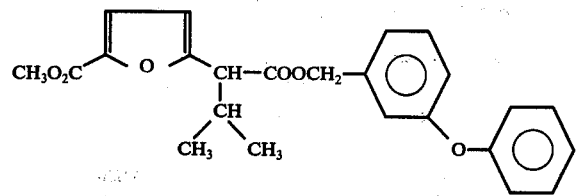<br>3'-Phenoxybenzyl-α-isopropyl-5-carbomethoxy-2-furylacetate<br>$n_D^{25}$ 1.5367 |
| 34. | 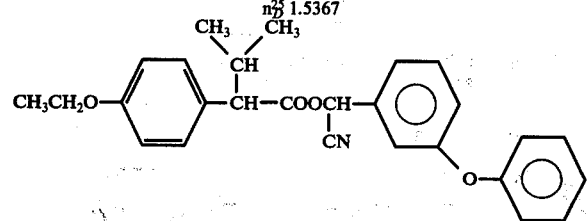<br>3'-Phenoxy-α'-cyanobenzyl-α-isopropyl-4-ethoxyphenylacetate<br>$n_D^{25}$ 1.5208 |
| 35. | 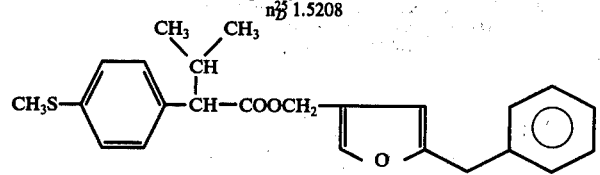<br>5'-Benzyl-3'-furylmethyl-α-isopropyl-4-methylthiophenylacetate<br>$n_D^{25}$ 1.5335 |
| 36. | 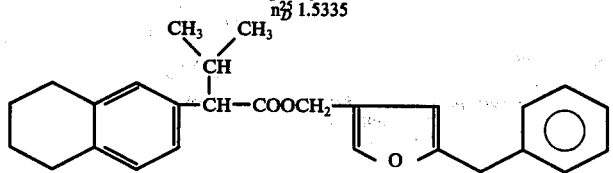<br>5'-Benzyl-3'-furylmethyl-α-isopropyl-1,2,3,4-tetrahydronaphthalene-6-yl-acetate<br>$n_D^{21}$ 1.3689 |
| 37. | 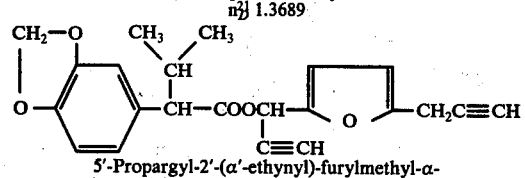<br>5'-Propargyl-2'-(α'-ethynyl)-furylmethyl-α-isopropyl-3,4-methylenedioxyphenylacetate<br>$n_D^{21}$ 1.5236 |
| 38. | 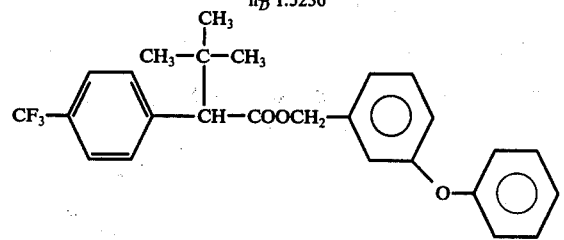<br>3'-Phenoxybenzyl-α-t-butyl-4-trifluoromethylphenylacetate<br>$n_D^{25}$ 1.5671 |

| Compound No. | |
|---|---|
| 39. | 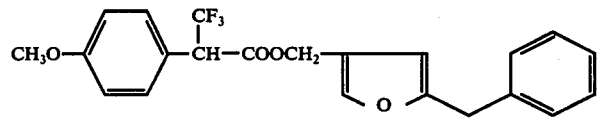 5'-Benzyl-3'-furylmethyl-α-trifluoromethyl-4-methoxyphenylacetate $n_D^{25}$ 1.5474 |
| 40. | 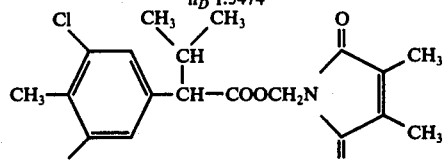 Dimethylmaleimidomethyl-α-isopropyl-3,5-dichloro-4-methylphenylacetate $n_D^{25}$ 1.5239 |
| 41. | 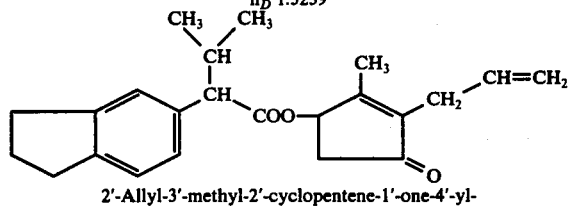 2'-Allyl-3'-methyl-2'-cyclopentene-1'-one-4'-yl-α-isopropyl-5-indanylacetate $n_D^{25}$ 1.5753 |
| 42. | 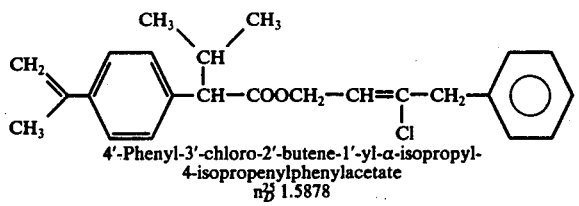 4'-Phenyl-3'-chloro-2'-butene-1'-yl-α-isopropyl-4-isopropenylphenylacetate $n_D^{25}$ 1.5878 |
| 43. | 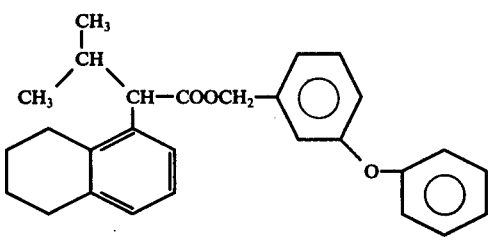 3'-Phenoxybenzyl-α-isopropyl-5-(1,2,3,4-tetrahydro)-naphthalenylacetate $n_D^{20}$ 1.5660 |
| 44. | 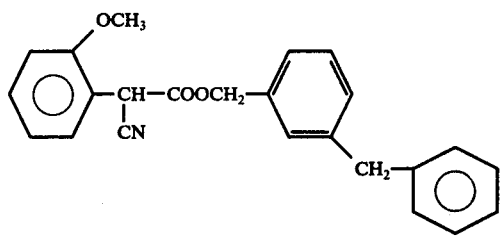 3'-Benzylbenzyl-α-cyano-2-methoxyphenylacetate $n_D^{23}$ 1.5702 |
| 45. | 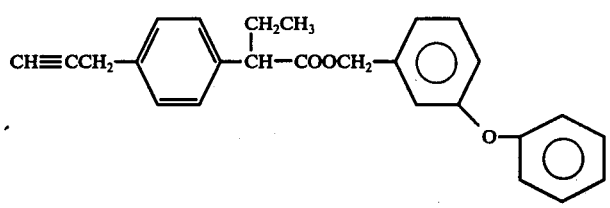 3'-Phenoxybenzyl-α-ethyl-4-propargylphenylacetate $n_D^{25}$ 1.5513 |

| Compound No. | |
|---|---|
| 46. | 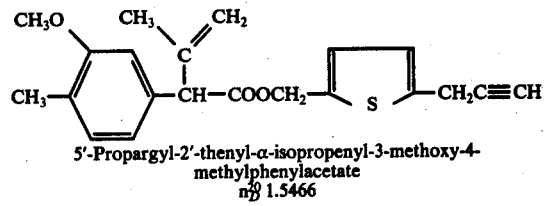<br>5'-Propargyl-2'-thenyl-α-isopropenyl-3-methoxy-4-methylphenylacetate<br>$n_D^{20}$ 1.5466 |
| 47. | 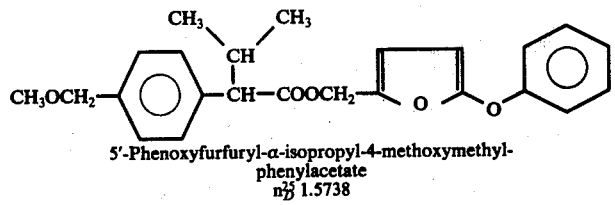<br>5'-Phenoxyfurfuryl-α-isopropyl-4-methoxymethyl-phenylacetate<br>$n_D^{25}$ 1.5738 |
| 48. | 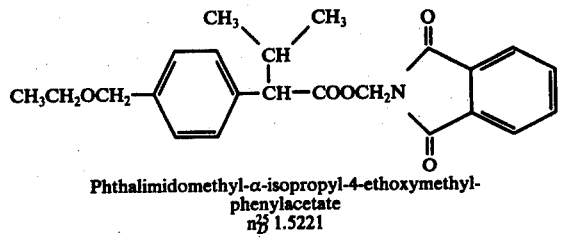<br>Phthalimidomethyl-α-isopropyl-4-ethoxymethyl-phenylacetate<br>$n_D^{25}$ 1.5221 |
| 49. | 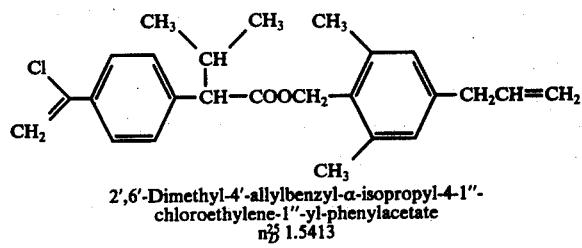<br>2',6'-Dimethyl-4'-allylbenzyl-α-isopropyl-4-1''-chloroethylene-1''-yl-phenylacetate<br>$n_D^{25}$ 1.5413 |
| 50. | 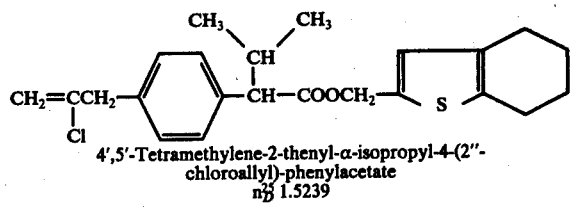<br>4',5'-Tetramethylene-2-thenyl-α-isopropyl-4-(2''-chloroallyl)-phenylacetate<br>$n_D^{25}$ 1.5239 |
| 51. | 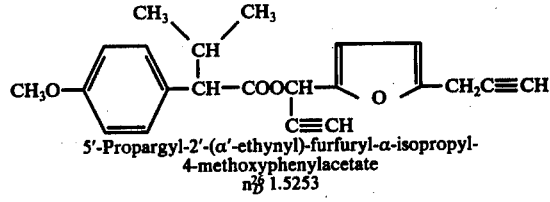<br>5'-Propargyl-2'-(α'-ethynyl)-furfuryl-α-isopropyl-4-methoxyphenylacetate<br>$n_D^{25}$ 1.5253 |
| 52. | 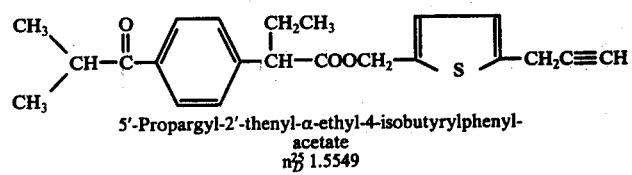<br>5'-Propargyl-2'-thenyl-α-ethyl-4-isobutyrylphenyl-acetate<br>$n_D^{25}$ 1.5549 |
| 53. | 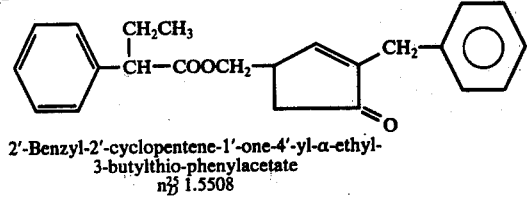<br>2'-Benzyl-2'-cyclopentene-1'-one-4'-yl-α-ethyl-3-butylthio-phenylacetate<br>$n_D^{25}$ 1.5508 |

| Compound No. | |
|---|---|
| 54. | 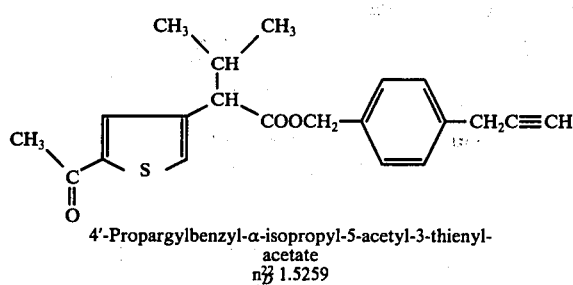
4'-Propargylbenzyl-α-isopropyl-5-acetyl-3-thienyl-acetate
$n_D^{22}$ 1.5259 |
| 55. | 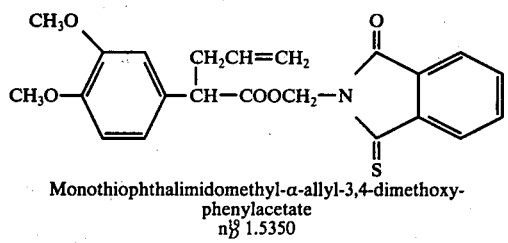
Monothiophthalimidomethyl-α-allyl-3,4-dimethoxy-phenylacetate
$n_D^{19}$ 1.5350 |
| 56. | 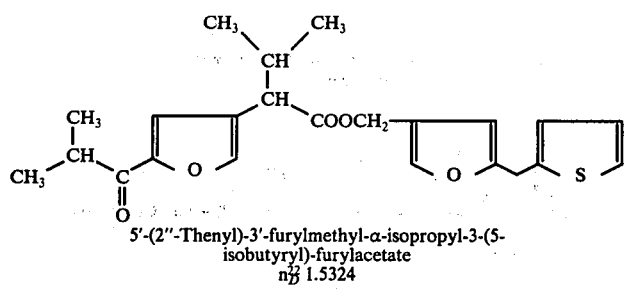
5'-(2''-Thenyl)-3'-furylmethyl-α-isopropyl-3-(5-isobutyryl)-furylacetate
$n_D^{22}$ 1.5324 |
| 57. | 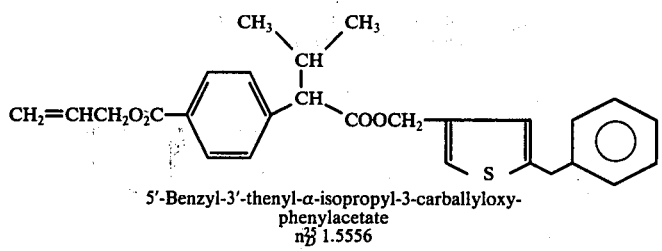
5'-Benzyl-3'-thenyl-α-isopropyl-3-carballyloxy-phenylacetate
$n_D^{25}$ 1.5556 |
| 58. | 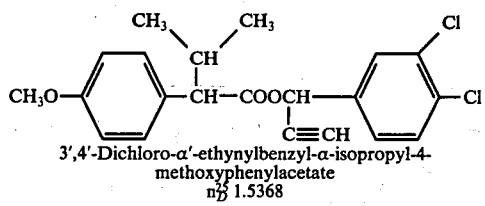
3',4'-Dichloro-α'-ethynylbenzyl-α-isopropyl-4-methoxyphenylacetate
$n_D^{25}$ 1.5368 |
| 59. | 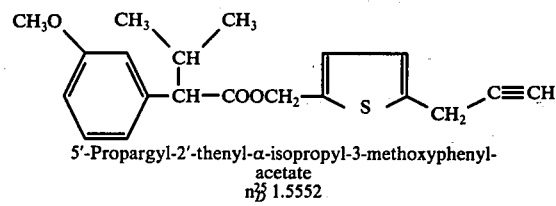
5'-Propargyl-2'-thenyl-α-isopropyl-3-methoxyphenyl-acetate
$n_D^{25}$ 1.5552 |
| 60. | 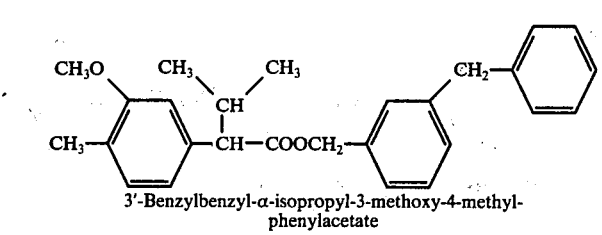
3'-Benzylbenzyl-α-isopropyl-3-methoxy-4-methyl-phenylacetate |

| Compound No. | |
|---|---|
| | $n_D^{25}$ 1.5509 |
| 61. | 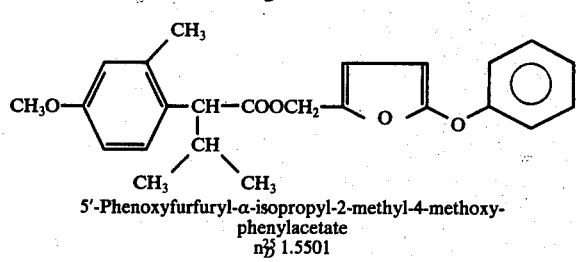<br>5'-Phenoxyfurfuryl-α-isopropyl-2-methyl-4-methoxy-phenylacetate<br>$n_D^{25}$ 1.5501 |
| 62. | 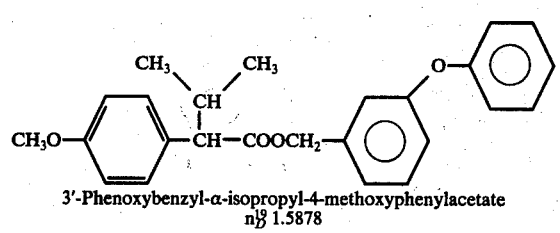<br>3'-Phenoxybenzyl-α-isopropyl-4-methoxyphenylacetate<br>$n_D^{19}$ 1.5878 |
| 63. | 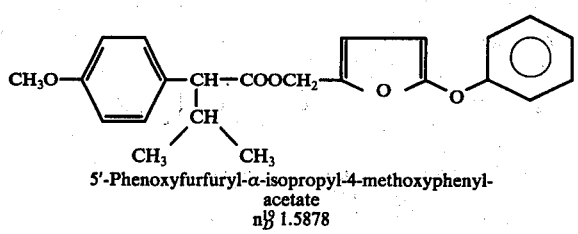<br>5'-Phenoxyfurfuryl-α-isopropyl-4-methoxyphenyl-acetate<br>$n_D^{19}$ 1.5878 |
| 64. | 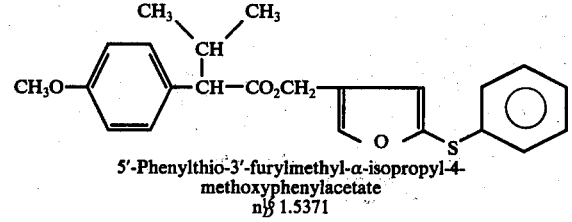<br>5'-Phenylthio-3'-furylmethyl-α-isopropyl-4-methoxyphenylacetate<br>$n_D^{15}$ 1.5371 |
| 65. | 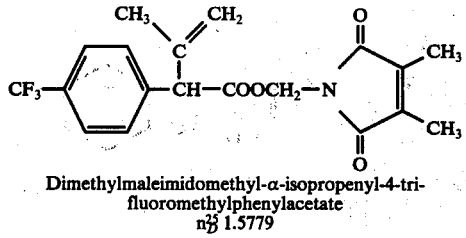<br>Dimethylmaleimidomethyl-α-isopropenyl-4-tri-fluoromethylphenylacetate<br>$n_D^{25}$ 1.5779 |
| 66. | 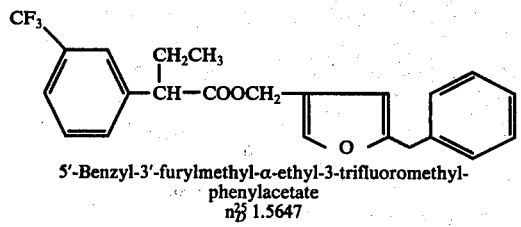<br>5'-Benzyl-3'-furylmethyl-α-ethyl-3-trifluoromethyl-phenylacetate<br>$n_D^{25}$ 1.5647 |
| 67. | 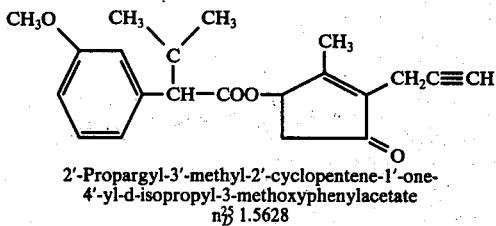<br>2'-Propargyl-3'-methyl-2'-cyclopentene-1'-one-4'-yl-d-isopropyl-3-methoxyphenylacetate<br>$n_D^{25}$ 1.5628 |

| Compound No. | |
|---|---|
| 68. | 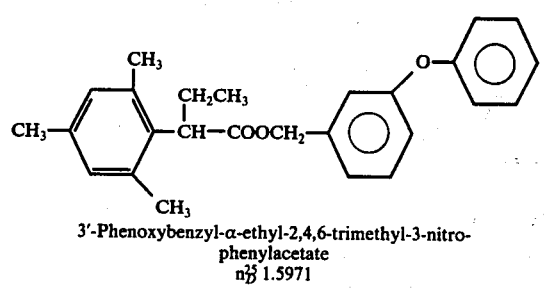 3'-Phenoxybenzyl-α-ethyl-2,4,6-trimethyl-3-nitro-phenylacetate $n_D^{25}$ 1.5971 |
| 69. | 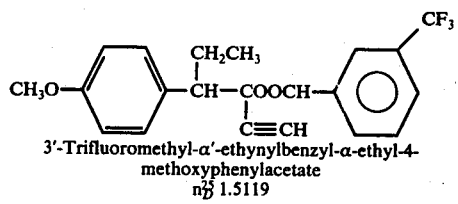 3'-Trifluoromethyl-α'-ethynylbenzyl-α-ethyl-4-methoxyphenylacetate $n_D^{25}$ 1.5119 |
| 70. | 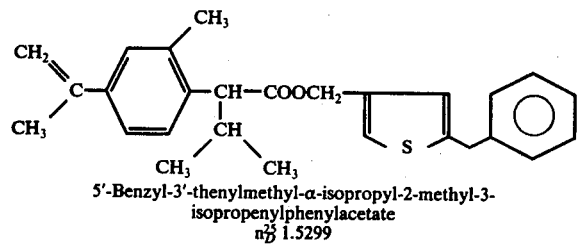 5'-Benzyl-3'-thenylmethyl-α-isopropyl-2-methyl-3-isopropenylphenylacetate $n_D^{25}$ 1.5299 |
| 71. | 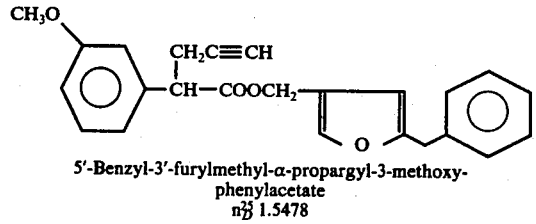 5'-Benzyl-3'-furylmethyl-α-propargyl-3-methoxy-phenylacetate $n_D^{25}$ 1.5478 |
| 72. | 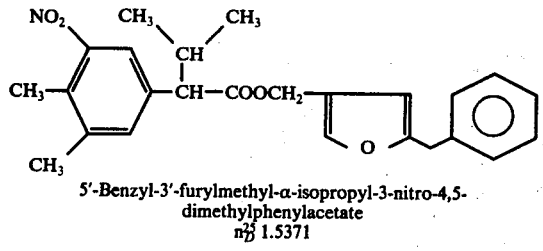 5'-Benzyl-3'-furylmethyl-α-isopropyl-3-nitro-4,5-dimethylphenylacetate $n_D^{25}$ 1.5371 |
| 73. | 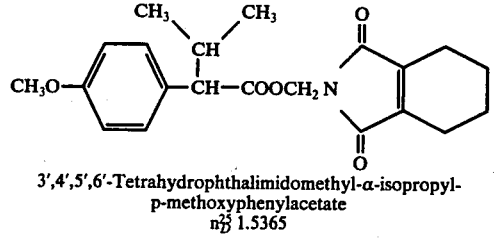 3',4',5',6'-Tetrahydrophthalimidomethyl-α-isopropyl-p-methoxyphenylacetate $n_D^{25}$ 1.5365 |
| 74. | 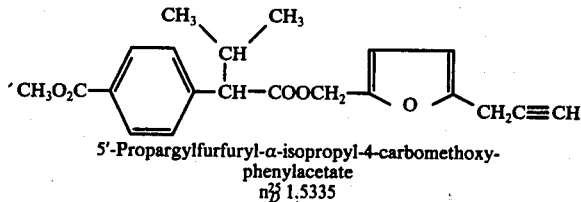 5'-Propargylfurfuryl-α-isopropyl-4-carbomethoxy-phenylacetate $n_D^{25}$ 1.5335 |

| Compound No. | |
|---|---|
| 75. | 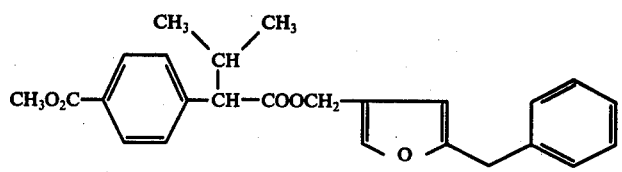<br>5'-Benzyl-3'-furylmethyl-α-isopropyl-4-carbomethoxy-phenylacetate<br>$n_D^{24}$ 1.5640 |
| 76. | 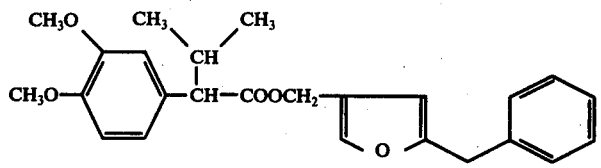<br>5'-Benzyl-3'-furylmethyl-α-isopropyl-3,4-dimethoxy-phenylacetate<br>$n_D^{25}$ 1.5456 |
| 77. | 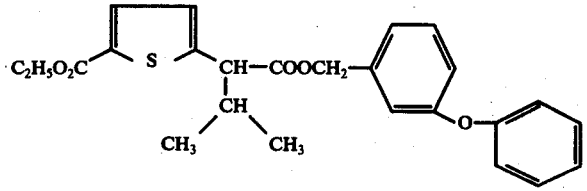<br>3'-Phenoxybenzyl-α-isopropyl-5-carbethoxy-2-thenylacetate<br>$n_D^{25}$ 1.5777 |
| 78. | 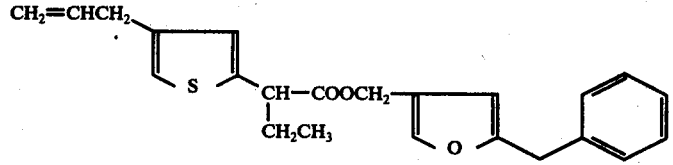<br>5'-Benzyl-3'-furylmethyl-α-ethyl-4-allyl-2-thenyl-acetate<br>$n_D^{25}$ 1.5510 |
| 79. | 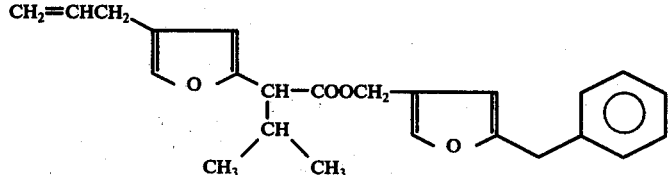<br>5'-Benzyl-3'-furylmethyl-α-isopropyl-4-allyl-2-furylacetate<br>$n_D^{25}$ 1.5356 |
| 80. | 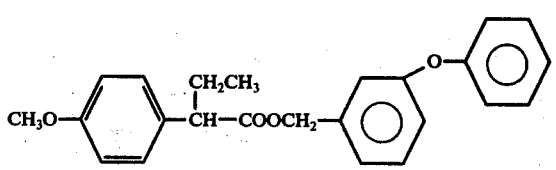<br>3'-Phenoxybenzyl-α-ethyl-4-methoxyphenylacetate<br>$n_D^{19}$ 1.5671 |
| 81. | 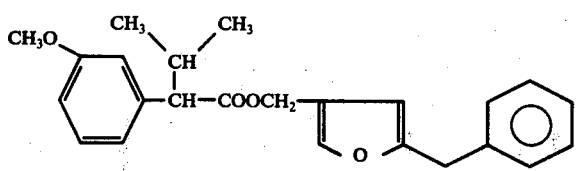<br>5'-Benzyl-3'-furylmethyl-α-isopropyl-3-methoxy-phenylacetate<br>$n_D^{19}$ 1.5411 |

| Compound No. | |
|---|---|
| 82. | 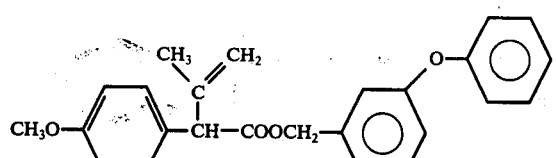<br>3'-Phenoxybenzyl-α-isopropenyl-4-methoxyphenylacetate<br>$n_D^{16}1.5798$ |
| 83. | 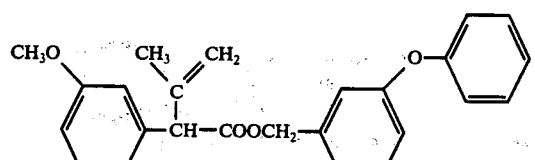<br>3'-Phenoxybenzyl-α-isopropenyl-3-methoxyphenylacetate<br>$n_D^{18}1.5687$ |
| 84. | 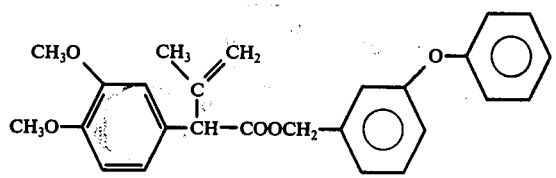<br>3'-Phenoxybenzyl-α-isopropenyl-3,4-dimethoxyphenyl-<br>acetate<br>$n_D^{20}1.5713$ |
| 85. | 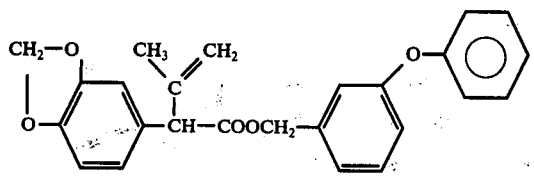<br>3'-Phenoxybenzyl- α-isopropenyl-3,4-methylenedioxy-<br>phenylacetate<br>$n_D^{29}1.5535$ |
| 86. | 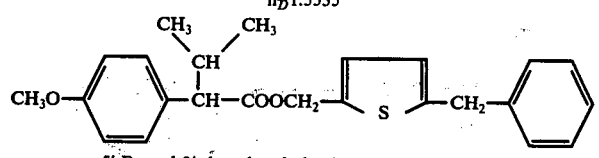<br>5'-Benzyl-2'-thenylmethyl-α-isopropyl-4-methoxy-<br>phenylacetate<br>$n_D^{29}1.5571$ |
| 87. | 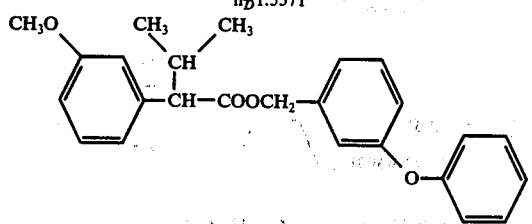<br>3'-Phenoxybenzyl-α-isopropyl-3-methoxypenylacetate<br>$n_D^{17}1.5377$ |
| 88. | 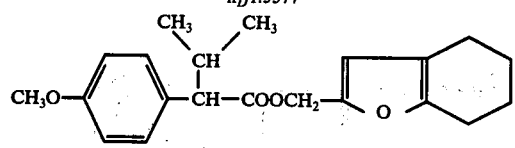<br>4',5'-Tetramethylenefurfuryl-α-isopropyl-4-methoxy-<br>phenylacetate<br>$n_D^{19}1.5467$ |

-continued

| Compound No. | |
|---|---|
| 89. | 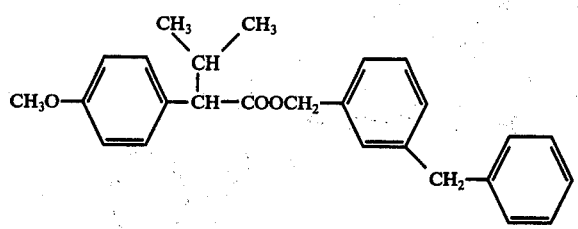
3'-Benzylbenzyl-α-isopropyl-4-methoxyphenylacetate
$n_D^{20}$ 1.5313 |
| 90. | 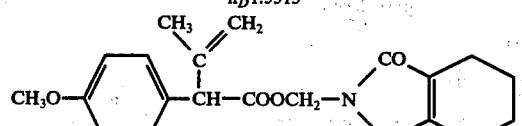
3',4',5',6'-Tetrahydrophthalimidomethyl-α-iso-
propenyl-4-methoxyphenylacetate
$n_D^{21}$ 1.5211 |
| 91. | 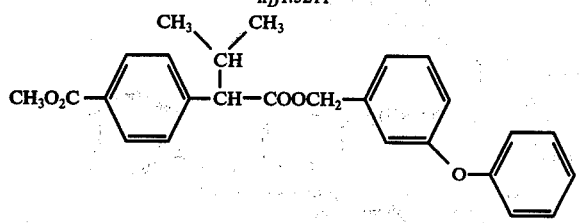
3'-Phenoxybenzyl-α-isopropyl-4-carbomethoxyphenyl-
acetate
$n_D^{20}$ 1.5413 |
| 92. | 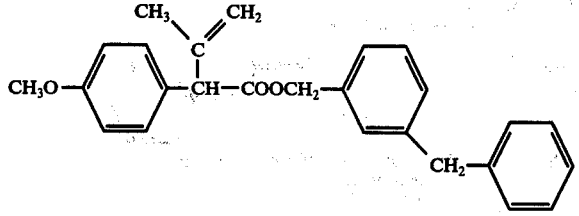
3'-Benzylbenzyl-α-isopropenyl-4-methoxyphenylacetate
$n_D^{19}$ 1.5339 |
| 93. | 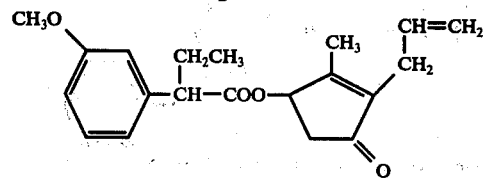
2'-Allyl-3'-methyl-2'-cyclopentene-1'-one-4-
α-ethyl-3-methoxyphenylacetate
$n_D^{19}$ 1.5211 |
| 94. | 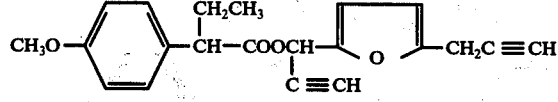
5'-Propargyl-α'-ethynylfurfuryl-α-ethyl-4-methoxy-
phenylacetate
$n_D^{20}$ 1.5467 |
| 95. | 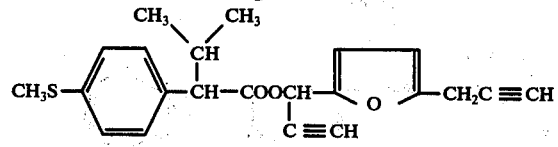
5'-Propargyl-α'-ethynylfurfuryl-α-isopropyl-4-
methylthiophenylacetate
$n_D^{20}$ 1.5518 |

-continued

| Compound No. | |
|---|---|
| 96. | 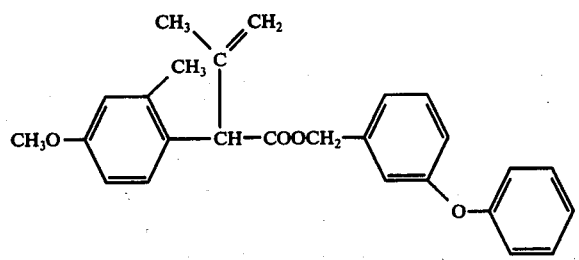
3'-Phenoxybenzyl-α-isopropenyl-2-methyl-4-methoxy-phenylacetate
$n_D^{20}$ 1.5396 |
| 97. | 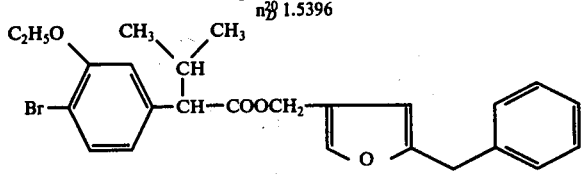
5'-Benzyl-3'-furylmethyl-α-isopropyl-3-ethoxy-4-bromophenylacetate
$n_D^{20}$ 1.5218 |
| 98. | 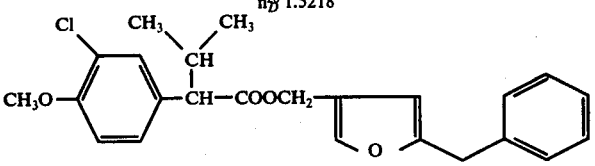
5'-Benzyl-3'-furylmethyl-α-isopropyl-3-chloro-4-methoxyphenylacetate
$n_D^{20}$ 1.5416 |
| 99. | 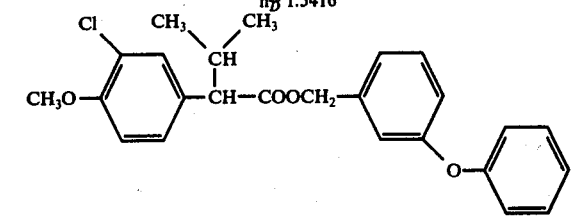
3'-Phenoxybenzyl-α-isopropyl-3-chloro-4-methoxy-phenylacetate
$n_D^{20}$ 1.5467 |
| 100. | 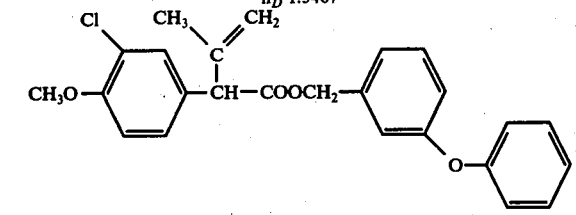
3'-Phenoxybenzyl-α-isopropenyl-3-chloro-4-methoxy-phenylacetate
$n_D^{20}$ 1.5331 |
| 101. | 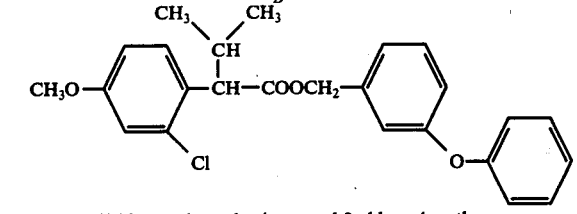
3'-Phenoxybenzyl-α-isopropyl-2-chloro-4-methoxy-phenylacetate
$n_D^{20}$ 1.5476 |
| 102. | 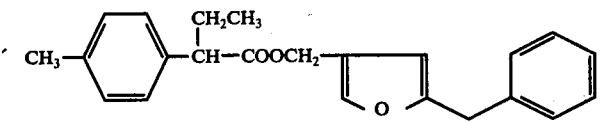
5'-Benzyl-3'-furylmethyl-α-ethyl-4-methylphenyl-acetate
$n_D^{23}$ 1.5474 |

| Compound No. | |
|---|---|
| 103. | 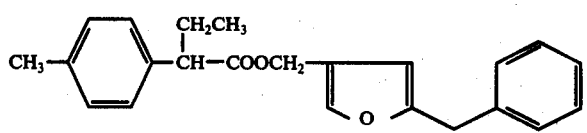<br>5′-Benzyl-3′-furylmethyl-α-isopropyl-4-methyl-phenylacetate<br>$n_D^{25}$ 1.5433 |
| 104. | 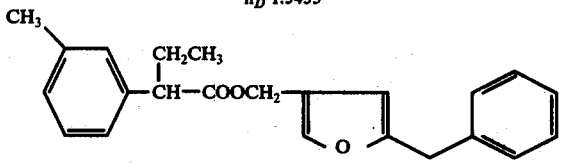<br>5′-Benzyl-3′-furymethyl-α-ethyl-3-methylphenyl-acetate<br>$n_D^{25}$ 1.5470 |
| 105. | 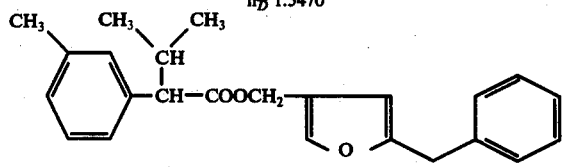<br>5′-Benzyl-3′-furylmethyl-α-isopropyl-3-methyl-phenylacetate<br>$n_D^{25.5}$ 1.5430 |
| 106. | 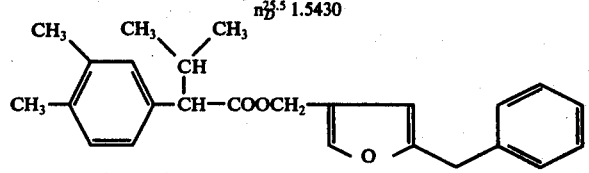<br>5′-Benzyl-3′-furylmethyl-α-isopropyl-3,4-dimethyl-phenylacetate<br>$n_D^{25.5}$ 1.5238 |
| 107. | 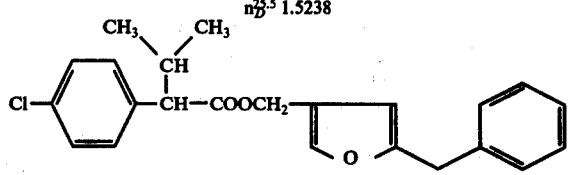<br>5′-Benzyl-3′-furylmethyl-α-isopropyl-4-chloro-phenylacetate<br>$n_D^{25.5}$ 1.5241 |
| 108. | 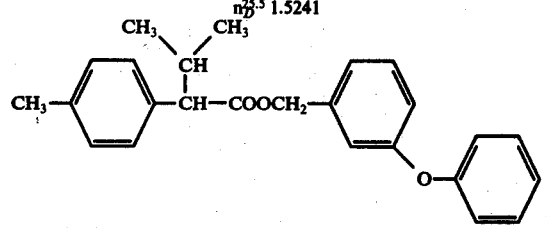<br>3′-Phenoxybenzyl-α-isopropyl-4-methylphenylacetate<br>$n_D^{28.5}$ 1.5596 |
| 109. | 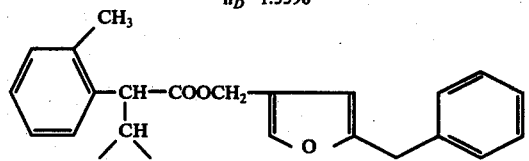<br>5′-Benzyl-3′-furylmethyl-α-isopropyl-2-methyl-phenylacetate<br>$n_D^{26.5}$ 1.5431 |
| 110. | 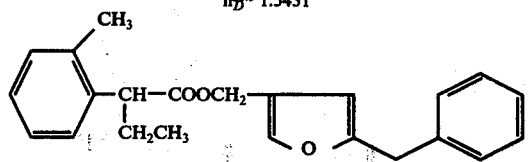<br>5′-Benzyl-3′-furylmethyl-α-ethyl-2-methylphenyl-acetate<br>$n_D^{26.5}$ 1.5501 |

| Compound No. | |
|---|---|
| 111. | 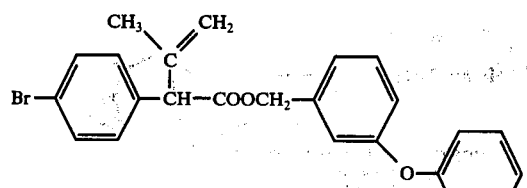<br>3'-Phenoxybenzyl-α-isopropenyl-4-bromophenylacetate<br>$n_D^{20}$ 1.5278 |
| 112. | 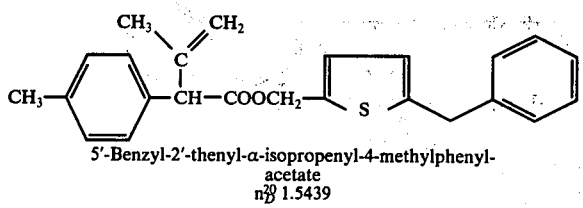<br>5'-Benzyl-2'-thenyl-α-isopropenyl-4-methylphenyl-<br>acetate<br>$n_D^{20}$ 1.5439 |
| 113. | 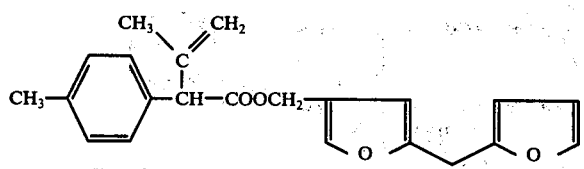<br>5'-Furfuryl-3'-furylmethyl-α-isopropenyl-4-methyl-<br>phenylacetate<br>$n_D^{20}$ 1.5411 |
| 114. | 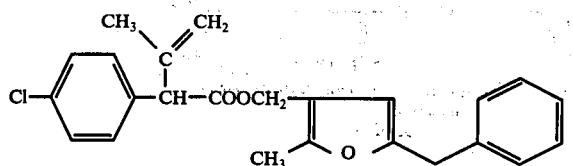<br>5'-Benzyl-2'-methyl-3'-furylmethyl-α-isopropenyl-4-<br>chlorophenylacetate<br>$n_D^{25}$ 1.5212 |
| 115. | 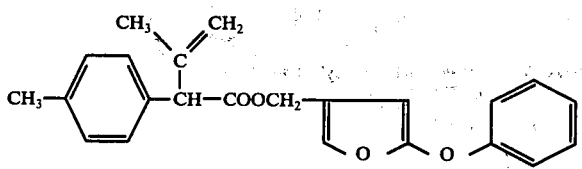<br>5'-Phenoxy-3'-furylmethyl-α-isopropenyl-4-methyl<br>phenylacetate<br>$n_D^{25}$ 1.5471 |
| 116. | 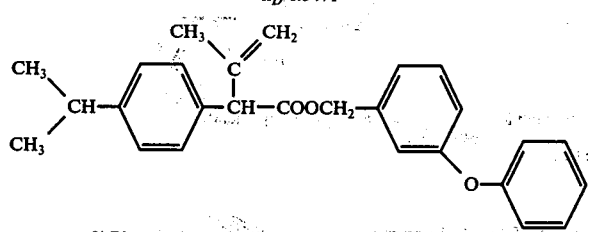<br>3'-Phenoxybenzyl-α-isopropenyl-4-isopropylphenyl-<br>acetate<br>$n_D^{20}$ 1.5218 |
| 117. | 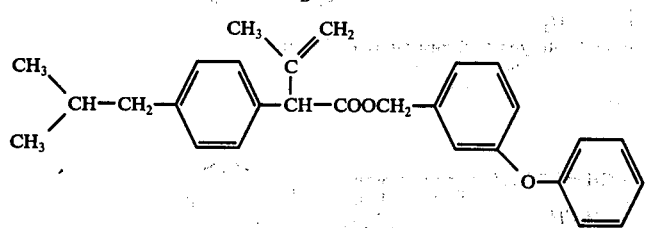<br>3'-Phenoxybenzyl-α-isopropenyl-4-isobutylphenyl-<br>acetate<br>$n_D^{20}$ 1.5236 |

| Compound No. | | |
|---|---|---|
| 118. | 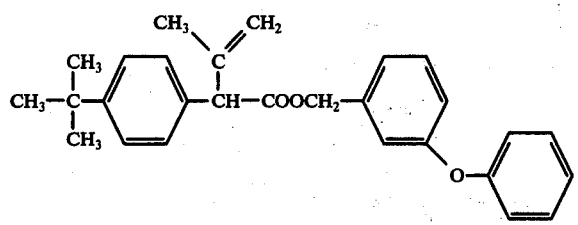 | |

3'-Phenoxybenzyl-α-isopropenyl-4-t-butylphenyl-
acetate
$n_D^{20}$ 1.5311

| 119. | 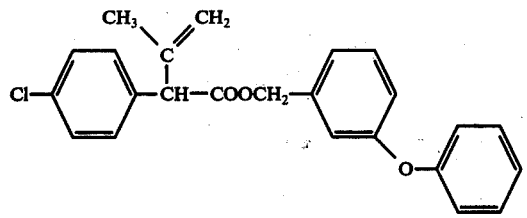 |
|---|---|

3'-Phenoxybenzyl-α-isopropenyl-4-chlorophenylacetate
$n_D^{21}$ 1.5322

| 120. | 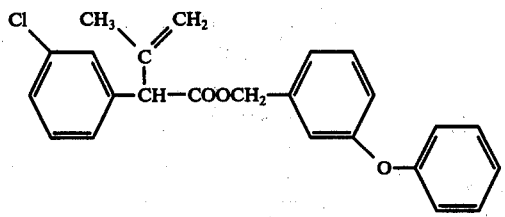 |
|---|---|

3'-Phenoxybenzyl-α-isopropenyl-3-chlorophenylacetate
$n_D^{21}$ 1.5393

| 121. | 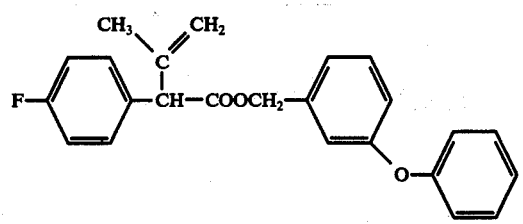 |
|---|---|

3'-Phenoxybenzyl-α-isopropenyl-4-fluorophenylacetate
$n_D^{20}$ 1.5363

| 122. | 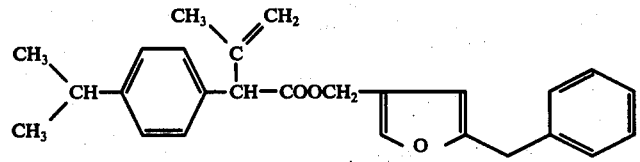 |
|---|---|

5'-Benzyl-3'-furylmethyl-α-isopropenyl-4-isopropyl-
phenylacetate
$n_D^{19}$ 1.5428

| 123. | 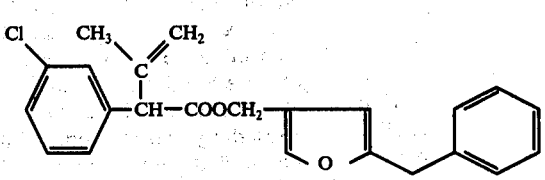 |
|---|---|

5'-Benzyl-3'-furylmethyl-α-isopropenyl-3-chloro-
phenylacetate
$n_D^{17}$ 1.5411

-continued

| Compound No. | |
|---|---|
| 124. | 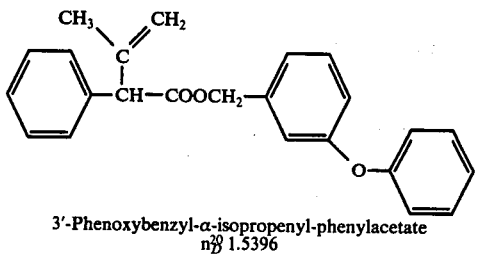
3'-Phenoxybenzyl-α-isopropenyl-phenylacetate
$n_D^{20}$ 1.5396 |
| 125. | 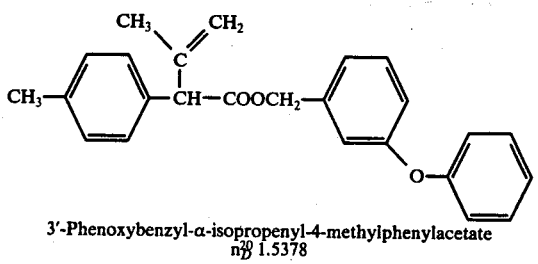
3'-Phenoxybenzyl-α-isopropenyl-4-methylphenylacetate
$n_D^{20}$ 1.5378 |
| 126. | 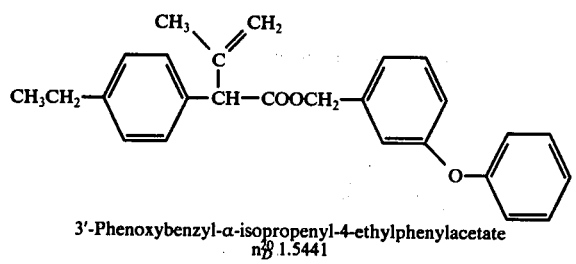
3'-Phenoxybenzyl-α-isopropenyl-4-ethylphenylacetate
$n_D^{20}$ 1.5441 |
| 127. | 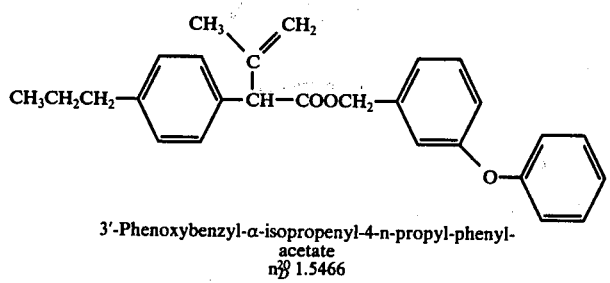
3'-Phenoxybenzyl-α-isopropenyl-4-n-propyl-phenyl-acetate
$n_D^{20}$ 1.5466 |
| 128. | 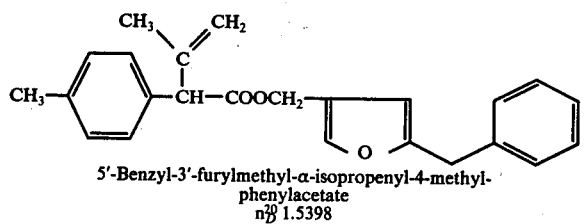
5'-Benzyl-3'-furylmethyl-α-isopropenyl-4-methyl-phenylacetate
$n_D^{20}$ 1.5398 |

The process for preparing the esters in accordance with the present invention is illustrated by the following Preparations, but the present invention is not limited thereto.

PREPARATION 1

Preparation of 5'-benzyl-3'-furylmethyl-α-ethyl phenylacetate (Compound No. 1)

6.20 g (0.02 mole) of α-ethylphenylacetic anhydride and 3.76 g (0.02 mole) of 5-benzyl-3-furylmethylalcohol were dissolved in 50 ml of dry pyridine and the mixture was stirred at room temperature for 2 hours. The resulting reaction mixture was poured into 100 g of ice water and extracted with three 20 ml portions of ethyl ether. The combined ether layer was then extracted with two 20 ml portions of 5% aqueous sodium hydroxide to remove α-ethylphenylacetic acid as a by-product. The ether layer was washed successively with 10% hydrochloric acid, saturated aqueous sodium bicarbonate and saturated sodium chloride, dried over anhydrous sodium sulfate, and the ether was removed under reduced pressure to obtain 6.25 g of crude ester as a pale yellow oily substance. The resulting oily substance was then purified by column chromatography using 120 g of activated alumina and a developing solvent of benzene-n-hexane (1:3) to obtain 5.68 g (85% theoretical yield) of the desired ester as a colorless oily substance.

$n_D^{17}$ 1.5545.

$\nu_{max}^{film}$ 3005, 1724, 1550, 1407, 1180, 806 cm$^{-1}$ $\delta_{ppm}^{CCl_4}$ 7.16 (S. 5H), 7.15 (S. 5H), 7.2 (1H), 5.79 (bs. 1H), 4.78 (S. 2H), 3.78 (S. 2H), 3.31 (t. 1H, J=7Hz), 1.3 – 2.3 (m. 2H), 0.83 (t. 3H, J=7Hz).

PREPARATION 2

Preparation of m-phenoxybenzyl-α-ethylphenylacetate (Compound No. 2)

2.00 g (0.01 mole) of m-phenoxybenzyl alcohol and 1.19 g (0.015 mole) of dry pyridine were dissolved in 20 ml of benzene, and 1.83 g (0.01 mole) of α-ethylphenylacetyl chloride dissolved in 5 ml of dry benzene was added dropwise thereto under ice-cooling. After completion of addition, the mixture was stirred at room temperature for 3 hours to complete the reaction, and the reaction mixture was poured into 30 g of ice-water. The mixture was separated, and the aqueous layer was extracted with two 10 ml portions of benzene. The combined benzene layer was washed successively with 5% hydrochloric acid, saturated aqueous sodium bicarbonate and saturated aqueous sodium chloride, and benzene was removed under reduced pressure. The resulting crude ester was charged into a column packed with 40 g of activated alumina using a mixture of benzene-n-hexane (1:3) as an eluent to obtain 3.15 g (91% theoretical yield) of the purified ester.

$n_D^{22}$ 1.5712.
$\nu_{max}^{film}$ 3030, 1740, 1590, 1470, 1260, 1220, 1160 cm$^{-1}$.
$\delta_{ppm}^{CCl_4}$ 7.4 – 5.8 (m. 14H), 4.95 (S. 2H), 3.48 (t. 1H, J=8Hz), 2.3 – 1.1 (m. 2H), 0.85 (t. 3H, J=8Hz).

PREPARATION 17

Preparation of 5'-benzyl-3'-furylmethyl-α-cyclohexylphenylacetate (Compound No. 17)

2.82 g (0.015 mole) of 5-benzyl-3-furylmethyl alcohol and 2.22 g (0.01 mole) of ethyl-α-cyclohexylphenylacetate were dissolved in 50 ml of dry toluene and 0.1 g of sodium hydride was added thereto as a catalyst. The mixture was charged into a Teflon Spinning Band rectification tower and ethanol formed as a by-product was removed while heating and stirring. The reaction was completed in about 1 hour, and the reaction mixture was allowed to stand and cooled to room temperature and poured into 30 g of ice-water. The layers were separated to remove the toluene layer and the toluene layer was washed with saturated aqueous sodium chloride. Toluene was removed under reduced pressure, and the resulting crude ester was subjected to a column packed with 50 g of activated alumina using benzene-n-hexane (1:3) as an eluent to obtain 2.79 g (72% theoretical yield) of the purified ester as white crystals.

Melting point, 51° – 53° C.
$\nu_{max}^{nujol}$ 3035, 1738, 1606, 1500, 1454, 1155 cm$^{-1}$.
$\delta_{ppm}^{CCl_4}$ 7.3 – 6.9 (m. 11H), 5.80 (bs. 1H), 4.77 (AB. q 2H), 3.70 (S. 2H), 3.06 (d. 2H, J=10Hz), 2.1 – 0.6 (m. 10H).

PREPARATION 5

Preparation of dimethylmaleimidomethyl-α-allylphenylacetate (Compound No. 5)

1.74 g (0.01 mole) of N-chloromethyldimethylmaleimide and 2.93 g (0.01 mole) of silver α-allylphenylacetate were added to 25 ml of dimethylformamide and the mixture was allowed to stand overnight at room temperature. The precipitated crystals were filtered and dimethylformamide was distilled off under reduced pressure. The resulting crude ester was subjected to a silica gel column (90 g) using a mixture of chloroform-carbon tetrachloride (2:1) as an eluent to obtain 2.43 g (75% theoretical yield) of the desired ester as a white oily substance.

$n_D^{22.0}$ 1.5349.
$\nu_{max}^{film}$ 1780, 1740, 1720, 1640, 1600, 1140, 910 cm$^{-1}$.
$\delta_{ppm}^{CDCl_3}$ 7.15 (S. 5H), 6.0 – 4.9 (m. 3H), 3.48 (t. 3H, J=10Hz), 3.0 – 2.0 (m. 2H), 2.0 (S. 6H).

PREPARATION 22 Preparation of 5'-benzyl-3'-furylmethyl-α-isopropyl-4-methoxyphenylacetate (Compound No. 22)

1.90 g (0.01 mole) of 5'-benzyl-3-furfuryl alcohol and 1.58 g (0.02 mole) of pyridine were dissolved in 50 ml of dry benzene, and 2.30 g (0.01 mole) of α-isopropyl-4-methoxy-phenylacetyl chloride dissolved in 5 ml of dry benzene was added dropwise to the solution over about 30 minutes. After completion of the addition, the mixture was stirred at room temperature for 3 hours to complete the reaction. The reaction mixture was poured into 50 g of ice-water followed by separating the benzene layer, and the aqueous layer was extracted with two 20 ml portions of benzene. The combined benzene layer was washed successively with 5% hydrochloric acid, saturated aqueous sodium bicarbonate and saturated aqueous sodium chloride. A yellow oily substance obtained after removal of benzene was subjected to a column packed with 25 g of activated alumina using benzene-n-hexane (1:3) as an eluent to obtain 3.33 g (86.0% theoretical yield) of the purified ester as a colorless oily substance.

$n_D^{17}$ 1.5470.
$\nu_{max}^{film}$ 1735, 1617, 1515, 1250, 1032, 830, 730 cm$^{-1}$.
$\delta_{ppm}^{CCl_4}$ 0.65 (d, 3H, J=7Hz), 0.95 (d. 3H, J=7Hz), 1.7 – 2.5 (m. 1H), 2.97 (d. 1H, J=11Hz), 3.67 (S. 3H), 3.81 (S. 2H), 4.78 (d.d. 2H), 5.83 (b.s. 1H), 6.90 (d.d 4H), 7.1 – 7.3 (m. 6H).

PREPARATION 27

Preparation of 3,4,5,6-tetrahydrophthalimidomethyl-α-ethyl2,4,6-trimethylphenylacetate (Compound No. 27)

10.31 g (0.05 mole) of α-ethyl-2,4,6-trimethylphenylacetic acid and 9.05 g (0.05 mole) of 3,4,5,6-tetrahydrophthalimidomethylol were dissolved in 100 ml of dry benzene, and 16.51 g (0.08 mole) of dicyclohexylcarbodiimide was added to the solution. The mixture was then allowed to stand overnight in a sealed vessel. On next day, the mixture was heated at reflux to complete the reaction, and, after allowing to cool, the precipitated dicyclohexylurea was separated by filtration. A viscous oily substance obtained by concentration of the filtrate was subjected to a silica gel column (360 g) to obtain 11.3 g (61.18% theoretical yield) of the purified ester as a colorless viscous oily substance.

$n_D^{25}$ 1.5399.
$\nu_{max}^{film}$ 1780, 1740, 1720, 1511, 1405, 1140 cm$^{-1}$.
$\delta_{ppm}^{CCl_4}$ 0.85 (t. 3H, J=7Hz), 1.5 – 2.3 (m. 2H), 2.3 (b.S. 9H), 3.32 (t. 3H, J=8Hz), 1.5 – 2.0 (m. 4H), 2.0 – 2.5 (m. 4H), 5.34 (d.d. 2H), 7.0 – 7.3 (m. 2H).

PREPARATION 47

Preparation of 2'-allyl-3'-methyl-2'-cyclopentene-1'-one-4'-yl-α-ethyl-3-methoxyphenylacetate (Compound No. 93)

7.41 g (0.02 mole) of α-ethyl-3-methoxyphenylacetic anhydride and 1.52 g (0.01 mole) of 2-allyl-3-methyl-4-hydroxy-2-cyclopentene-1-one dissolved in 50 ml of dry pyridine, and the mixture was stirred overnight at room temperature. On the next day, the reaction mixture was poured into 100 g of ice water and extracted with three 20 ml portions of ethyl ether. The combined ether layer was then extracted with two 30 ml portions of 5% aqueous sodium hydroxide to remove a carboxylic acid formed as a by-product. The ether layer was washed successively with 10% aqueous hydrochloric acid, saturated aqueous sodium bicarbonate and saturated aqueous sodium chloride and dried over anhydrous sodium sulfate. Removal of ether under reduced pressure yielded 3.2 g of a crude ester. The product was then subjected to a column packed with 20 g of activated alumina using benzene-n-hexane (1:3) as an eluent to obtain 2.73 g (83.1% theoretical yield) of the desired ester.

$n_D^{19}$ 1.5211.

$\nu_{max}^{film}$ 1730, 1710, 1150, 1140, 1000, 910 cm$^{-1}$.

$\delta_{ppm}^{CCl_4}$ 0.90 (t. 3H, J=8Hz), 1.5 - 3.0 (m. 11H), 3.36 (t. 1H, J=9Hz), 3.67 (S. 1H), 4.7 - 6.0 (m. 3H), 6.5 - 6.9 (m. 4H).

PREPARATION 46

Preparation of 3'-phenoxybenzyl-α-isopropyl-3-methoxyphenylacetate (Compound No. 87)

8.01 g (0.04 mole) of m-phenoxybenzyl alcohol and 7.09 g (0.03 mole) of ethyl α-isopropyl-3-methoxyphenylacetate were dissolved in 100 ml of dry toluene, and 0.1 g of sodium hydride was added thereto as a catalyst. The mixture was then charged in a Teflon Spinning Band rectifier tower having a length of 50 cm and heated while stirring. The reaction was completed in about 3 hours by removing ethanol as an azeotropic distillation with toluene at the top of the tower. After allowing to stand and cooling, the mixture was poured into cold water to separate layers. Removal of toluene by distillation under reduced pressure yielded 11.5 g of a crude ester. The product was then subjected to a column packed with 55 g of activated alumina using benzene-n-hexane(1:3) as an eluent to obtain 10.12 g (86.4% theoretical yield based on the starting ethyl ester of the desired ester.

$n_D^{17}$ 1.5377

$\nu_{max}^{film}$ 3060, 1738, 1590, 1490, 1255, 1145, 775, 690 cm$^{-1}$ $\delta_{ppm}^{CCl_4}$ 0.70 (d. 3H, J=7Hz), 0.97 (d. 3H, J=7Hz), 0.9 - 2.6 (m. 1H), 3.08 (d. 1H, J=11Hz), 3.65 (S. 3H), 4.95 (AB Type d.d. 2H), 6.5 - 7.4 (m. 13H).

PREPARATION 48

Preparation of 3'-phenoxybenzyl-2-(1',2',3',4'-tetrahydronaphthalene-8'-yl) isovalerate (Compound No. 43)

3.95 g (0.015 mole) of n-phenoxybenzyl bromide, 2.32 g (0.01 mole) of 2-(1',2',3',4'-tetrahydronaphthalene-8'-yl) isovaleric acid and 2.02 g (0.02 mole) of triethylamine were added to 50 ml of dimethylformamide and the mixture was stirred overnight at room temperature. The reaction mixture was poured into 50 g of ice-water and extracted with three 30 ml portions of ethyl ether. The combined ether layer was washed successively with 5% hydrochloric acid, saturated aqueous sodium bicarbonate and saturated aqueous sodium chloride and dried over anhydrous sodium sulfate. Removal of ethyl ether by distillation under reduced pressure yielded a crude ester which was then subjected to a column packed with 20 g of activated alumina using benzene-n-hexane (1:3) as an eluent to obtain 3.45 (83.2% theoretical yield based on the carboxylic acid stating material) of the desired ester as a colorless oily substance.

$n_D^{19}$ 1.5660.

$\nu_{max}^{film}$ 3060, 1736, 1588, 1490, 1255, 770, 690 cm$^{-1}$.

$\delta_{ppm}^{CCl_4}$ 0.68 (d. 3H, J=7Hz), 1.03 (d. 3H, J=7Hz), 1.5 - 2.0 (m. 4H), 2.1 - 2.6 (m. 1H), 2.5 - 3.0 (m. 4H), 2.48 (d. 1H, J=11Hz), 4.74 (S. H), 6.6 - 7.4 (m. 12H).

In a similar manner as described in Preparations 1, 2, 5, 17, 22, 27, 46 and 48, the compounds listed in Table below were obtained. In the table, the symbols "a", "b", "c", "d"and "e" stand for the following esterification methods.

a: Esterification using an acid chloride.
  b: Esterification using an acid anhydride.
  c: Dehydration esterification of an acid and an alcohol with dicyclohexylcarbodiimide in an inert solvent.
  d: Esterification by transesterification using sodium hydride as a catalyst in toluene.
  e: Esterification using a silver or a triethylammonium salt of acid and a halide of an alcohol.

Representative compounds of this invention prepared by the above methods are shown below, but they are not to be construed as limiting the present invention.

| Preparation Exp. No. | Comp. No. | Z | Y | OX | Esterification Method | Yield (%) | Physical Properties Calcd. (%) | Physical Properties Found (%) |
|---|---|---|---|---|---|---|---|---|
| 1 | 1 | $CH_3CH_2-$ | phenyl | $-OCH_2-$(furan with benzyl) | b | 85 | $C_{22}H_{22}O_3$ C: 79.01 H: 6.63 | $n_D^{23}$ 1.5545 78.91 6.54 |
| 2 | 2 | $CH_3CH_2-$ | phenyl | $-OCH_2-$(phenoxyphenyl) | a | 91 | $C_{23}H_{22}O_3$ C: 79.74 H: 6.40 | $n_D^{23}$ 1.5712 79.65 6.41 |
| 3 | 3 | $CH_3CH_2O-$ | phenyl | $-OCH_2-$(phenoxyphenyl) | e | 80 | $C_{23}H_{22}O_4$ C: 76.22 H: 6.12 | $n_D^{23}$ 1.5275 76.19 6.17 |
| 4 | 4 | $CH_3CH_2-$ | phenyl | $-OCH_2-N$(tetrahydrophthalimide) | a | 92 | $C_{19}H_{17}O_4N$ C: 70.57 H: 5.30 N: 4.33 | $n_D^{23}$ 1.5403 70.61 5.28 4.25 |
| 5 | 5 | $CH_2=CH-CH_2-$ | phenyl | $-OCH_2-N$(dimethylmaleimide) | e | 75 | $C_{18}H_{19}O_4N$ C: 68.99 H: 6.11 N: 4.47 | $n_D^{23}$ 1.5349 67.01 6.09 4.42 |
| 6 | 6 | $CH_3CH_2-$ | thienyl | $-OCH_2-$(propargyl furan) | a | 81 | $C_{16}H_{16}O_3S$ C: 66.64 H: 5.59 S: 11.12 | $n_D^{23}$ 1.5835 66.59 5.50 11.18 |
| 7 | 7 | $CH_3-$ | dimethylcyclopentenyl | $-OCH_2-N$(tetrahydrophthalimide) | e | 85 | $C_{18}H_{23}O_4N$ C: 68.12 H: 7.31 N: 4.41 | $n_D^{23}$ 1.5648 68.09 7.22 4.50 |
| 8 | 8 | $CH_3CH_2-$ | phenyl | $-OCH-C\equiv CH$ (furan) | a | 83 | $C_{20}H_{18}O_3$ C: 78.41 H: 5.92 | $n_D^{23}$ 1.5310 78.3 5.86 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 9 | 9 | CH₃CH₂— | 2-methyl-cyclopentanone | —OCH₂-(benzyl-furan) | a | 84 | C₂₂H₂₄O₄ C:74.97 H: 6.86 | n_D^23 1.5123 75.06 6.80 |
| 10 | 10 | CH₃CH₂— | phenyl | —OCH₂-(p-tolyl) | a | 90 | C₂₀H₂₀O₂ C:82.15 H: 6.89 | n_D^23 1.5039 82.05 6.93 |
| 11 | 11 | CH₃— | phenyl | —OCH₂-(tetrahydronaphthyl), —CH₂C≡CH | a | 93 | C₂₀H₂₀O₂ C:81.60 H: 7.53 | n_D^23 1.5536 81.52 7.58 |
| 12 | 12 | CH₃CH₂— | phenyl | —OCH₂-(benzyl-thiophene) | a | 91 | C₂₂H₂₂O₂S C:75.39 H: 6.32 S: 9.15 | n_D^23 1.5488 75.29 6.27 9.20 |
| 13 | 13 | (CH₃)₂CH— | phenyl | —OCH₂-(benzyl-thiophene) | a | 90 | C₂₃H₂₄O₂S C:75.78 H: 6.64 S: 8.79 | n_D^23 1.5613 75.70 6.69 8.81 |
| 14 | 14 | CH₃CH₂— | phenyl | —O-CH(CN)-(phenoxyphenyl) | a | 71 | C₂₄H₂₁O₃N C:77.60 H: 5.70 N: 3.77 | n_D^23 1.5638 77.49 5.97 3.79 |
| 15 | 15 | BrCH₂CH₂— | phenyl | —OCH₂-(benzyl-furan) | a | 89 | C₂₂H₂₁O₃Br C:64.08 H: 5.13 Br:19.38 | n_D^23 1.5911 64.11 5.11 19.29 |
| 16 | 16 | CH₃CH₂— | 2-methyl-furan | —O-(allyl-methyl-cyclopentenone) | a | 90 | C₁₇H₂₀O₃ C:70.81 H: 6.99 | n_D^23 1.5118 70.89 6.77 |
| 17 | 17 | cyclohexyl | phenyl | —OCH₂-(benzyl-furan) | d | 72 | C₂₆H₂₈O₃ C:80.38 H: 7.27 | mp 51~53° C 80.41 7.24 |
| 18 | 18 | CH₃CH₂— | (CH₃)₂C=C(CH₃)— | —OCH₂-(benzyl-furan) | a | 84 | C₂₁H₂₆O₃ C:77.27 H: 8.03 | n_D^23 1.5417 77.41 7.96 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 19 | 19 | CH₂—CH—CH₂— (cyclopropyl) | phenyl | —OCH₂— (furan with CH₃ and ≡CH propargyl) | a | 80 | C₂₁H₂₂O₃ C: 78.23 H: 6.88 | n_D²⁰ 1.5632 78.19 6.94 |
| 20 | 20 | CH₂=CH—CH₂— | 2-methylthiophene | —OCH₂— (furan with propargyl) | a | 90 | C₁₇H₁₆O₃S C: 67.98 H: 5.37 S: 10.68 | n_D²⁰ 1.5274 68.07 5.36 10.64 |
| 21 | 21 | CH₃— | CH₃—CH₂—C(CH₃)=CH— | —OCH₂— (furan with benzyl) | a | 88 | C₂₀H₂₄O₃ C: 76.89 H: 7.74 | n_D²⁰ 1.56 76.80 7.71 |
| 22 | 22 | CH₃—CH—CH₃ | 4-methoxyphenyl | —OCH₂— (furan with CH₂-phenyl) | a | 88 | C₂₄H₂₆O₄ C: 76.16 H: 6.93 | n_D²⁰ 1.5470 76.20 6.89 |
| 23 | 23 | CH₃CH₂— | 3-methoxyphenyl | —OCH₂— (furan with CH₂-phenyl) | b | 83.2 | C₂₃H₂₄O₄ C: 75.80 H: 6.64 | n_D²⁰ 1.5481 75.71 6.69 |
| 24 | 24 | CH₃—CH—CH₃ | 3-methoxyphenyl | —OCH₂— (furan with phenoxy) | c | 79.8 | C₂₆H₂₆O₅ C: 74.26 H: 6.71 | n_D²⁰ 1.5655 74.25 6.77 |
| 25 | 25 | CH₃CH₂— | 4-acetylphenyl (CH₃CO) | —OCH₂— (furan with phenoxy) | c | 81.5 | C₂₅H₂₄O₅ C: 74.24 H: 5.98 | n_D²⁰ 1.5621 74.11 6.09 |
| 26 | 26 | CH₃CH₂— | 4-methylphenyl sulfonyl (CH₃SO₂) | —OCH₂— (furan with CH₂-phenyl) | a | 90.1 | C₂₃H₂₄O₄S C: 69.67 H: 6.10 S: 8.09 | n_D²⁰ 1.5448 69.55 6.11 8.11 |
| 27 | 27 | CH₃CH₂— | 2,4,6-trimethylphenyl | —OCH₂—N (cyclic imide) | c | 61.2 | C₂₂H₂₇O₄N C: 71.52 H: 7.37 N: 3.79 | n_D²⁰ 1.5399 71.60 7.29 3.85 |
| 28 | 28 | CH₃—CH—CH₃ | CF₃-phenyl | —OCH₂— (furan with CH₃ and CH₂=CH) | a | 92.2 | C_{22}H_{23}O_3F_3 C: 66.66 H: 5.59 F: 15.06 | n_D²⁰ 1.5368 66.61 5.62 15.11 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 29 | 30 | $CH_2=CH-CH_2-$ | $CH_3-\overset{O}{\underset{\parallel}{C}}-\text{(p-tolyl)}$ | cyclopentenone with $CH_3$, $CH_2-CH=CH_2$, =O | a | 82.5 | $C_{22}H_{24}O_4$ C: 74.97 H: 6.86 | $n_D^{23}$ 1.5566 75.02 6.04 |
| 30 | 33 | $CH_3$-CH-$CH_3$ | $CH_3O_2C$-(furyl) | $-OCH_2$-(3-phenoxyphenyl) | e | 81.8 | $C_{24}H_{24}O_6$ C: 70.57 H: 5.92 | $n_D^{23}$ 1.5367 70.56 5.89 |
| 31 | 34 | $CH_3$-CH-$CH_3$ | $CH_3CH_2O$-(p-tolyl) | $-OCH_2$-(3-cyanophenyl) | a | 92.5 | $C_{27}H_{27}O_4N$ C: 75.50 H: 6.34 N: 3.26 | $n_D^{23}$ 1.5208 75.19 6.30 3.31 |
| 32 | 35 | $CH_3$-CH-$CH_3$ | $CH_3S$-(p-tolyl) | $-OCH_2$-(5-benzylfuryl) | a | 95.3 | $C_{24}H_{26}O_3S$ C: 73.06 H: 6.64 S: 8.13 | $n_D^{23}$ 1.5335 73.10 6.64 8.15 |
| 33 | 37 | $CH_3$-CH-$CH_3$ | methylenedioxytolyl | $-OCH$-(furyl)-$C\equiv CH$, $CH_2C\equiv CH$ | a | 73.6 | $C_{22}H_{20}O_5$ C: 72.51 H: 5.53 | $n_D^{23}$ 1.5236 72.55 5.61 |
| 34 | 36 | $CH_3$-CH-$CH_3$ | tetrahydronaphthyl-methyl | $-CH_2$-(phenyl) | d | 86.2 | $C_{27}H_{30}O_3$ C: 80.56 H: 7.51 | 80.61 7.46 |
| 35 | 45 | $CH_3CH_2-$ | $CH\equiv C-CH_2-$(p-tolyl) | $-OCH_2$-(3-phenoxyphenyl) | e | 78.1 | $C_{26}H_{24}O_3$ C: 81.22 H: 6.29 | 81.20 6.31 |
| 36 | 48 | $CH_3$-CH-$CH_3$ | $CH_3CH_2OCH_2$-(p-tolyl) | $-OCH_2$-(phthalimido) | a | 92.7 | $C_{23}H_{24}O_3$ C: 69.85 H: 6.37 N: 3.54 | $n_D^{23}$ 1.5221 69.78 6.39 3.55 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 37 | 49 | $CH_3-CH-CH_3$ | 4-($CCl=CH_2$)-phenyl | $-OCH_2$-(2,6-di-$CH_3$-4-$CH_2CH=CH_2$-phenyl) | a | 91.2 | $C_{23}H_{29}O_2Cl$ C:75.64 H: 7.36 Cl: 8.93 | $n_D^{20}$ 1.5413 75.66 7.39 8.87 |
| 38 | 51 | $CH_3-CH-CH_3$ | 4-$CH_3O$-phenyl | $-OCH_2$-(5-$CH_2C\equiv CH$-furyl) | a | 84.6 | $C_{22}H_{22}O_4$ C:75.41 H: 6.33 | $n_D^{20}$ 1.5253 75.40 6.22 |
| 39 | 52 | $CH_3-CH_2-$ | 4-$CH_3$-phenyl | $-OCH_2$-(5-$CH_2C\equiv CH$-thienyl) | a | 81.2 | $C_{22}H_{26}O_3S$ C:71.71 H: 6.56 S: 8.70 | $n_D^{20}$ 1.5549 71.80 6.59 8.78 |
| 40 | 55 | $CH_2=CH-CH_2-$ | 4-$CH_3O$-phenyl (with $CH_3$, $CH_3$, C=O) | $-OCH_2$-(N-phthalimido-thio) | a | 86.9 | $C_{22}H_{23}O_5NS$ C:64.21 H: 5.15 N: 3.40 S: 7.79 | $n_D^{19}$ 1.5350 64.30 5.19 3.29 7.72 |
| 41 | 56 | $CH_3-CH-CH_3$ | 3-$CH_3O$-phenyl | $-OCH_2$-(5-(2-thienyl)-furyl) | c | 72.1 | $C_{23}H_{26}O_3S$ C:66.64 H: 6.32 S: 7.14 | $n_D^{22}$ 1.5324 66.57 6.40 7.71 |
| 42 | 67 | $CH_3-CH-CH_3$ | 2-$CH_3$-4-$CH_3O$-phenyl | $-O-$(2-$CH_3$-3-$CH_2C\equiv CH$-4-oxo-cyclopentenyl) | a | 93.7 | $C_{21}H_{26}O_4$ C:74.09 H: 7.11 | $n_D^{20}$ 1.5628 74.06 7.22 |
| 43 | 61 | $CH_3-CH-CH_3$ | phenyl-$OCH_3$ | $-OCH_2$-(5-phenoxy-furyl) | a | 93.2 | $C_{24}H_{26}O_5$ C:73.07 H: 6.64 | $n_D^{23}$ 1.5501 73.11 6.57 |
| 44 | 69 | $CH_3CH_2-$ | phenyl | $-O-CH(C\equiv CH)-$(3-$CF_3$-phenyl) | b | 78.9 | $C_{21}H_{19}O_3F_3$ C:67.01 H: 5.09 F: 15.15 | $n_D^{25}$ 1.5119 66.95 5.14 15.20 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 45 | 81 | (CH₃)₂CH— | 3-CH₃O-C₆H₄ | —OCH₂-(5-benzyl-furan-2-yl) | d | 84.8 | C₂₄H₂₆O₄ C: 76.16 H: 6.93 | $n_D^{16}$ 1.5411 76.22 6.94 |
| 46 | 87 | (CH₃)₂CH— | 3-CH₃O-C₆H₄ | —OCH₂-(3-phenoxyphenyl) | d | 86.4 | C₂₅H₂₆O₄ C: 76.90 H: 6.71 | $n_D^{17}$ 1.5377 76.85 6.76 |
| 47 | 93 | CH₃CH₂— | 3-CH₃O-C₆H₄ | —O-(2-allyl-3-methyl-4-oxocyclopent-2-enyl) | b | 83.1 | C₂₀H₂₄O₄ C: 73.14 H: 7.37 | $n_D^{19}$ 1.5211 73.19 7.30 |
| 48 | 43 | (CH₃)₂CH— | 5,6,7,8-tetrahydronaphth-1-yl | —OCH₂-(3-phenoxyphenyl) | c | 83.2 | C₂₈H₃₀O₃ C: 81.12 H: 7.30 | $n_D^{20}$ 1.5660 81.20 7.27 |
| 49 | 102 | CH₃CH₂— | 4-CH₃-C₆H₄ | —OCH₂-(5-benzyl-furan-2-yl) | a | 91 | C₂₃H₂₄O₃ C: 79.28 H: 6.94 | $n_D^{20}$ 1.5474 79.32 7.10 |
| 50 | 103 | (CH₃)₂CH— | 4-CH₃-C₆H₄ | —OCH₂-(5-benzyl-furan-2-yl) | a | 90 | C₂₄H₂₆O₃ C: 79.53 H: 7.23 | $n_D^{20}$ 1.5433 79.60 7.18 |
| 51 | 104 | CH₃CH₂— | 3-CH₃-C₆H₄ | —OCH₂-(5-benzyl-furan-2-yl) | a | 89 | C₂₃H₂₄O₃ C: 79.28 H: 6.94 | $n_D^{20}$ 1.5470 79.23 6.99 |
| 52 | 105 | (CH₃)₂CH— | 3-CH₃-C₆H₄ | —OCH₂-(5-benzyl-furan-2-yl) | a | 93 | C₂₄H₂₆O₃ C: 79.53 H: 7.23 | $n_D^{25.5}$ 1.5430 79.50 7.30 |
| 53 | 106 | (CH₃)₂CH— | 2,4-(CH₃)₂-C₆H₃ | —OCH₂-(5-benzyl-furan-2-yl) | a | 92 | C₂₅H₂₈O₃ C: 79.75 H: 7.50 | $n_D^{25.5}$ 1.5238 79.79 7.49 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 54 | 107 | $CH_3-CH-CH_3$ | 4-Cl-C₆H₄- | -OCH₂-(2,3-dihydrobenzofuran-CH₂Ph) | a | 91 | $C_{23}H_{23}O_3Cl$ C: 72.15 H: 6.05 Cl: 9.26 | $n_D^{25.5}$ 1.5241 72.18 6.10 9.29 |
| 55 | 108 | $CH_3-CH-CH_3$ | 4-CH₃-C₆H₄- | -OCH₂-(3-phenoxyphenyl) | a | 90 | $C_{25}H_{26}O_3$ C: 80.18 H: 7.00 | $n_D^{28.5}$ 1.5596 80.21 6.92 |
| 56 | 109 | $CH_3-CH-CH_3$ | 2-CH₃-C₆H₄- | -OCH₂-(2,3-dihydrobenzofuran-CH₂Ph) | a | 94 | $C_{24}H_{26}O_3$ C: 77.53 H: 7.23 | $n_D^{26.5}$ 1.5431 79.60 7.21 |
| 57 | 110 | $CH_3CH_2-$ | 2-CH₃-C₆H₄- | -OCH₂-(2,3-dihydrobenzofuran-CH₂Ph) | a | 89 | $C_{23}H_{24}O_3$ C: 79.28 H: 6.94 | $n_D^{26.5}$ 1.5501 79.40 7.11 |
| 58 | 129 | $CH_3-CH-CH_3$ | 4-Cl-C₆H₄- | -OCH₂-(2,6-di-CH₃-4-CH₂C≡CH-C₆H₂) | b | 85 | $C_{23}H_{25}O_2Cl$ C: 74.88 H: 6.83 Cl: 9.61 | $n_D^{20}$ 1.5423 74.79 6.81 9.63 |
| 59 | 130 | $CH_3-CH-CH_3$ | 4-Cl-C₆H₄- | -OCH₂N(CO)₂C₆H₄ | c | 68 | $C_{24}H_{18}O_4NCl$ C: 64.60 H: 4.88 N: 3.77 Cl: 9.54 | $n_D^{20}$ 1.5501 64.63 4.86 3.79 9.53 |
| 60 | 131 | $CH_3-CH-CH_3$ | 4-Br-C₆H₄- | -OCH₂N(CO)₂C₆H₄ | c | 69 | $C_{24}H_{18}O_4NBr$ C: 57.70 H: 4.36 N: 3.37 Br: 19.20 | $N_D^{20}$ 1.5383 57.80 4.39 3.37 19.28 |
| 61 | 132 | $CH_3-CH-CH_3$ | 4-iPr-C₆H₄- | -OCH₂-(2,6-di-CH₃-4-CH₂C≡CH-C₆H₂) | a | 88 | $C_{26}H_{32}O_2$ C: 82.93 H: 8.57 | $n_D^{20}$ 1.5433 82.88 8.63 |
| 62 | 133 | $CH_3-CH-CH_3$ | 4-tBu-C₆H₄- | -OCH₂-C₆Cl₅ | a | 92 | $C_{22}H_{23}O_2Cl_5$ C: 53.20 H: 4.67 Cl: 35.69 | $n_D^{20}$ 1.5211 53.38 4.68 35.71 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 63 | 134 | $CH_3-\underset{CH_3}{\underset{|}{C}}-\atop{|}{CH_3}$ | 4-CH$_3$-C$_6$H$_4$- | -O-CH$_2$-C$_6$H$_4$-CH$_2$CH=CH$_2$ | a | 93 | $C_{23}H_{28}O_2$<br>C: 82.10<br>H: 8.39 | 82.19<br>8.41 |
| 64 | 135 | $CH_3-\underset{CH_3}{\underset{|}{CH}}-$ | 4-F-C$_6$H$_4$- | -O-CH$_2$-C$_6$H$_4$-CH$_2$CH=CH$_2$ | a | 89 | $C_{21}H_{23}O_2F$<br>C: 77.27<br>H: 7.10<br>F: 5.82 | 77.32<br>7.03<br>5.91 |
| 65 | 136 | $CH_3-\underset{CH_3}{\underset{|}{CH}}-$ | 4-CH$_3$-C$_6$H$_4$- | -O-CH$_2$-(benzothiazolyl) | a | 89 | $C_{21}H_{21}O_3NS$<br>C: 68.64<br>H: 5.76<br>N: 3.81<br>S: 8.73 | $n_D^{20}$ 1.5335<br>68.67<br>5.81<br>3.80<br>8.79 |
| 66 | 137 | $CH_3-\underset{CH_3}{\underset{|}{CH}}-$ | 4-OCH$_3$-C$_6$H$_4$- | -OCH$_2$-(tetrahydronaphthyl) | d | 81 | $C_{23}H_{28}O_2$<br>C: 82.10<br>H: 8.39 | $n_D^{20}$ 1.5299<br>82.15<br>8.30 |
| 67 | 138 | $CH_3-\underset{CH_3}{\underset{|}{CH}}-$ | 4-Cl-C$_6$H$_4$- | -OCH$_2$-(tetrahydronaphthyl) | d | 87 | $C_{22}H_{25}O_2Cl$<br>C: 74.04<br>H: 7.06<br>Cl: 9.94 | $n_D^{20}$ 1.5414<br>74.08<br>7.10<br>10.03 |
| 68 | 139 | $CH_3-\underset{CH_3}{\underset{|}{CH}}-$ | 4-CH$_3$-C$_6$H$_4$- | -OCH$_2$-C$_6$Cl$_5$ | b | 79 | $C_{19}H_{17}O_2Cl_5$<br>C: 50.19<br>H: 3.77<br>Cl: 39.01 | $n_D^{20}$ 1.5382<br>50.22<br>3.79<br>39.13 |
| 69 | 140 | $CH_3-\underset{CH_3}{\underset{|}{CH}}-$ | 3-F-C$_6$H$_4$- | -OCH-(2,4-diCl-C$_6$H$_3$)-C≡CH | a | 69 | $C_{20}H_{17}O_2FCl_2$<br>C: 63.34<br>H: 4.52<br>F: 5.01<br>Cl: 18.70 | $n_D^{20}$ 1.5288<br>63.39<br>4.46<br>5.08<br>18.80 |
| 70 | 141 | $CH_3-\underset{CH_3}{\underset{|}{CH}}-$ | 4-CH$_3$-C$_6$H$_4$- | -OCH-(3-CF$_3$-C$_6$H$_4$)-C≡CH | a | 78 | $C_{22}H_{20}O_2F_3$<br>C: 70.76<br>H: 5.40<br>F: 15.27 | $n_D^{20}$ 1.5385<br>70.80<br>5.39<br>15.27 |
| 71 | 142 | $CH_3-\underset{CH_3}{\underset{|}{CH}}-$ | 4-CH$_3$-C$_6$H$_4$- | -CH$_2$-(indanyl) | a | 82 | $C_{22}H_{26}O_2$<br>C: 81.95<br>H: 8.13 | $n_D^{20}$ 1.5236<br>82.06<br>8.66 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 72 | 143 | CH₃–CH–CH₃ | 4-(CH(CH₃)₂)-C₆H₄– | –CH₂–C₆H₄–CH₂CH=CH₂ | a | 80 | C₂₄H₃₀O₂<br>C: 82.24<br>H: 8.63 | nᴅ²⁰ 1.5341<br>82.19<br>8.66 |
| 73 | 144 | CH₃–CH–CH₃ | 4-Cl-C₆H₄– | –CH₂–C₆H₄–CH₂CH=CH₂ | a | 83 | C₂₁H₂₃O₂Cl<br>C: 73.56<br>H: 6.76<br>Cl: 10.34 | nᴅ²⁰ 1.5491<br>73.51<br>6.81<br>10.29 |
| 74 | 145 | CH₃–CH–CH₃ | 4-CH₃-C₆H₄– | –OCH₂-(thienyl) | b | 86 | C₂₁H₂₄O₃S<br>C: 71.71<br>H: 6.56<br>S: 8.70 | nᴅ²⁰ 1.5372<br>71.73<br>6.60<br>8.79 |
| 75 | 146 | CH₃–CH–CH₃ | 4-CH₃-C₆H₄– | –OCH₂-(furyl)-CH₃·C≡CH | a | 92 | C₂₁H₂₄O₃<br>C: 77.75<br>H: 7.46 | nᴅ²⁰ 1.5377<br>77.77<br>7.40 |
| 76 | 147 | CH₃–CH–CH₃ | 3-Cl-C₆H₄– | –OCH₂-N(COC–CH₃)=C(COC–CH₃) | a | 95 | C₁₈H₂₀O₄NCl<br>C: 61.80<br>H: 5.76<br>N: 4.01<br>Cl: 10.14 | nᴅ²⁰ 1.5469<br>61.90<br>5.73<br>4.02<br>10.19 |
| 77 | 148 | CH₃–CH–CH₃ | 4-CH₃-C₆H₄– | –OCH₂·CH=C(Cl)·CH₂–C₆H₅ | b | 87 | C₂₂H₂₅O₂Cl<br>C: 74.04<br>H: 7.06<br>Cl: 9.94 | nᴅ²⁰ 1.5471<br>74.11<br>7.92<br>9.90 |
| 78 | 149 | CH₃–CH–CH₃ | 4-Cl-C₆H₄– | –OCH₂-(2,6-(CH₃)₂-C₆H₃)-CH₂CH=CH₂ | a | 84 | C₂₃H₂₆O₂Cl<br>C: 74.68<br>H: 7.09<br>Cl: 9.59 | nᴅ²⁰ 1.5483<br>74.77<br>7.12<br>9.52 |
| 79 | 150 | CH₃–CH–CH₃ | 4-CH₃-C₆H₄– | –OCH₂-(benzothienyl) | a | 89 | C₂₁H₂₆O₂S<br>C: 73.64<br>H: 7.65<br>S: 9.36 | nᴅ²⁰ 1.5396<br>73.66<br>7.64<br>9.50 |
| 80 | 151 | CH₃–CH–CH₃ | 4-Cl-C₆H₄– | –OCH₂–C₆H₄–CH₂C≡CH | a | 95 | C₂₁H₂₁O₂Cl<br>C: 74.00<br>H: 6.21<br>Cl: 10.40 | nᴅ²⁰ 1.5611<br>74.11<br>6.23<br>10.36 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 81 | 152 | CH₃-CH-CH₃ | -C₆H₄-F | -OCH₂-N(CO)₂(cyclohexene) | c | 82 | C₂₀H₂₂O₄NF<br>C: 66.84<br>H: 6.17<br>N: 3.90<br>F: 5.29 | n_D^20 1.5229<br>66.88<br>6.18<br>4.01<br>5.30 |
| 82 | 153 | CH₃-CH-CH₃ | -C₆H₄-CH₃ | -OCH₂-(2-methyl-4-oxo-3-allyl-cyclopentenyl) | b | 80 | C₂₃H₂₆O₃<br>C: 77.27<br>H: 8.03 | n_D^20 1.5387<br>77.20<br>8.09 |
| 83 | 154 | CH₃-CH-CH₃ | -C₆H₄-F | -OCH₂-(2-methyl-4-oxo-3-propargyl-cyclopentenyl) | a | 89 | C₂₃H₂₁O₃F<br>C: 73.15<br>H: 6.45<br>F: 5.79 | n_D^20 1.5316<br>73.19<br>6.50<br>5.81 |
| 84 | 155 | CH₃-CH-CH₃ | -C₆H₄-CH₃ | -OCH₂-(3-oxo-cyclopentenyl-benzyl) | a | 93 | C₂₃H₂₆O₃<br>C: 79.53<br>H: 7.23 | n_D^20 1.5452<br>79.55<br>7.33 |
| 85 | 156 | CH₃-CH-CH₃ | -C₆H₄-Cl | -OCH₂-(3-oxo-cyclopentenyl-benzyl) | a | 92 | C₂₃H₂₃O₃Cl<br>C: 72.15<br>H: 6.05<br>Cl: 9.26 | n_D^20 1.5448<br>72.18<br>6.00<br>9.32 |
| 86 | 157 | CH₃-CH-CH₃ | -C₆H₄-I | -OCH₂-(furyl) | a | 92 | C₂₃H₂₃O₃I<br>C: 58.24<br>H: 4.89<br>I: 26.76 | n_D^20 1.5352<br>58.22<br>4.93<br>26.88 |
| 87 | 158 | CH₃-CH-CH₃ | -C₆H₄-CH₃ | -OCH₂-(thienyl) | a | 96 | C₂₄H₂₆O₂S<br>C: 76.15<br>H: 6.92<br>S: 8.47 | n_D^19 1.5311<br>76.16<br>7.03<br>8.46 |
| 88 | 159 | CH₃-CH-CH₃ | -C₆H₄-CH(CH₃)₂ | -OCH₂-(thienyl) | a | 86 | C₂₆H₃₀O₂S<br>C: 76.80<br>H: 7.44<br>S: 7.89 | n_D^19 1.5342<br>76.77<br>7.51<br>7.82 |
| 89 | 160 | CH₃-CH-CH₃ | -C₆H₄-CH₃ | -OCH-(furyl)-C≡CH, CH₂C≡CH | a | 81 | C₂₂H₂₂O₃<br>C: 79.01<br>H: 6.63 | n_D^20 1.5262<br>79.22<br>6.58 |

-continued

| Preparation Exp. No. | Comp. No. | Z | Y | OX | Esterification Method | Yield (%) | Physical Properties Calcd. (%) | Physical Properties Found (%) |
|---|---|---|---|---|---|---|---|---|
| 90 | 161 | CH₃–CH–CH₃ | –C₆H₄–C₂H₅ (p) | –OCH₂–(furan)–CH₂C≡CH with C≡CH | a | 76 | C₂₃H₂₄O₃ C: 79.28 H: 6.94 | $n_D^{20}$ 1.5291 79.33 7.10 |
| 91 | 162 | CH₃–CH–CH₃ | –C₆H₄–CH₃ (p) | –OCH₂–C₆H₄–CH=CH₂ | a | 92 | C₂₂H₂₆O₂ C: 81.95 H: 8.13 | $n_D^{20}$ 1.5366 82.00 8.18 |
| 92 | 163 | CH₃–CH–CH₃ | –C₆H₄–C(CH₃)₃ (p) | –OCH₂–C₆H₄–O–(thiophene) | a | 87 | C₂₆H₃₀O₃S C: 73.90 H: 7.16 S: 7.59 | $n_D^{20}$ 1.5361 73.92 7.17 7.63 |
| 93 | 164 | CH₃–CH–CH₃ | –C₆H₄–F (p) | –OCH₂–C₆H₄–O–(thiophene) | a | 88 | C₂₂H₂₁O₃SF C: 68.73 H: 5.51 S: 8.34 F: 4.94 | $n_D^{20}$ 1.4837 68.77 5.48 8.36 4.90 |
| 94 | 165 | CH₃–CH–CH₃ | –C₆H₄–F (p) | –OCH₂–C₆H₄–O–C₆H₄–CN | a | 88 | C₂₅H₂₂O₃NF C: 74.42 H: 5.50 N: 3.47 F: 4.71 | $n_D^{20}$ 1.5233 74.49 5.56 3.49 4.79 |
| 95 | 166 | CH₃–CH–CH₃ | –C₆H₄–Br (p) | –OCH₂–C₆H₄–O–(thiophene) | a | 92 | C₂₂H₂₁O₃SBr C: 59.33 H: 4.75 S: 7.20 Br: 17.94 | $n_D^{20}$ 1.5811 59.36 4.79 $n_D^{20}$ 1.5802 7.11 17.92 |
| 96 | 167 | CH₃–CH–CH₃ | –C₆H₄–Br (p) | –OCH₂–C₆H₄–CH₂–C₆H₅ | d | 91 | C₂₅H₂₃O₂Br C: 68.97 H: 5.32 Br: 18.36 | $n_D^{20}$ 1.5802 68.96 5.33 18.40 |
| 97 | 168 | CH₃–CH–CH₃ | –CH(CH₃)–CH₂–C₆H₄–CH₃ (p) | –OCH₂–(furan)–CH₂–C₆H₅ | a | 93 | C₂₇H₃₂O₃ C: 80.16 H: 7.97 | $n_D^{20}$ 1.5387 80.15 7.96 |
| 98 | 169 | CH₃–CH–C₂H₅ | –C₆H₄–F (p) | –OCH₂–(furan)–CH₂C≡CH | a | 79 | C₁₈H₁₇O₃F C: 71.98 H: 5.71 F: 6.33 | $n_D^{20}$ 1.5218 71.99 5.76 6.27 |
| 99 | 170 | C₂H₅– | –C₆H₄–CH₃ (p) | –OCH–(furan)–CH₂C≡CH with C≡CH | b | 82 | C₂₁H₂₀O₃ C: 78.72 H: 6.29 | $n_D^{20}$ 1.5261 78.77 6.22 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 100 | 171 | C$_2$H$_5$— | -CH(CH$_3$)-C$_6$H$_4$-CH$_3$ | -OCH$_2$-C$_6$H$_4$-O-C$_6$H$_5$ | e | 89 | C$_{26}$H$_{28}$O$_3$ C: 80.38 H: 7.27 | n$_D^{19}$ 1.5536 80.29 7.33 |
| 101 | 172 | C$_2$H$_5$— | -C$_6$H$_4$-CH$_3$ | -OCH$_2$-C$_6$H$_4$-(2-thienyl) | e | 82 | C$_{22}$H$_{22}$O$_3$S C: 72.10 H: 6.05 S: 8.75 | n$_D^{20}$ 1.5499 72.16 6.07 8.82 |
| 102 | 173 | C$_2$H$_5$— | -C$_6$H$_4$-Cl | -OCH$_2$-C$_6$H$_4$-CH$_2$CH=CH$_2$ | a | 93 | C$_{20}$H$_{21}$O$_2$Cl C: 73.05 H: 6.44 Cl:10.78 | n$_D^{20}$ 1.5236 73.09 6.46 10.69 |
| 103 | 174 | C$_2$H$_5$— | -C$_6$H$_4$-CH$_3$ | -OCH$_2$-C$_6$H$_4$-CH$_2$C≡CH | a | 92 | C$_{22}$H$_{22}$O$_2$ C: 82.32 H: 7.24 | n$_D^{20}$ 1.5252 82.40 7.26 |
| 104 | 175 | C$_2$H$_5$— | -C$_6$H$_4$-Br | -OCH$_2$-(furyl)-CH$_2$ | a | 86 | C$_{20}$H$_{19}$O$_4$Br C: 59.56 H: 4.75 Br:19.82 | n$_D^{20}$ 1.5233 59.61 4.77 20.91 |
| 105 | 176 | C$_2$H$_5$— | -C$_6$H$_4$-CH$_3$ | -OCH$_2$-C$_6$H$_4$-O-C$_6$H$_5$ | e | 92 | C$_{24}$H$_{24}$O$_3$ C: 79.97 H: 6.71 | n$_D^{20}$ 1.5711 80.05 6.77 |
| 106 | 177 | C$_2$H$_5$— | -C$_6$H$_4$-Cl | -OCH$_2$-C$_6$H$_4$-O-C$_6$H$_5$ | e | 96 | C$_{23}$H$_{21}$O$_3$Cl C: 72.53 H: 5.56 Cl: 9.31 | n$_D^{21.5}$ 1.5732 72.51 5.46 9.33 |
| 107 | 178 | C$_2$H$_5$— | -C$_6$H$_4$-Br | -OCH$_2$-C$_6$H$_4$-O-C$_6$H$_5$ | e | 89 | C$_{23}$H$_{21}$O$_3$Br C: 64.95 H: 4.98 Br:18.79 | n$_D^{20}$ 1.5861 64.92 4.86 18.82 |
| 108 | 179 | C$_2$H$_5$— | -C$_6$H$_4$-I | -OCH$_2$-(furyl)-CH$_3$ | a | 82 | C$_{21}$H$_{23}$O$_3$I C: 58.24 H: 4.89 I: 26.76 | n$_D^{20}$ 1.5733 58.25 4.92 28.81 |
| 109 | 108 | C$_2$H$_5$— | -C$_6$H$_4$-Cl | -OCH$_2$-(furyl)-C$_6$H$_5$ | b | 76 | C$_{21}$H$_{19}$O$_4$Cl C: 68.01 H: 5.16 Cl: 9.56 | n$_{D20}$ 1.5625 66.06 5.22 9.62 |
| 110 | 181 | CH$_3$— | -C$_6$H$_4$-CH$_3$ | -OCH$_2$-(furyl)-C$_6$H$_5$ | a | 90 | C$_{22}$H$_{22}$O$_3$ C: 79.01 Cl: 6.63 | n$_D^{20}$ 1.5471 79.07 6.58 |
| 111 | 182 | CH$_3$— | -C$_6$H$_4$-Cl | -OCH$_2$-(furyl)-C$_6$H$_5$ | a | 91 | C$_{21}$H$_{19}$O$_3$Cl C: 71.08 H: 5.40 Cl: 9.99 | n$_D^{20}$ 1.5518 71.11 5.32 9.89 |
| 112 | 183 | CH$_3$— | -C$_6$H$_4$-CH$_3$ | -OCH$_2$-C$_6$H$_4$-O-C$_6$H$_5$ | e | 87 | C$_{23}$H$_{22}$O$_3$ C: 79.74 H: 6.40 | n$_D^{20}$ 1.5592 79.77 6.36 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 113 | 184 | $C_2H_5-$ | 4-Cl-C₆H₄ | $-OCH_2$-(furyl)-CH₂-C₆H₅ | a | 88 | $C_{22}H_{23}O_3Cl$ C: 71.63 H: 5.74 Cl: 9.61 | $n_D^{20}$ 1.5549 71.66 5.81 9.70 |
| 114 | 185 | $C_2H_5-$ | 4-F-C₆H₄ | $-OCH_2$-(furyl)-CH₂-C₆H₅ | a | 87 | $C_{22}H_{23}O_3F$ C: 74.98 H: 6.00 F: 5.39 | $n_D^{20}$ 1.4437 75.03 6.02 5.29 |
| 115 | 186 | $C_2H_5-$ | 3-F-C₆H₄ | $-OCH_2$-(furyl)-CH₂-C₆H₅ | a | 83 | $C_{22}H_{23}O_3SF$ C: 71.71 H: 5.75 S: 8.70 F: 5.16 | $n_D^{20}$ 1.4933 71.77 5.76 8.81 5.13 |
| 116 | 187 | $C_2H_5-$ | 4-Cl-C₆H₄ | $-OCH_2$-N(CO)₂-cyclohexenyl | e | 76 | $C_{19}H_{20}O_4NCl$ C: 63.07 H: 5.57 N: 3.87 Cl: 9.80 | $n_D^{20}$ 1.5316 62.98 5.54 3.92 9.69 |
| 117 | 188 | $C_2H_5-$ | 4-CH₃-C₆H₄ | cyclopentenone-CH₂CH=CH₂ | a | 83 | $C_{22}H_{24}O_3$ C: 76.89 H: 7.74 | $n_D^{20}$ 1.5224 76.79 7.81 |
| 118 | 189 | $C_2H_5-$ | 4-CH₃-C₆H₄ | cyclopentenone-CH₂C≡CH | a | 80 | $C_{20}H_{22}O_3$ C: 77.39 H: 7.14 | $n_D^{20}$ 1.5456 77.44 7.14 |
| 119 | 190 | $C_2H_5-$ | 4-Cl-C₆H₄ | cyclopentenone-CH₂C≡CH | a | 82 | $C_{19}H_{19}O_3Cl$ C: 68.98 H: 5.79 Cl: 10.72 | $n_D^{20}$ 1.5445 68.92 5.78 10.85 |
| 120 | 191 | $C_2H_5-$ | 4-F-C₆H₄ | cyclopentenone-CH₂-C₆H₅ | a | 90 | $C_{22}H_{21}O_3F$ C: 74.98 H: 6.01 F: 5.39 | $n_D^{20}$ 1.5267 74.87 6.02 5.41 |
| 121 | 192 | $C_2H_5-$ | 3-Cl-C₆H₄ | cyclopentenone-CH₂-C₆H₅ | a | 92 | $C_{22}H_{21}O_3Cl$ C: 71.63 H: 5.74 Cl: 9.61 | $n_D^{20}$ 1.5352 71.66 5.78 9.62 |
| 122 | 193 | $(CH_3)_2CH-$ | 4-CH₃-C₆H₄ | $-OCH_2$-(furyl)-CH₂ | a | 90 | $C_{22}H_{24}O_4$ C: 74.97 H: 6.86 | $N_D^{20}$ 1.5377 75.10 6.86 |
| 123 | 194 | $(CH_3)_2CH-$ | 4-Cl-C₆H₄ | $-OCH_2$-(furyl)-CH₂ | a | 91 | $C_{21}H_{21}O_4Cl$ C: 67.65 H: 5.68 Cl: 9.51 | $n_D^{20}$ 1.5421 67.62 5.72 9.61 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 124 | 195 | CH₃–CH–CH₃ | 4-CH₃-C₆H₄ | –OCH₂-(furan-2-yl)-OC₆H₅ | a | 89 | C₂₃H₂₄O₄ C: 75.80 H: 6.64 | n_D²⁰ 1.5235 75.83 6.70 |
| 125 | 196 | CH₃–CH–CH₃ | 3-Cl-C₆H₄ | –OCH₂-(thiophen-2-yl)-CH₂-C₆H₅ | a | 91 | C₂₁H₂₃O₂SCl C: 69.24 H: 5.81 S: 8.04 Cl: 8.89 | n_D²⁰ 1.5551 69.26 5.84 8.11 8.92 |
| 126 | 197 | CH₃–CH–CH₃ | 4-Br-C₆H₄ | –OCH₂-(furan-2-yl)-CH(CH₃)-C₆H₅ | a | 88 | C₂₄H₂₅O₃Br C: 65.31 H: 5.71 Br: 18.11 | n_D²⁰ 1.5349 65.33 5.83 18.20 |
| 127 | 198 | CH₃–CH–CH₃ | 3-F-C₆H₄ | –OCH₂-(tetrahydropyran) | a | 92 | C₂₀H₂₃O₃F C: 72.70 H: 7.02 F: 5.75 | n_D²⁰ 1.5466 72.69 7.11 5.72 |
| 128 | 199 | CH₃–CH–CH₃ | 4-Cl-C₆H₄ | –OCH₂-(furan-2-yl)-CH₂C≡CH | a | 80 | C₁₉H₁₉O₃Cl C: 68.98 H: 5.79 Cl: 10.72 | n_D²⁰ 1.5238 69.01 5.72 10.77 |
| 129 | 200 | CH₃–CH–CH₃ | 4-CH₃-C₆H₄ | –OCH(C≡CH)-(furan-2-yl)-CH₂C≡CH | a | 82 | C₂₀H₂₂O₃ C: 79.01 H: 6.63 | n_D²⁰ 1.5265 79.10 6.58 |
| 130 | 201 | CH₃–CH–CH₃ | 4-Cl-C₆H₄ | –OCH(C≡CH)-(furan-2-yl)-CH₂C≡CH | a | 79 | C₂₁H₁₉O₃Cl C: 71.08 H: 5.40 Cl: 9.99 | n_D²⁰ 1.5233 71.00 5.46 9.89 |
| 131 | 202 | CH₃–CH–CH₃ | 4-F-C₆H₄ | –OCH(C≡CH)-(furan-2-yl)-CH₂C≡CH | a | 75 | C₂₁H₁₉O₃F C: 74.54 H: 5.66 F: 5.62 | n_D²⁰ 1.5249 74.53 5.77 5.66 |
| 132 | 203 | CH₃–CH–CH₃ | 4-Br-C₆H₄ | –OCH(C≡CH)-(furan-2-yl)-CH₂C≡CH | a | 83 | C₂₁H₁₉O₃Br C: 63.17 H: 4.80 Br: 20.02 | n_D²⁰ 1.5289 63.18 4.79 20.04 |
| 133 | 204 | CH₃–CH–CH₃ | 3-Cl-C₆H₄ | –OCH₂-(furan-2-yl)-CH₂-C₆H₅ | a | 90 | C₂₁H₂₃O₃Cl C: 72.15 H: 6.05 Cl: 9.26 | n_D²⁰ 1.5521 72.16 6.11 9.39 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 134 | 205 | (CH₃)₂CH— | 2-Cl-C₆H₄ | —OCH₂-(furan)-CH₂-C₆H₅ | a | 89 | $C_{23}H_{23}O_3Cl$ C: 72.15 H: 6.05 Cl: 9.26 | $n_D^{20}$ 1.5576 72.14 6.09 9.31 |
| 135 | 206 | (CH₃)₂CH— | 4-Cl-C₆H₄ | —OCH₂-C₆H₄-O-C₆H₅ | d | 83 | $C_{24}H_{23}O_3Cl$ C: 72.99 H: 5.87 Cl: 8.98 | $n_D^{20}$ 1.5655 73.04 5.87 8.99 |
| 136 | 207 | (CH₃)₂CH— | 3-Cl-C₆H₄ | —OCH₂-C₆H₄-O-C₆H₅ | e | 92 | $C_{24}H_{23}O_3Cl$ C: 72.99 H: 5.87 Cl: 8.98 | $n_D^{20}$ 1.5722 72.93 5.89 9.00 |
| 137 | 208 | (CH₃)₂CH— | 4-F-C₆H₄ | —OCH₂-(furan)-CH₂-C₆H₅ | d | 84 | $C_{23}H_{23}O_3F$ C: 75.39 H: 6.33 F: 5.19 | $n_D^{20}$ 1.4637 75.42 6.31 5.22 |
| 138 | 209 | (CH₃)₂CH— | 3-F-C₆H₄ | —OCH₂-(furan)-CH₂-C₆H₅ | a | 92 | $C_{23}H_{23}O_3F$ C: 75.39 H: 6.33 F: 5.19 | $n_D^{20}$ 1.5330 75.44 6.26 5.14 |
| 139 | 210 | (CH₃)₂CH— | 4-F-C₆H₄ | —OCH₂-C₆H₄-O-C₆H₅ | d | 93 | $C_{24}H_{23}O_3F$ C: 76.17 H: 6.13 F: 5.02 | $n_D^{20}$ 1.5544 76.20 6.14 5.10 |
| 140 | 211 | (CH₃)₂CH— | 3-F-C₆H₄ | —OCH₂-C₆H₄-O-C₆H₅ | e | 92 | $C_{24}H_{23}O_3F$ C: 76.17 H: 6.13 F: 5.02 | $n_D^{25}$ 1.5543 76.15 6.13 5.11 |
| 141 | 212 | (CH₃)₂CH— | 4-Br-C₆H₄ | —OCH₂-(furan)-CH₂-C₆H₅ | a | 89 | $C_{23}H_{23}O_3Br$ C: 64.64 H: 5.42 Br: 18.70 | $n_D^{25}$ 1.5651 64.58 5.44 18.96 |
| 142 | 213 | (CH₃)₂CH— | 4-Br-C₆H₄ | —OCH₂-C₆H₄-O-C₆H₅ | e | 91 | $C_{24}H_{23}O_3Br$ C: 65.61 H: 5.28 Br: 18.19 | $n_D^{25}$ 1.5802 65.62 5.30 18.23 |
| 143 | 214 | (CH₃)₂CH— | 4-C₂H₅-C₆H₄ | —OCH₂-(furan)-CH₂-C₆H₅ | a | 82 | $C_{25}H_{28}O_3$ C: 79.75 H: 7.50 | $n_D^{18.5}$ 1.5347 79.81 7.51 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 144 | 215 | CH₃—CH— CH₃ | –C₆H₄–C₂H₅ | –OCH₂–C₆H₄–O–C₆H₅ | a | 94 | C₂₆H₂₈O₃ C: 80.38 H: 7.27 | n_D^25 1.5590 |
| 145 | 216 | CH₃—CH— CH₃ | –C₆H₄–(n)C₃H₇ | –OCH₂–(furan)–CH₂–C₆H₅ | a | 92 | C₂₆H₃₀O₃ C: 79.96 H: 7.74 | n_D^19 1.5387 80.01 7.70 |
| 146 | 217 | CH₃—CH— CH₃ | –C₆H₄–(n)C₃H₇ | –OCH₂–C₆H₄–O–C₆H₅ | a | 90 | C₂₇H₃₀O₃ C: 80.56 H: 7.51 | n_D^19 1.5542 80.52 7.52 |
| 147 | 218 | CH₃—CH— CH₃ | –C₆H₄–(i)C₃H₇ | –OCH₂–(furan)–CH₂–C₆H₅ | a | 92 | C₂₆H₃₀O₃ C: 79.96 H: 7.74 | n_D^20 1.5385 79.94 7.83 |
| 148 | 219 | CH₃—CH— CH₃ | –C₆H₄–(i)C₃H₇ | –OCH₂–C₆H₄–O–C₆H₅ | a | 93 | C₂₇H₃₀O₃ C: 80.56 H: 7.51 | n_D^19 1.5548 80.58 7.53 |
| 149 | 220 | CH₃—CH— CH₃ | –C₆H₄–C(CH₃)₃ | –OCH₂–C₆H₄–O–C₆H₅ | a | 90 | C₂₇H₃₂O₃ C: 80.16 H: 7.97 | n_D^19 1.5302 80.21 8.04 |
| 150 | 221 | CH₃—CH— CH₃ | –C₆H₄–CH₂CH(CH₃)₂ | –OCH₂–C₆H₄–O–C₆H₅ | a | 94 | C₂₈H₃₂O₃ C: 80.73 H: 7.74 | n_D^20 1.5327 80.67 7.71 |
| 151 | 222 | CH₃—CH— CH₃ | –C₆H₄–Cl | –OCH₂–(thiophene)–CH₂–C₆H₅ | a | 82 | C₂₁H₂₁O₃SCl C: 64.85 H: 5.44 S: 8.25 Cl: 9.12 | n_D^20 1.5377 64.88 5.42 8.26 9.13 |
| 152 | 233 | CH₃—CH— CH₃ | –C₆H₄–F | –OCH₂–(thiophene)–O–C₆H₅ | a | 77 | C₂₂H₂₁O₃SF C: 68.73 H: 5.51 S: 8.34 F: 4.94 | n_D^19 1.5467 68.70 5.59 8.32 4.92 |
| 153 | 224 | CH₃—CH— CH₃ | –C₆H₄–CH₃ | –OCH₂–(thiophene)–O–C₆H₅ | a | 86 | C₂₃H₂₄O₃S C: 72.60 H: 6.36 S: 8.43 | n_D^20 1.5366 72.54 6.33 8.50 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 154 | 225 | CH₃-CH-CH₃ | 4-CH₃-C₆H₄ | -OCH₂-C₆H₄-CH₂-C₆H₅ | a | 81 | C₂₆H₃₈O₂ C: 81.62 H: 10.01 | n_D^20 1.5235 81.66 10.03 |
| 156 | 227 | CH₃-CH-CH₃ | 4-CH₃-C₆H₄ | -OCH(CN)-C₆H₄-O-C₆H₅ | a | 72 | C₂₆H₂₅O₃N C: 78.17 H: 6.31 N: 3.51 | n_D^19 1.5624 78.19 6.28 3.61 |
| 157 | 228 | CH₃-CH-CH₃ | 4-Cl-C₆H₄ | -OCH₂-C₆H₄-O-(2-thienyl) | a | 83 | C₂₂H₂₁O₃SCl C: 65.90 H: 5.28 S: 8.00 Cl: 8.84 | n_D^19 1.5433 65.99 5.27 8.04 8.82 |
| 158 | 229 | CH₃-CH-CH₃ | 3-Cl-C₆H₄ | -OCH₂-C₆H₄-O-(2-thienyl) | a | 85 | C₂₂H₂₁O₃SCl C: 65.90 H: 5.28 S: 8.00 Cl: 8.84 | n_D^19 1.5436 65.91 5.29 8.16 8.83 |
| 159 | 230 | CH₃-CH-CH₃ | 4-Cl-C₆H₄ | -OCH₂-C₆H₄-CH₂-C₆H₅ | a | 90 | C₂₅H₂₅O₂Cl C: 76.42 H: 6.41 Cl: 9.02 | n_D^20 1.5329 76.44 6.43 9.09 |
| 160 | 231 | CH₃-CH-CH₃ | 4-Cl-C₆H₄ | -OCH(CN)-C₆H₄-O-C₆H₅ | a | 74 | C₂₅H₂₂O₃NCl C: 71.51 H: 5.28 N: 3.34 Cl: 8.44 | m.p. 1.5533 71.54 5.30 3.31 8.46 |
| 161 | 232 | CH₃-CH-CH₃ | 4-C₂H₅-C₆H₄ | -OCH(CN)-C₆H₄-O-C₆H₅ | a | 75 | C₂₇H₂₇O₃N C: 78.42 H: 6.58 N: 3.39 | n_D^20 1.5239 78.44 6.61 3.44 |
| 162 | 233 | CH₃-CH-CH₃ | 4-(i)C₃H₇-C₆H₄ | -OCH₂-C₆H₄-O-(2-thienyl) | a | 86 | C₂₅H₂₈O₃S C: 73.49 H: 6.91 S: 7.85 | n_D^20 1.5567 73.51 6.94 7.86 |
| 163 | 234 | CH₃-CH-CH₃ | 4-(i)C₃H₇-C₆H₄ | -OCH₂-C₆H₄-CH₂-C₆H₅ | a | 89 | C₂₈H₃₂O₂ C: 83.96 H: 8.05 | n_D^20 1.5341 83.99 8.06 |
| 164 | 235 | CH₃-CH-CH₃ | 4-(i)C₃H₇-C₆H₄ | -OCH(CN)-C₆H₄-O-C₆H₅ | a | 80 | C₂₈H₂₉O₃N C: 78.66 H: 6.84 N: 3.28 | n_D^20 1.5226 78.67 6.90 3.11 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 165 | 236 | $CH_3{>}CH-$ $CH_3$ | 4-(2-methyl-2-propyl)phenyl | $-OCH(C_6H_4-O-C_6H_5)-CN$ (m-phenoxyphenyl-cyanomethyl) | a | 79 | $C_{29}H_{31}O_3N$ C: 78.88 H: 7.08 N: 3.17 | $n_D^{20}$ 1.5451 78.79 7.06 3.24 |
| 166 | 237 | $CH_3-\underset{CH_3}{\overset{CH_3}{C}}-$ | phenyl | $-OCH_2$-(2-benzylfuran) | a | 87 | $C_{24}H_{26}O_3$ C: 79.53 H: 7.23 | $n_D^{20}$ 1.5335 79.56 7.20 |
| 167 | 238 | $CH_3-\underset{CH_3}{\overset{CH_3}{C}}-$ | 4-Cl-phenyl | $-OCH_2$-(m-phenoxyphenyl) | a | 89 | $C_{25}H_{25}O_3Cl$ C: 73.43 H: 6.16 Cl: 8.67 | $n_D^{19}$ 1.5427 73.49 6.20 8.60 |
| 168 | 239 | $CH_3-\underset{CH_3}{\overset{CH_3}{C}}-$ | 4-CH_3-phenyl | $-OCH_2$-(2-benzylfuran) | a | 89 | $C_{25}H_{28}O_3$ C: 79.75 H: 7.49 | $n_D^{20}$ 1.5366 79.72 7.52 |
| 169 | 240 | $CH_3-\underset{CH_3}{\overset{CH_3}{C}}-$ | 4-CH_3-phenyl | $-OCH_2$-(m-phenoxyphenyl) | a | 91 | $C_{26}H_{28}O_3$ C: 80.38 H: 7.26 | $n_D^{21}$ 1.5225 80.33 7.24 |
| 170 | 241 | $CH_3{>}CH-$ $CH_3$ | 2-methyl-5-furyl | $-OCH_2$-(2-benzylfuran) | a | 76 | $C_{22}H_{26}O_4$ C: 74.98 H: 6.86 | $n_D^{22}$ 1.5236 75.02 6.80 |
| 171 | 242 | $CH_3{>}CH-$ $CH_3$ | 2-methyl-4-thienyl | $-OCH_2$-(2-benzylfuran) | a | 79 | | |
| 172 | 243 | $CH_3{>}CH-$ $CH_3$ | 2-methyl-5-furyl | $-OCH_2$-(m-phenoxyphenyl) | a | 79 | $C_{23}H_{26}O_3S$ C: 75.80 H: 6.64 | $n_D^{20}$ 1.5344 75.76 6.62 |
| 173 | 244 | $CH_3{>}CH-$ $CH_3$ | 2-thienyl | $-OCH_2$-(2-benzylfuran) | a | 82 | $C_{21}H_{22}O_3S$ C: 71.15 H: 6.26 S: 9.04 | $n_D^{19}$ 1.5226 71.09 6.22 9.11 |
| 174 | 245 | $CH_3-\overset{}{CH-}$ $CH_3$ | cyclopentyl | $-OCH_2$-(2-benzylfuran) | a | 89 | $C_{20}H_{26}O_3$ C: 77.37 H: 7.14 | $n_D^{28}$ 1.5293 77.29 7.16 |

| Preparation Exp. No. | Comp. No. | Z | Y | OX | Esterification Method | Yield (%) | Physical Properties Calcd. (%) | Physical Properties Found (%) |
|---|---|---|---|---|---|---|---|---|
| 175 | 246 | C₂H₅ | cyclopentenyl | —OCH₂-(furan)-CH₂-phenyl | a | 89 | C₂₁H₃₀O₃ C: 77.75 H: 7.46 | n_D^{24.5} 1.5276 77.78 7.44 |
| 176 | 247 | (CH₃)₂CH | cyclopentenyl | —OCH₂-(phenoxyphenyl) | a | 86 | C₂₃H₂₆O₃ C: 78.83 H: 7.48 | n_D^{28} 1.5483 78.81 7.40 |
| 177 | 248 | C₂H₅ | cyclopentenyl | —OCH₂-(furan)-CH₂C≡CH | a | 90 | C₁₈H₂₂O₃ C: 75.49 H: 7.74 | N_D^{24.5} 1.4965 75.53 7.69 |
| 178 | 249 | (CH₃)₂CH | cyclopentenyl | —OCH₂-(furan)-CH₂-phenyl | a | 90 | C₂₂H₂₆O₃ C: 78.07 H: 7.74 | n_D^{24.5} 1.5248 78.10 7.74 |
| 179 | 250 | (CH₃)₂CH | cyclopentenyl | —OCH₂-(3,5-dimethylphenyl)-CH₂C≡CH | a | 85 | C₂₂H₂₈O₂ C: 81.44 H: 8.70 | n_D^{25} 1.5615 81.64 8.53 |
| 180 | 251 | (CH₃)₂CH | cyclopentenyl | —OCH₂N(cyclohexene-dicarboximide) | a | 91 | C₁₉H₂₅O₄N C: 68.86 H: 7.60 N: 4.23 | n_D^{25} 1.5380 68.69 7.64 4.10 |
| 181 | 252 | (CH₃)₂CH | cyclopentenyl | —OCH₂N(dimethylmaleimide) | a | 88 | C₁₇H₂₃O₄N C: 66.86 H: 7.59 N: 4.59 | n_D^{25} 1.5237 66.97 7.50 4.45 |
| 182 | 253 | (CH₃)₂CH | cyclopentenyl | —OCH₂-(pentachlorophenyl) | a | 90 | C₁₇H₁₇O₂Cl₅ C: 47.42 H: 3.98 Cl: 41.17 | n_D^{25} 1.5395 47.88 3.70 41.53 |
| 183 | 254 | (CH₃)₂CH | cyclopentenyl | —O—CH(C≡CH)—CH₂-(furan)-CH₂C≡CH | a | 85 | C₂₀H₂₂O₃ C: 77.37 H: 7.14 | n_D^{24.5} 1.5088 77.35 7.17 |
| 184 | 255 | (CH₃)₂CH | cyclopentenyl | —OCH₂-(tetrahydronaphthyl) | a | 90 | C₂₁H₂₈O₂ C: 80.73 H: 9.03 | n_D^{25} 1.5132 80.70 8.98 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 185 | 256 | CH₃—CH—CH₃ | cyclopentenyl | —OCH₂CH=C(Cl)—CH₂—C₆H₅ | a | 89 | C₂₀H₂₅O₂Cl C: 72.16 H: 7.59 Cl: 10.65 | n_D 1.5205 72.05 7.55 10.82 |
| 186 | 257 | CH₃—CH—CH₃ | phenyl | —O—(2-allyl-cyclopentenone) CH₂CH=CH₂ | a | 86 | C₂₀H₂₈O₃ C: 75.91 H: 8.92 | n_D²⁴·⁵ 1.5085 |
| 187 | 258 | CH₃—CH—CH₃ | phenyl | —OCH₂—(2-benzyl-thiophene) | a | 90 | C₂₃H₂₈O₂S C: 74.96 H: 7.66 S: 8.70 | n_D 1.5370 |
| 188 | 259 | CH₃—CH—CH₃ | phenyl | —OCH₂—(benzothiophene) | a | 89 | C₁₉H₂₄O₂S C: 71.66 H: 8.23 S: 10.07 | n_D 1.5352 71.69 8.24 9.80 |
| 189 | 259 | CH₃—CH—CH₃ | phenyl | —OCH₂—(2-propargyl-thiophene) CH₂C≡CH | a | 92 | C₁₉H₂₄O₂S C: 72.11 H: 7.64 S: 10.13 | n_D 1.5323 72.15 7.68 10.05 |
| 190 | 261 | CH₃—CH—CH₃ | phenyl | —OCH₂—(3-cyano-phenoxyphenyl) C≡N | a | 85 | C₂₅H₂₇O₃N C: 77.09 H: 6.99 N: 3.60 | n_D 1.5486 76.93 6.92 3.52 |
| 191 | 262 | CH₃—CH—CH₃ | phenyl | —OCH.C≡CH with CH₃ and phenyl | a | 86 | C₂₃H₂₈O₂ C: 82.10 H: 8.39 | n_D 1.5213 82.15 8.39 |
| r192 | 263 | CH₃— | phenyl | —OCH₂—C₆H₅ | a | 86 | C₂₃H₂₄O₃ C: 77.75 H: 7.46 | n_D 1.5309 77.60 7.48 |
| 193 | 264 | C₂H₅— | phenyl | —OCH₂—(2-benzyl-furan) | a | 88 | C₂₂H₂₆O₃ C: 78.07 H: 7.74 | n_D 1.5308 78.12 7.61 |
| 194 | 265 | CH₃—CH—CH₃ | phenyl | —OCH₂—(3-phenoxyphenyl) | a | 86 | C₂₄H₂₈O₃ C: 79.09 H: 7.74 | n_D 1.54467 78.80 7.76 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 195 | 266 | C$_2$H$_5$— | cyclohexenyl | —OCH$_2$-(tetrahydrobenzofuran) | a | 86 | C$_{19}$H$_{26}$O$_3$ C: 75.46 H: 8.67 | n$_D^{21}$ 1.5088 75.40 8.66 |
| 196 | 267 | (CH$_3$)$_2$CH— | cyclohexenyl | —O-(2-methyl-4-oxo-3-propargyl-cyclopentenyl) | a | 90 | C$_{20}$H$_{26}$O$_3$ C: 76.40 H: 8.34 | n$_D^{24.5}$ 1.5140 76.58 8.29 |
| 197 | 268 | (CH$_3$)$_2$CH— | cyclohexenyl | —O—CH(C≡CH)—CH$_2$C≡CH (furyl) | a | 85 | C$_{22}$H$_{24}$O$_3$ C: 77.75 H: 7.46 | n$_D^{24.5}$ 1.5133 77.81 7.40 |
| 198 | 269 | (CH$_3$)$_2$CH— | cyclohexenyl | —OCH$_2$-(furyl-CH$_2$C≡CH) | a | 87 | C$_{19}$H$_{24}$O$_3$ C: 75.97 H: 8.05 | n$_D^{24.5}$ 1.5064 75.86 8.04 |
| 199 | 270 | (CH$_3$)$_2$CH— | chloro-cyclohexenyl | —OCH$_2$-(furyl-CH$_2$Ph) | a | 92 | C$_{22}$H$_{25}$O$_3$Cl C: 70.86 H: 6.76 Cl: 9.51 | n$_D^{24.5}$ 1.5358 70.66 6.73 9.30 |
| 200 | 271 | (CH$_3$)$_2$CH— | chloro-cyclohexenyl | —OCH$_2$-(thienyl-cyclohexyl) | a | 88 | C$_{19}$H$_{25}$O$_2$ClS C: 64.66 H: 7.14 Cl: 10.05 S: 9.09 | n$_D^{23}$ 1.5430 64.74 7.15 9.77 9.13 |
| 201 | 272 | (CH$_3$)$_2$CH— | methyl-cyclohexenyl | —OCH$_2$-(phenoxyphenyl) | a | 90 | C$_{23}$H$_{30}$O$_3$ C: 79.33 H: 7.99 | n$_D^{23}$ 1.5474 79.25 7.90 |
| 202 | 273 | (CH$_3$)$_2$CH— | methyl-cyclohexenyl | —O-(2-methyl-4-oxo-3-allyl-cyclopentenyl) | a | 87 | C$_{21}$H$_{30}$O$_3$ C: 76.32 H: 9.15 | n$_D^{21}$ 1.5030 76.55 9.13 |
| 203 | 274 | (CH$_3$)$_2$CH— | dimethyl-cyclohexenyl | —OCH$_2$-(furyl-CH$_2$Ph) | a | 87 | C$_{25}$H$_{30}$O$_3$ C: 79.33 H: 7.99 | n$_D^{23}$ 1.5423 79.47 7.95 |
| 204 | 275 | (CH$_3$)$_2$CH— | dimethyl-cyclopentenyl | —OCH$_2$-(furyl-CH$_2$Ph) | a | 89 | C$_{24}$H$_{28}$O$_3$ C: 79.09 H: 7.74 | n$_D^{21}$ 1.5252 79.05 7.73 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 205 | 276 | (CH₃)₂CH– | 1,2-dimethylcyclopentenyl | –O–CH(C≡N)–furan–CH₂C≡CH | a | 86 | C₂₄H₂₉NO₃ C:77.75 H:7.46 | $n_D^{20}$ 1.5097 77.62 7.49 |
| 206 | 277 | (CH₃)₂CH– | 1,2-dimethylcyclopentenyl | –O–CH(C≡N)–C₆H₄–OC₆H₅ | a | 89 | C₂₅H₂₇NO₃ C:77.09 H:6.99 N:3.60 | $n_D^{20}$ 1.5470 77.11 6.80 3.53 |
| 207 | 278 | CH₃– | 2-methyl-cyclopentenone | –OCH₂–thienyl–CH₂ | a | 89 | C₁₉H₂₀O₄S C:66.26 H:5.85 S:9.31 | $n_D^{20}$ 1.5335 66.07 5.88 9.24 |
| 208 | 279 | (CH₃)₂CH– | 2-methyl-cyclopentenone | –O–CH₂–C₆H₅ (via cyclopentenone) | a | 83 | C₂₃H₂₆O₄ C:75.38 H:7.15 | $n_D^{20}$ 1.5088 75.15 7.02 |
| 209 | 280 | (CH₃)₂CH– | 2-methyl-cyclopentenyl-O | –OCH₂–C₆H₅ | a | 87 | C₂₃H₂₆O₄ C:75.38 H:7.15 | $n_D^{20}$ 1.5075 75.36 7.18 |
| 210 | 281 | C₂H₅– | (CH₃)₂C=CH– | –OCH₂–C₆H₅ | a | 86 | C₂₀H₂₄O₃ C:76.89 H:7.74 | $n_D^{25}$ 1.5178 76.54 7.70 |
| 211 | 282 | (CH₃)₂CH– | (CH₃)₂C=CH– | –OCH₂–C₆H₅ | a | 86 | C₂₁H₂₆O₃ C:77.27 H:8.03 | $n_D^{20}$ 1.5185 77.34 8.06 |
| 212 | 283 | (CH₃)₂CH– | (CH₃)₂C=CH– | –OCH₂–C₆H₄–OC₆H₅ | a | 90 | C₂₂H₂₆O₃ C:78.07 H:7.74 | $n_D^{20}$ 1.5413 77.95 7.90 |
| 213 | 284 | (CH₃)₂CH– | (CH₃)₂C=CH– | –OCH₂–furan–CH₂C≡CH | a | 89 | C₁₇H₂₂O₃ C:74.42 H:8.08 | $n_D^{20}$ 1.4960 74.84 8.15 |

| Preparation Exp. No. | Comp. No. | Z | Y | OX | Esterification Method | Yield (%) | Physical Properties Calcd. (%) | Physical Properties Found (%) |
|---|---|---|---|---|---|---|---|---|
| 214 | 285 | CH₃–CH–CH₃ | CH₃–C=CH–, CH₃ | –O–CH(C≡N)–C₆H₄–O–C₆H₅ | a | 85 | C₂₁H₂₃O₃N C: 76.01 H: 6.93 N: 3.85 | n_D^{23.5} 1.5407 76.10 6.88 3.62 |
| 215 | 286 | CH₃– | CH₃–C=CH–CH₃, CH₃ | –OCH₂–(furan)–CH₂–C₆H₅ | a | 91 | C₁₉H₂₂O₃ C: 76.48 H: 7.43 | n_D^{24.5} 1.5202 76.41 7.55 |
| 216 | 287 | C₂H₅– | CH₃–C=CH–CH₃, CH₃ | –OCH₂–(furan)–CH₂–C₆H₅ | a | 87 | C₂₀H₂₄O₃ C: 76.89 H: 7.74 | n_D^{24.5} 1.5165 76.71 7.85 |
| 217 | 288 | CH₃–CH–CH₃ | CH₃–C=CH–CH₃, CH₃ | –OCH₂–(furan)–CH₂–C₆H₅ | a | 88 | C₂₁H₂₆O₃ C: 77.27 H: 8.03 | n_D^{23} 1.5153 77.25 8.09 |
| 218 | 289 | CH₃–CH–C₂H₅ | CH₃–C=CH–, C₂H₅ | –OCH₂–(furan)–CH₂–C₆H₅ | a | 88 | C₂₁H₂₆O₃ C: 77.27 H: 8.03 | n_D^{23} 1.5150 77.45 8.01 |
| 219 | 290 | CH₃–CH–CH₃ | CH₃–C=CH–, C₂H₅ | –OCH₂–(furan)–CH₂–C₆H₅ | a | 92 | C₂₂H₂₈O₃ C: 77.61 H: 8.29 | n_D^{23} 1.5134 77.76 8.25 |
| 220 | 291 | CH₃–CH–C₂H₅ | CH₃–C=CH–, C₂H₅ | –OCH₂–C₆H₄–O–C₆H₅ | a | 89 | C₂₃H₂₈O₃ C: 78.37 H: 8.01 | n_D^{23} 1.5363 78.43 8.08 |
| 221 | 292 | CH₂=CHCH₂– | cyclohexenyl-CH₃ | –OCH₂–(furan)–CH₂–C₆H₅ | a | 89 | C₂₃H₂₈O₃ C: 78.83 H: 7.48 | n_D^{23} 1.5345 78.85 7.48 |
| b222 | 293 | CH≡CCH₂– | cyclohexenyl-CH₃ | –OCH₂–(furan)–CH₂–C₆H₅ | a | 90 | C₂₃H₂₄O₃ C: 79.28 H: 6.94 | n_D^{23} 1.5363 79.20 7.02 |
| 223 | 294 | CH₃–CH–CH₃ | cyclohexenyl-CH₃ | –OCH₂(CH₃)–(furan)–CH₂C≡CH | a | 86 | C₂₀H₂₆O₃ C: 76.40 H: 8.34 | n_D^{23} 1.4995 76.49 8.55 |
| 224 | 295 | CH₃–CH–CH–CH₂–, CH₃ CH₃ | phenyl-CH₃ | –OCH₂–(furan)–CH₂–C₆H₅ | a | 82 | C₂₄H₂₆O₃ C: 79.53 H: 7.23 | n_D^{23} 1.5356 78.91 7.28 |

-continued

| Preparation Exp. No. | Comp. No. | Z | Y | OX | Esterification Method | Yield (%) | Physical Properties Calcd. (%) | Found (%) |
|---|---|---|---|---|---|---|---|---|
| 225 | 296 | $CH_3CH_2-$ | (phenyl) | $-OCH_2-$ (2,6-dimethyl-4-propargylphenyl) | a | 89 | $C_{22}H_{24}O_2$ C: 82.46 H: 7.55 | $n_D^{19}$ 1.5238 82.41 7.53 |
| 226 | 297 | $CH_3CH_2-$ | (phenyl) | $-OCH_2-$ (tetrahydrobenzofuran-2-yl) | a | 78 | $C_{19}H_{22}O_3$ C: 76.48 H: 7.43 | $n_D^{20}$ 1.5542 76.55 7.37 |
| 227 | 298 | $(CH_3)_2CH-$ | ($CH_3S$-phenyl) | $-CH_2-$ (3-phenoxyphenyl) | a | 84 | $C_{23}H_{26}O_3S$ C: 73.86 H: 6.45 S: 7.89 | $n_D^{20}$ 1.5587 73.92 6.40 7.81 |
| 0228 | 299 | $(CH_3)_2CH-$ | (3-methyl-2-cyclopentenon-2-yl) | $-CH_2-$ (3-phenoxyphenyl) | a | 87 | $C_{23}H_{24}O_4$ C: 75.80 H: 6.64 | $n_D^{20}$ 1.5366 75.77 6.72 |
| 229 | 300 | $(CH_3)_2CH-$ | (3-methyl-2-cyclopentenyl) | $-CH_2-$ (3-phenoxyphenyl) | a | 91 | $C_{23}H_{26}O_3$ C: 78.82 H: 7.48 | $n_D^{20}$ 1.5412 78.79 7.55 |

Additional compounds of the invention which can be prepared using methods similar to the above described are as follows:

301. 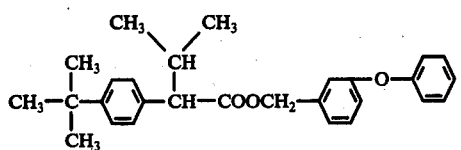
3-Phenoxybenzyl-α'-isopropyl-4'-tert.-butylphenylacetate
$n_D^{23.0}$ 1.5449

302. 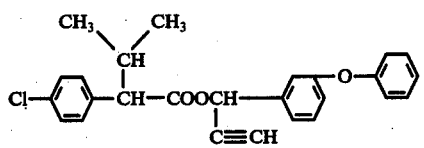
α-Ethynyl-3-phenoxybenzyl-α'-isopropyl-4'-chlorophenylacetate
$n_D^{23.0}$ 1.5699

303. 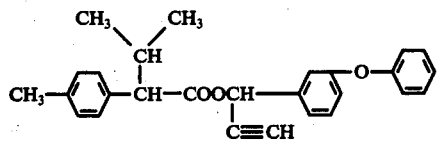
α-Ethynyl-3-phenoxybenzyl-α'-isopropyl-4-40-methylphenylacetate
$n_D^{24.0}$ 1.5611

304. 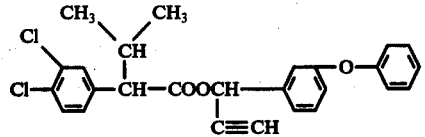
α-Ethynyl-3-phenoxybenzyl-α'-isopropyl-3',4'-dichlorophenylacetate
$n_D^{22.0}$ 1.5433

305. 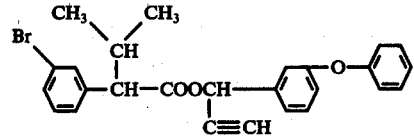
α-Ethynyl-3-phenoxybenzyl-α'-isopropyl-3'-bromophenylacetate
$n_D^{23.0}$ 1.5329

306. 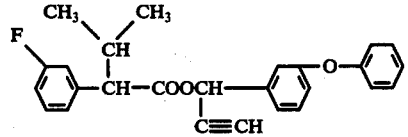
α-Ethynyl-3-phenoxybenzyl-α'-isopropyl-3'-fluorophenylacetate
$n_D^{25.0}$ 1.5625

307. 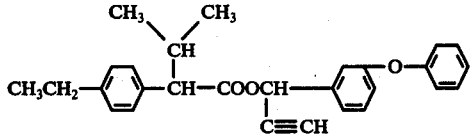
α-Ethynyl-3-phenoxybenzyl-α'-isopropyl-4'-ethylphenylacetate
$n_D^{23.5}$ 1.5723

308. 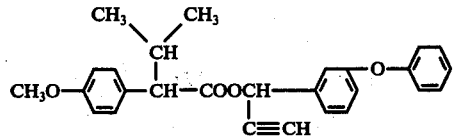
α-Ethynyl-3-phenoxybenzyl-α'-isopropyl-4'-methoxyphenylacetate
$n_D^{22.4}$ 1.5622

309. 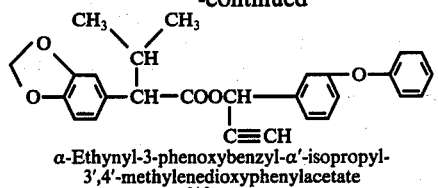
α-Ethynyl-3-phenoxybenzyl-α'-isopropyl-3',4'-methylenedioxyphenylacetate
$n_D^{24.0}$ 1.5749

310. 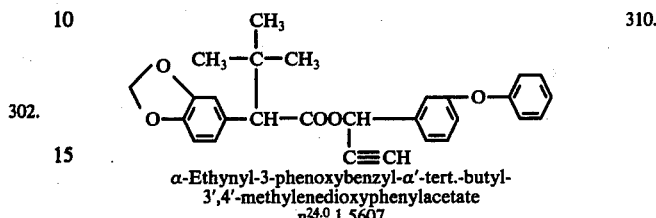
α-Ethynyl-3-phenoxybenzyl-α'-tert.-butyl-3',4'-methylenedioxyphenylacetate
$n_D^{24.0}$ 1.5607

311. 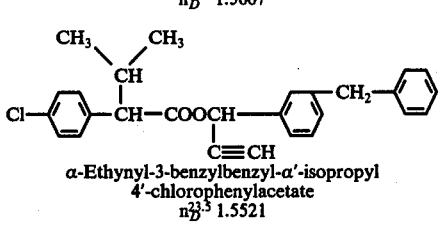
α-Ethynyl-3-benzylbenzyl-α'-isopropyl 4'-chlorophenylacetate
$n_D^{23.3}$ 1.5521

312. 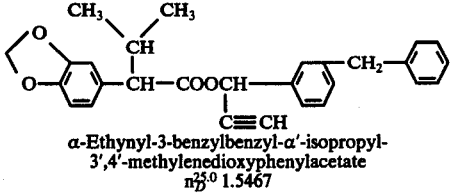
α-Ethynyl-3-benzylbenzyl-α'-isopropyl-3',4'-methylenedioxyphenylacetate
$n_D^{25.0}$ 1.5467

Most of the important intermediates of the present invention, i.e., disubstituted acetic acid, can effectively be prepared in high yields via one of the alternative procedures (A), (B) and (C) given below.

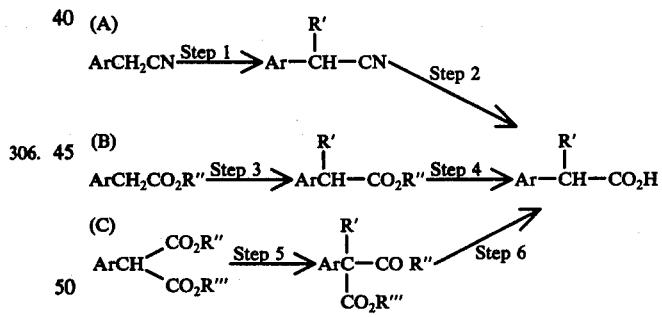

wherein Ar represents an aryl group, R' represents an alkyl, alkenyl or alkynyl group, R" represents hydrogen or a lower alkyl group, and R'" represents a lower alkyl group.

Step 1: This procedure can be accomplished by alkylating the corresponding arylacetonitrile with an appropriate halide or sulfoxylate of the formula R'—X in an inert solvent (for example, ethers, tetrahydrofuran, benzene, toluene, etc. including liquid ammonia when NaNH₂ and the like is used as a base described below) in the presence of a base such as alkali metals, alkali metal hydrides, alkali metal amides and the like at room temperature or an elevated temperature.

Step 2: This procedure can be accomplished under the well-known conditions commonly used for hydrolysis of a nitrile group, i.e., by heating the nitrile with a mineral acid or an alkaki hydroxide.

Steps 3 and 4: This procedure can be accomplished by alkylating the corresponding phenylacetic acid or a lower-alkyl ester thereof with an appropriate halide or sulfoxylate of the formula R'—X in an inert solvent in the presence of a base such as the alkali metals or hydrides thereof, n-butyl lithium and the like at room temperature or an elevated temperature, and, when the lower-alkyl ester is used for the alkylation, hydrolyzing the resulting ester with an appropriate acid or alkali in the usual manner.

Step 5: This procedure can be accomplished by reacting an arylmalonic acid ester (which is easily obtainable by carbalkoxylation of the corresponding arylacetic ester) with an appropriate halide or sulfoxylate of the formula R'—X in the presence of an alkali metal alkoxide or an alkali metal hydride as a base in an inert solvent or an alcohol corresponding to the alkali metal alkoxide.

Step 6: This procedure can be accomplished under the well-known conditions commonly used for hydrolysis of a usual ester, i.e., by hydrolyzing the ester with an acid or alkali to obtain the corresponding dicarboxylic acid followed by heat-decarbonization to obtain the desired carboxylic acid, or can be accomplished by heating the diester with an alkali metal alkoxide in an alcohol whereby the diester is easily converted into a monoester by decarboxylation and hydrolyzing the monoester by the well-known procedure to obtain the corresponding carboxylic acid in high yields.

The preparation of the intermediates, carboxylic acids, can be illustrated by the following Synthesis Examples, but they are not to be construed as limiting the processes or intermediates of the present invention.

SYNTHESIS EXAMPLE 1

α-Isopropyl-4-methoxyphenylacetonitrile 14.72 g (0.1 mole) of 4-methoxyphenylacetonitrile in 10 ml of dry toluene was added to a stirred solution of sodium hydride (2.64 g, 0.11 mole) and isopropylbromide (18.45 g, 0.15 mole) in 100 ml of dry toluene and 10 ml of dry dimethylformamide which was heated at 70° C, in 30 minutes. After addition was completed, the mixture was heated at a temperature of from 80° to 85° C for 3 hours, and cooled to room temperature then poured into 200 g of ice-water.

Organic layer was separated and the aqueous layer was extracted with ether twice. Combined organic layer was washed successively with water and saturated sodium chloride solution, and dried over anhydrous sodium sulfate. The solvent was removed in vacuo and the residual oil was distilled in vacuo to afford 15.70 g (b.p. 95° – 96°/0.15 mmHg, 83.0%) of α-isopropyl-4-methoxyphenylacetonitrile.

In similar manners, the following α-isopropylphenylacetonitriles were obtained.

|  |  |  | b.p.° C/mmHg | Yield (%) |
|---|---|---|---|---|
| 4-bromo-α-isopropylphenyl-acetonitrile |  | 1) | 90 – 93°/0.10 | 82.1 |
| 4-ethyl-d- | " | 2) | 96 – 93°/0.10 | 85.1 |
| 4-isopropyl-α- | " | 3) | 100 – 102°/0.40 | 83.5 |
| 3-chloro-α- | " | 4) | 104 – 106°/0.30 | 80.2 |
| 4-fluoro-α- | " | 5) | 89 – 90°/5.0 | 80.7 |
| 3-fluoro-α- | " | 6) | 89 – 90°/5.0 | 81.1 |
| 4-thiomethyl-α- | " | 7) | 105°/0.10 | 75.1 |
| 2,4,6-trimethyl-α- | " | 8) | 87 – 88°/0.20 | 53.1 |
| 3-trifluoromethyl-α- | " | 9) | 95 – 96°/5.0 | 87.9 |
| 3,4-methylenedioxy-α- | " | 10) | 95 – 100°/0.2 | 78.2 |
| 3-phenoxy-α- | " | 11) | 147 – 148°/0.3 | 85.2 |

1) Starting 4-bromophenylacetonitrile was synthesized from 4-bromotoluene which was brominated at 180° C with bromine and converted into the nitrile with potassium cyanide in DMSO-H₂O.
2) Ethylbenzene was chloromethylated using the Kosolopoff method (JACS, 68, 1670 (1946)) and the chloride was purified by fractional distillation, then converted into the nitrile in a similar manner described above.
3) Isopropylbenzene was chloromethylated and converted into the nitrile.
4) Commercially available 3-chlorobenzylchloride was converted into the nitrile similarly.
5, 6) 3-fluorotoluene and 4-fluorotoluene were brominated with NBS in carbon tetrachloride then converted into the nitriles.
7) Thioanisole was chloromethylated with paraformaldehyde and zinc chloride in poor conversion, then converted into the nitrile.
8) Mesitylene was chloromethylated and converted into the nitrile. In this case, alkylation proceeded very slowly even though an elevated temperature (110° C) and longer reaction times (15 hours) were tried.
9) 3-bromobenzotrifluoride was converted to 3-hydroxymethylbenzotrifluoride via a Grignard method (R. Filler and H. Novar, J.O.C., 25, 733 (1960)) and converted into a bromide (HBr-H₂SO₄) and a nitrile (KCN-DMSO), successively.
10) Piperonyl alcohol was converted into a chloride with thionyl chloride at 0° C, followed by KCN/DMSO to afford the nitrile.
11) m-phenoxytoluene which was obtained from m-cresol and bromotoluene was brominated at 230° C with bromine, and the corresponding bromide was converted into the nitrile similarly.

SYNTHESIS EXAMPLE 2

4-Bromo-α-isopropyl-phenylacetic acid 20 g of 4-bromo-α-isopropylphenylacetonitrile was heated with 140 ml of sulfuric acid (50 V/V %) at 145° C for 6 hours. The cooled reaction mixture was poured onto 150 g of ice, and extracted with ether (100 ml × 3). The ether layers were combined and extracted with three 70 ml portions of cold 5% sodium hydroxide solution, and the aqueous extracts were acidified with concentrated hydrochloric acid, and then extracted with ether. The ether extract was washed successively with water, saturated sodium chloride solution, dried over anhydrous sodium sulfate. Removal of the solvent gave 16.9 g (78.2%) of white crystals, which were sufficiently pure for use in next step. A portion of the crystals was recrystallized from benzene, melting point: 97° - 98° C.

SYNTHESIS EXAMPLE 3

4-Methoxy-α-isopropylphenylacetic acid 12.8 g of 4-methoxy-α-isopropylphenylacetonitrile was heated under reflux (140° C) with 200 ml of ethylene-glycol and 40 g of 50% aqueous potassium hydroxide solution for 8 hours. The cooled reaction mixture was poured into 200 g of ice-water, which was washed with ether. The aqueous layer was acidified with concentrated hydrochloric acid, and extracted with ether (150 ml × 3). The combined ether extract was washed successively with water, saturated sodium chloride, then dried over anhydrous sodium sulfate. Removal of the solvent gave 11.30 g (80.4%) of white crystals. The acid recrystallized from benzene melted at 146° - 148° C.

In similar manners the following acids were prepared.

| | Method of Hydrolysis | Yields | N.M.R. signals (CHCl$_3$, in ppm) |
|---|---|---|---|
| 3-trifluoromethyl-α-isopropyl-phenyl-acetic acid | A | 25.0 | 0.74 (3H, d.J=7Hz), 1.07 (3H, d.J=7Hz), 1.9 - 2.6 (1H, m.), 3.22 (1H, d.J=10Hz), 7.4 - 7.7 (4H, m.), 10.6 (1H, b.S) |
| 4-fluoro-α-isopropyl-phenylacetic acid | A | 85.2 | 0.69 (3H, d.J=7Hz), 1.05 (3H, d.J=7Hz), 1.9 - 2.6 (1H, m.) 3.10 (1H, d.J=12Hz), 6.9 - 7.4 (4H, m.), 9.70 (1H, b.S.) |
| 4-thiomethyl-α-isopropyl-phenyl-acetic acid | B | 78.2 | 0.69 (3H, d.J=6.5Hz), 1.07(3H, d.J=6.5Hz), 2.42 (3H, S), 3.07 (1H, d.J=10Hz), 7.19 (4H, S.), 9.64 (1H, b.S.) |
| 2,4,6-trimethyl-α-isopropyl-phenyl-acetic acid | A | 34.5 | 0.61 (3H, d.J=7Hz), 1.15 (3H, d.J=7Hz), 1.22 (3H, S.), 1.32 (6H, S.), 2.25 - 2.95 (1H, m.), 3.68 d.J=d.J.=10Hz), 6.82 (2H, b.S.), 9.50 (1H, b.S.) |
| 3-methoxy-α-isopropyl-phenylacetic acid | B | 87.2 | 0.65 (3H, S.J=7Hz), 1.05 (3H, S.J=7Hz), 1.7 - 2.6 (1H, m.), 3.07 (1H, d.J=11Hz), 3.75 (3H, S.), 6.5 - 7.1 (4H, m.), 6.2 (1H, b.S) |
| 4-methyl-α-isopropyl-phenylacetic acid | A | 88.2 | 0.68 (3H, d.J=7Hz), 1.05 (3H, d.J=7Hz), 1.95- 2.50 (1H, m.), 2.29 (3H, S.), 3.05 (1H, d.J=11Hz), 7.11 (centered, 4H, AB type 8), |

-continued

| Method of Hydrolysis | Yields | N.M.R. signals (CHCl$_3$, in ppm) |
|---|---|---|
| | | 9.52 (1H, b.S.) |

*Signal patterns were designated as follows.
S: singlet, d: doublet, m: multiplet, bS: broad Singlet
*Hydrolysis Method A: 50% H$_2$SO$_4$, Method B: Ethyleneglycolaqueous KOH

SYNTHESIS EXAMPLE 4

Diethyl-2-phenyl-2-allyl-malonate

Diethyl-b 2-phenylmalonate (23.60 g, 0.10 mole, prepared from ethylphenylacetate, Org. Synth. Coll, Vol. 2, 288) in 20 ml of dry benzene was added to a stirred solution of sodium hydride (2.38 g, 0.12 mole) in 150 ml of dry benzene at 30° - 40° C, and the mixture was kept at 40° C for 30 minutes. To the white enolate generated was added a solution of allyl bromide (24.2 g, 0.10 mole) in 20 ml of dry benzene at 5° C, thereafter stirring was continued at room temperature for one hour.

The reaction mixture was poured into 200 ml of ice-water, and the organic layer was separated. The aqueous layer was extracted with ether (two 100 ml portions). The organic layers were combined, and washed successively with 5% hydrochloric acid, water and saturated sodium chloride solution, then dried over anhydrous sodium sulfate. The solvent was removed in vacuo, and the residual oil was distilled at reduced pressure to afford 24.27 g (87.90%, b.p. 115° - 120°/0.25 mmHg) of diethyl-2-phenyl-2-allyl-malonate.

SYNTHESIS EXAMPLE 5

Ethyl-α-allylphenylacetate

Diethyl allylphenyl malonate (20.0 g, 0.072 mole) in 250 ml of dry EtOH was heated under reflux with 7.4 g of sodium ethoxide for 5 hours.

Ethanol was removed in vacuo, and the residue was poured to 75 g of ice-water. The mixture was extracted with ether (three 50 ml portions), the ether layer was washed with saturated sodium chloride solution, and dried over anhydrous sulfate. Removal of the solvent, and distillation at reduced pressure afforded 12.54 g (b.p. 60° - 63°/0.13 mmHg, 85.3%) of the phenyl acetate.

SYNTHESIS EXAMPLE 6

α-Allyl-phenyl acetic acid

The above ethylester was hydrolyzed with 10% potassium hydroxide in methanol at room temperature in a usual manner to give the acid (yield 94.6%, m.p. 34° C).

SYNTHESIS EXAMPLE 7

Diethyl-2-phenyl-2-propargyl malonate

In a similar manner to Example 4, the malonate was prepared in 81.7% yield (b.p. 115° - 120°/0.15 mmHg).

SYNTHESIS EXAMPLE 8

α-Propargyl phenyl acetic acid 20.0 g (0.073 mole) of diethyl-2-phenyl-2-propargyl malonate was hydrolyzed in 330 g of 5% methanolic potassium hydroxide at reflux temperature for 2 hours. Methanol was removed in vacuo, and the residue was dissolved in 150 ml of cold water, acidification with concentrated HCl caused a spontaneous decarboxylation to give the monocarboxylic acid, which was collected by ether extraction. (12.4 g, 97.6%, m.p. 90° – 93° C)

SYNTHESIS EXAMPLE 9

Although the compound which bears an isopropenyl group on the α-position such as compounds No. 83, No. 85, No. 125, can be prepared in the usual esterification method using the corresponding acid chloride, the double bond of the isopropenyl group readily isomerized to the α-β position to make the acid or acid chloride into a mixture of double bond positions. A low yield was attained after chromatographic purification.

The following routes seemed to be better than the usual methods.

3'-Phenoxybenzyl-α-isopropenyl-4-methoxyphenylacetate (Compound No. 82)

1. To a solution of isopropylmagnesium bromide, which was prepared from 38.1 g of isopropylbromide and 7.3 g of magnesium in 90 ml of dry ether, was added a solution of 4-methoxyphenylacetic acid (16.6 g) in 100 ml of dry tetrahydrofuran at an ice-bath temperature, thereafter the solution was stirred at room temperature for 2 hours. Dry acetone (7.0 g), diluted with 20 ml of dry toluene, was added to the solution, and it was heated to reflux for 5 hours. The cooled solution was acidified with 15% sulfuric acid, the aqueous phase separated, which was extracted with ether. The combined organic layers were extracted with 10% sodium carbonate solution. The sodium carbonate extract was acidified with concentrated hydrochloric acid and extracted with ether. The ether extract was dried over anhydrous sodium sulfate. Removal of the solvent and recrystallization from ethyl acetate afforded 12.4 g of 4-methoxy-β,β- dimethylatropic acid (55.2%, m.p. 124° – 125° C).

2. To a solution of 4-methoxy-β,β-dimethylatropic acid (5.0 g) and triethylamine (4.5 g) in 50 ml of dimethylformamide, was added 7.0 g of 3-phenoxybenzylbromide gradually at an icebath temperature, and stirred overnight at room temperature. The mixture was poured into cold 10% $H_2SO_4$ and extracted with ether. The ether layer was washed with 10% sodium carbonate solution and dried over anhydrous sodium sulfate. Removal of the solvent gave 4.8 g of crude hydroxyester, which was dehydrated with $P_2O_5$ in benzene at 80° C for 13 hours. Filtration, and removal of the solvent gave crude isopropenyl-ester as a dark oil. Purification with silica-gel chromatography afforded 1.9 g of pure ester. (40.5%, $n_D^{16}$ 1.5798)

SYNTHESIS EXAMPLE 10

Ethyl-2-(cyclohexane-1'-ol-1'-yl)-butyrate

This was prepared from ethyl-2-bromobutyrate (29.3 g), cyclohexanone (14.7 g) and zinc (9.51 g) in benzene (50 ml) and toluene (25 ml) under usual Reformatsky conditions (b.p. 166° – 117°/4 mmHg, yield 16.4 g, 51.0%).

SYNTHESIS EXAMPLE 11

Ethyl-2-(cyclohexene-1-yl)-butyrate

The above hydroxyester (16.4 g) was heated under reflux with phosphorous pentoxide (11 g) in 60 ml of dry benzene for 3 hours. The cooled mixture was poured onto 80 ml of cold water, organic layer was separated and washed with saturated sodium chloride solution. The solvent was removed in vacuo, and the residue was distilled under reduced pressure to afford 11.6 g of pale yellow oil (76.5%, b.p. 88° – 92°/4 mmHg)

SYNTHESIS EXAMPLE 12

Ethyl-2,3-diethyl -3-hydroxy-pentanoate

In similar manners described in Example 10, this was prepared from 3-pentanone and ethyl-2-bromobutyrate. (yield 52.8%, b.p. 113° – 121°/20 mmHg)

SYNTHESIS EXAMPLE 13

The hydroxyester obtained in Example 12, was dehydrated with phosphorous pentoxide in benzene in a manner described above. (yield 68.2%, b.p. 95° – 98°/22 mmHg)

The compounds of the type designated as Compound Nos. 18, 21, 245, 246 and 248 were prepared from the corresponding carboxylic acid or an acid chloride derived therefrom which is obtained by hydrolyzing the ethyl ester prepared in the similar manner as described in Synthesis Examples 10 – 13. The hydrolysis can be effected by the conventional procedure using sodium hydroxide or potassium hydroxide in methanol at room temperature. The carboxylic acid thus obtained was found to contain a small amount of isomers with respect to double bonds (up to about 10%), but the crude carboxylic acid was subjected to esterification without isolating the impurities (isomers) and the product was purified by silica gel chromatography in the final step.

The substituted ester compounds represented by the formula (I) exhibit an excellent pesticidal activity and are expected to have a repelling activity against mites as well as a synergistic activity with other biologically active agents, and can be employed in a wide variety of applications at low cost as pesticidal compositions for use in agriculture and horticulture, forests, sanitary fields as well as in a stockroom of cereals and a composition for controlling mites.

In practical use of these compounds, an appropriate amount of one or more solvents, fillers, diluents, active agents, dispersing agents, surface active agents, spreaders, pressure-imparting agents, emulsifying agents and attractants can be incorporated into the ester compounds of this invention to form an emulsifiable concentrate, a wettable powder, a dust, granules, fine graines, a coating agent, a powder, an oil preparation, an aerosol, a mosquito coil, a smoking agent, a fumigating agent, a mosquito insence agent for electrical vaporization, and the like.

The effect of the pesticidal compositions of this invention is further illustrated by the following Experiments.

EXPERIMENTAL EXAMPLE 1

An emulsifiable concentrate was prepared by blending each of the compounds (1) to (312) of the present invention, xylol and Sorpol SM-200 (trade name; manufactured by Toho Chemical Co., Ltd.) in a proportion of 25%, 50% and 25% (by weight), respectively. 20 to 25 day-old rice plants after seeding were grown in pots and sprayed with each 300-fold dilute solution of the emulsifiable concentrates thus prepared and a 300-fold dilute solution of carbaryl 30% wettable powder diluted with water as a control commercial agent in an amount of 10 ml/pot in each case and then the pots were covered by a cylindrical metal net. 15 smaller brown planthoppers (*Laodelphax striatellus* Fallen) per group were released in each of the pots treated with the carbaryl wettable powder, and compound (1) to (21) and (102) to (110), while 15 green rice leafhoppers (Nephotettix bipuntatus cincticeps Uhler) per group were released in each of the pots treated with the carbaryl wettable powder and compounds (22) to (101) and (111) to (312). Observation on survival one day after the treatment revealed that each of the compounds of this invention exhibits more than a 90% killing effect as in the case of carbaryl.

EXPERIMENTAL EXAMPLE 2

Of the emulsifiable concentrates prepared in Experimental Example 1, each of those prepared from the compounds of Table 1 below was diluted with water to each of test concentrations and a 200 ml portion thereof was added to a 300 ml volume beaker. 30 larvae of mosquito per group were released in each of the beaker and allowed to stand for 1 day. Survival was observed and a $LC_{50}$ (50% lethal concentration) was determined by calculating the percent killing in each case. The results obtained are also shown in Table 1. As a control, lindane emulsifiable concentrate was used.

Table 1

| Insecticidal Activity on Larvae of Mosquito (Culex pipiens) | | | |
|---|---|---|---|
| Test Emulsifiable Concentrate | $LC_{50}$ (ppm) | Test Emulsifiable Concentrate | $LC_{50}$ (ppm) |
| Compound (1) | 0.0015 | Compound (2) | 0.0034 |
| " (10) | 0.0030 | " (14) | 0.0026 |
| " (16) | 0.0014 | " (102) | 0.0095 |
| " (103) | 0.0092 | " (104) | 0.0120 |
| " (105) | 0.0105 | " (110) | 0.0125 |
| " (111) | 0.0025 | " (112) | 0.0046 |
| " (113) | 0.0053 | " (115) | 0.0050 |
| " (119) | 0.0044 | " (120) | 0.0040 |
| " (121) | 0.0037 | " (125) | 0.0032 |
| " (126) | 0.0056 | " (128) | 0.0047 |
| " (145) | 0.0039 | " (165) | 0.0012 |
| " (167) | 0.0043 | " (177) | 0.0074 |
| " (180) | 0.0072 | " (181) | 0.0820 |
| " (183) | 0.0885 | " (184) | 0.0078 |
| " (204) | 0.0075 | " (206) | 0.0032 |
| " (210) | 0.0035 | " (212) | 0.0037 |
| " (214) | 0.0127 | " (215) | 0.0132 |
| " (226) | 0.0135 | " (227) | 0.0019 |
| " (231) | 0.0014 | " (298) | 0.0097 |
| " (302) | 0.028 | Lindane | 0.22 |

EXPERIMENTAL EXAMPLE 3

A 2000-fold dilute solution of each of the emulsifiable concentrates prepared in Experimental Example 1 from the compounds of Table 2 below was sprayed on a 12 day-oil seedling of mottled kidney beans after seeding grown in a pot in an amount of 10 ml/pot. The seedling thus treated was cut off and put in a wide opening bottle. In the same manner, an untreated mottled kidney been seeding in the same stage was cut off and put in another wide opening bottle. Another fresh seedling was fixed with pins bridging the former treated seedling and the latter untreated seedling. A mottled kidney bean leaf on which a number of spider mites (Tetranychus telarius) were parasitic was placed on the middle of the bridging seedling and allowed to stand for 2 days. Activity on repellency was assessed by investigating the numbers of mites swarming on the treated seedling and the untreated seedling. The assessment standards are as follows:

| – | The ratio of the number of mites on the untreated seedling to that on the treated seedling | 1 : 1 |
|---|---|---|
| + | " | up to 4 : 1 |
| ++ | " | greater than 4 : 1 |

The results obtained was shown in Table 2 below.

Table 2

| Repellent Activity on Spider Mites | | | |
|---|---|---|---|
| Test Emulsifiable Concentrate | Repellency | Test Emulsifiable Concentrate | Repellency |
| Compound (1) | ++ | Compound (3) | + |
| " (4) | ++ | " (10) | ++ |
| " (18) | + | " (23) | + |
| " (29) | ++ | " (35) | + |
| " (45) | ++ | " (65) | + |
| " (73) | + | " (82) | ++ |
| " (92) | ++ | " (98) | ++ |
| " (116) | ++ | " (117) | ++ |
| " (118) | ++ | " (121) | ++ |
| " (124) | + | " (127) | ++ |
| " (130) | + | " (165) | ++ |
| " (168) | ++ | " (175) | ++ |
| " (176) | ++ | " (177) | ++ |
| " (178) | ++ | " (200) | ++ |
| " (204) | ++ | " (206) | ++ |
| " (210) | ++ | " (216) | ++ |
| " (217) | ++ | " (218) | ++ |
| " (219) | ++ | " (220) | ++ |
| " (221) | ++ | " (227) | ++ |
| " (234) | ++ | " (235) | ++ |
| " (301) | ++ | | |

EXPERIMENTAL EXAMPLE 4

A 0.2% oil preparation was prepared from each of the compounds (1), (2), (8), (14), (22), (25), (26), (27), (51), (62), (73), (82), (86), (88) to (90), (92), (94), (96), (111), (119), (121), (165), (175), (180), (184), (185), (195), (200), (201), and (208) and allethrin as a control using deodorized kerosene. About 50 adult mosquitoes (Culex pipiens) were released in a (70 Cm)$^3$ volume glass box and sprayed with each of the oil preparations obtained above in an amount of 0.7 ml under a pressure of 1.5 Kg/cm$^2$. It was found that more than 80% of mosquitoes was knocked down by both allethrin and the compounds of this invention.

EXPERIMENTAL EXAMPLE 5

20 oriental house flies per group were released in a (70 cm)$^3$ volume glass box and sprayed with each of the oil preparations prepared in Experimental Example 4 from the compounds of Table 3 below and allethrin in an amount of 0.7 ml under a pressure of 1.5 Kg/cm$^2$. The test was repeated several times and the knock down of the flies was observed to determine the $KT_{50}$ (50% knock-down time). The results obtained are shown in Table 3.

Table 3

| Activity on Knock-Down Against Oriental House Flies | | | |
|---|---|---|---|
| Test Oil Preparation | $KT_{50}$ (sec.) | Test Oil Preparation | $KT_{50}$ (sec.) |
| Compound (1) | 167 | Compound (8) | 128 |
| " (22) | 136 | " (51) | 104 |
| " (62) | 154 | " (63) | 140 |
| " (82) | 132 | " (88) | 147 |
| " (89) | 155 | " (96) | 92 |
| " (111) | 138 | " (119) | 132 |
| " (121) | 130 | " (165) | 145 |
| " (175) | 152 | " (180) | 157 |
| " (184) | 142 | " (185) | 137 |
| " (195) | 140 | " (200) | 114 |
| " (201) | 105 | " (208) | 150 |
| Allethrin | 186 | | |

EXPERIMENTAL EXAMPLE 6

To each of the compounds (22), (51), (62), (63), (82), (86), (125), (150), (160), (176), (177), (178), (184), (185), (191), (195), (200), (201), (204), (208), (210), (212) and (226) was added piperonyl butoxide in an amount of 5 times that of the active ingredient, respectively, to prepare an acetone solution having a given concentration. Each of the thus prepared acetone solutions was applied onto the thoracic dosal plate of the oriental house flies using a microsyringe to observe a synergestic effect on insecticidal activity by piperonyl butoxide. The potentiation magnification of insecticidal activity by the addition of piperonyl butoxide is shown in Table 4.

Table 4

Potentiation Effect on Insecticidal Activity by the Addition of Piperonyl Butoxide

| Test Compound | | Potentiation Magnification | Test Compound | | Potentiation Magnification |
|---|---|---|---|---|---|
| Compound | (22) | 5.0 | Compound | (51) | 7.2 |
| " | (62) | 5.3 | " | (63) | 4.8 |
| " | (82) | 6.7 | " | (86) | 4.5 |
| " | (119) | 5.5 | " | (125) | 6.0 |
| " | (150) | 4.2 | " | (160) | 7.2 |
| " | (176) | 5.2 | " | (177) | 5.8 |
| " | (178) | 5.4 | " | (184) | 5.6 |
| " | (185) | 5.0 | " | (191) | 4.3 |
| " | (195) | 5.7 | " | (200) | 7.5 |
| " | (201) | 7.0 | " | (204) | 4.7 |
| " | (206) | 5.1 | " | (208) | 5.2 |
| " | (210) | 4.8 | " | (212) | 5.0 |
| " | (226) | 4.5 | | | |

As is apparent from the above Experimental Examples, the compounds of this invention exhibit an excellent biological activity on various noxious insects and mites and also are of low toxicity.

The oral toxicity to mice for representative compounds is shown in the Table below.

Table

| Test Compound | | $LD_{50}$ (mg/Kg) | Test Compound | | $LD_{50}$ (mg/Kg) |
|---|---|---|---|---|---|
| Compound | (1) | >1000 | Compound | (2) | >1000 |
| " | (8) | 750 | " | (22) | 900 |
| " | (62) | >1000 | " | (63) | >1000 |
| " | (80) | >1000 | " | (82) | >1000 |
| " | (108) | >1000 | " | (119) | >1000 |
| " | (125) | >1000 | " | (129) | >1000 |
| " | (130) | >1000 | " | (145) | >1000 |
| " | (150) | >1000 | " | (176) | >1000 |
| " | (184) | 940 | " | (206) | >1000 |

The compositions according to the present invention are very useful for controlling unsanitary insects such as mosquitoos, flies and cockroaches, grain insects such as rice weevil (*Calandra oryzae*) and mites as well as agricultural noxious insects such as plant-hoppers, green rice leafhopper (*Nephotettix bipuntatus cinticeps* Uhler), cabbage army worms (*Barathra brassicae* Linne), diamond-back moths (*Plutella maculipennis* Curtis), noctuidae, cabbage worm (*Pieris rapae* Linne), rice stem borers (*Chilo suppressalis* Walker), aphids, tortrixes, leaf-miners and the like.

They are also superior whenever they may be freely used for harvested crops, horticultural application, cultures in green house, and packaging materials for foodstuffs.

In preparing the compositions according to the present invention, it is possible to obtain more excellent controlling effects by employing a combination of two or more compounds of this invention, and further, it is possible to obtain various compositions which are useful for a wide variety of applications by combining one or more compounds of this invention with other pesticidal compounds, for example, organochloric compounds such as DDT, BHC, Methoxychlor and the like; organic phosphorus compounds such as Sumithion (trade name of Sumitomo Chemical Company Limited), DDVP, diazinon, phenthion, Cyanox (trade name of Sumitomo Chemical Company Limited) and the like; carbamates such as 1-naphthyl-N-methylcarbamate, 3,4-dimethylphenyl N-methylcarbamate, 3,5-dimethylphenyl N-methylcarbamate and the like; cyclopropanecarboxylic acid esters such pyrethrin, allethrin, Neopynamin (trade name of Sumitomo Chemical Company Limited), Chrysron (trade name of Sumitomo Chemical Company Limited), 3-phenoxybenzyl chrysanthemate, 5-propargylfurfuryl chrysanthemate and their geometrical or optical isomers and the like, as well as piperonyl butoxide, sulfoxide, safroxane, isobornyl thiocyano acetate (I.B.T.A.) and octachloro dipropyl ester (S-421) which potentiate the effect of the esters synergistically; terephthalic acid, isophthalic acid and BHT which are generally used in fumigating preparations; phenol derivatives used as a stabilizer; bisphenol derivatives; arylamines such as phenyl-α-naphthylamine, phenyl-β-naphthylamine, a condensate of phenetidin and acetone and the like; other insecticidal agents or miticidal agnets cush as Padan, Galecron, antimicrobial agents, nematocidal agents, herbicidal agents, fertilizers and other agricultural agents. These compositions are expected to be useful for saving man power for application of these agricultural agents and for obtaining synergistic activities between the active ingredients of the composition.

The preparation of compositions and the effect of compounds of this invention are further illustrated by the following Formulations and Examples, but they are not to be construed as limiting the scope of this invention. The parts used in formulations are by weight unless otherwise indicated.

FORMULATION 1

To 20 parts of each of Compound Nos. 1 to 110 and 302 to 312 of this invention, there were added 10 parts of Sumithion (as described previously), 10 parts of Sorpol SM-200 (as described previously), 60 parts of xylol, and the mixture was dissolved by thoroughly stirring and mixing to obtain an emulsifiable concentrate in each case.

FORMULATION 2

To 10 parts of each of Compound Nos. 111 to 192 of this invention, there were added 10 parts of Cyanox (as described previously), 10 parts of Sorpol SM-200 (as described previously) and 70 parts of xylol, and the mixture was dissolved by thoroughly stirring and mixing to obtain an emulsifiable concentrate in each case.

FORMULATION 3

To 15 parts of each of Compound Nos. 193 to 232 of this invention, there were added 30 parts of piperonyl butoxide, 15 parts of Sorpol SM-200 (as described previously) and 40 parts of xylol, and the mixture was dissolved by thoroughly stirring and mixing to obtain an emulsifiable concentrate in each case.

FORMULATION 4

To 15 parts of each of Compound Nos. 233 to 300 of this invention, there were added 20 parts of a 25% pyrethrin extract, 20 parts of piperonyl butoxide, 15 parts of Sorpol SM-200 (as described previously) and 30 parts of xylol, and the mixture was dissolved by thoroughly stirring and mixing to obtain an emulsifiable concentrate in each case.

FORMULATION 5

0.5 parts of each of Compound Nos. 1, 10, 102, 103, 108, 111 to 115 and 302 to 312 was dissolved in kerosene in an amount sufficient to make 100 parts thereby obtaining an oil preparation in each case.

FORMULATION 6

To 0.2 parts of each of Compound Nos. 116 to 192 of this invention, there were added 0.1 parts of allethrin α-trans chrysanthemate and 1.5 parts of safroxane, and the mixture was dissolved in kerosene to prepare 100 parts of an oil preparation in each case.

FORMULATION 7

To 0.2 parts of each of Compound Nos. 193 to 300 of this invention, there were added 0.1 parts of Neopynamine and 1.5 parts of S-421, and the mixture was dissolved in kerosene to prepare 100 parts of an oil preparation in each case.

FORMULATION 8

To 10 parts of each of Compound Nos. 1 to 110 and 301 to 312 of this invention, there were added 10 parts of 1-naphthyl-N-methyl-carbamate and 5 parts of Sorpol SM-200 (as described previously) followed by mixing. 75 parts of 300-mesh talc was then added to the mixture and the resulting blend was thoroughly stirred in a triturator to obtain an wettable powder in each case.

FORMULATION 9

The active pesticidal ingredients having a composition shown in Table below were dissolved in 20 ml of methanol and the resulting solution was mixed with 100 g of a carrier for a mosquito coil (a mixture of tabu powder, pyrethrum marc and wood powder in a proportion of 3:5:1, respectively), followed by blending uniformly. After methanol was evaporated, 150 ml of water was added to the blend, and the mixture was thoroughly kneaded, molded and dried to prepare a mosquito coil in each case.

| No. | Mosquito Coil Formulations Composition | |
|---|---|---|
| 1. | Compound No. 1 | 0.3 g |
|  | Allethrin | 0.3 g |
| 2. | Compound No. 8 | 0.3 g |
|  | Allethrin | 0.3 g |
| 3. | Compound No. 22 | 0.3 g |
|  | Allethrin | 0.2 g |
|  | BHT | 0.3 g |
| 4. | Compound No. 37 | 0.3 g |
|  | Allethrin | 0.3 g |
| 5. | Compound No. 51 | 0.3 g |
|  | Allethrin α-trans chrysanthemate | 0.1 g |
|  | BHT | 0.4 g |
| 6. | Compound No. 62 | 0.2 g |
|  | 5-Propargylfurfuryl chrysanthemate | 0.2 g |
|  | BHT | 0.8 g |
| 7. | Compound No. 82 | 0.3 g |
|  | 5-Propargyl-2-methyl-3-furylmethyl chrysanthemate | 0.1 g |
|  | BHT | 0.4 g |
| 8. | Compound No. 146 | 0.3 g |
|  | Allethrin d-cis,trans chrysanthemate | 0.1 g |
|  | BHT | 0.5 g |
| 9. | Compound No. 169 | 0.3 g |
|  | Allethrin | 0.2 g |
|  | BHT | 0.5 g |
| 10. | Compound No. 184 | 0.3 g |
|  | Allethrin | 0.3 g |
|  | BHT | 0.3 g |

FORMULATION 10

The active pesticidal ingredients having the composition shown in the Table below were dissolved in a mixed solvent comprising xylol and refined kerosene (1:1 by volume) to prepare 15 parts of solution and the solution was filled in an aerosol dispensing container. After a valve was mounted to the container, the aerosol dispenser was pressurized by charging 85 parts of a propellant (for example, freon, vinyl chloride monomer, liquified petroleum gas, etc.) to obtain aerosol preparations.

| No. | Aerosol Formulations Composition | |
|---|---|---|
| 1. | Compound No. 22 | 0.3 (parts) |
|  | 3-Phenoxybenzyl-d-cis,trans chrysanthemate | 0.1 |
| 2. | Compound No. 22 | 0.2 |
|  | Neopynamin | 0.2 |
|  | I.B.T.A. | 1 |
| 3. | Compound No. 62 | 0.2 |
|  | Allethrin d-trans chrysanthemate | 0.2 |
|  | Safroxane | 2 |
| 4. | Compound No. 62 | 0.3 |
|  | DDVP | 0.3 |
| 5. | Compound No. 82 | 0.2 |
|  | Sumiothin | 0.3 |
|  | Neopynamin | 0.2 |
| 6. | Compound No. 82 | 0.4 |
|  | Piperonyl butoxide | 2.0 |
| 7. | Compound No. 88 | 0.2 |
|  | Neopynamin | 0.2 |
|  | Chrysron | 0.1 |
| 8. | Compound No. 89 | 0.3 |
|  | Allethrin d-trans chrysanthemate | 0.2 |
| 9. | Compound No. 96 | 0.2 (parts) |
|  | Allethrin d-cis, trans chrysanthemate | 0.2 |
|  | Safroxane | 2 |
| 10. | Compound No. 102 | 0.4 |
|  | Neopynamin | 0.1 |
|  | Piperonyl butoxide | 1.5 |
| 11. | Compound No. 103 | 0.4 |
|  | Allethrin | 0.1 |
|  | S-421 | 1.5 |
| 12. | Compound No. 108 | 0.4 |
|  | 25% Pyrethrin extract | 0.5 |
|  | Piperonyl butoxide | 1.0 |
| 13. | Compound No. 125 | 0.4 |
|  | I.B.T.A. | 2 |

FORMULATION 11

The active pesticidal ingredients having the composition shown in the Table below were dissolved in an appropriate amount of chloroform, and the solution was adsorbed uniformly on the surface of asbestos having a size of 2.5 cm × 1.5 cm and a thickness of 0.3 mm. Another piece of asbestos having the same size and thickness was then placed on the treated surface of the above asbestos to prepare a fibrous fumigation pesticidal composition (mat) for heating on a hot plate. As a fibrous carrier, those having the same effect as that of asbestos such as a pulp board, etc. may also be used in place of asbestos.

| No. | Formulation of Mat for Heating on Hot Plate Composition | | |
|---|---|---|---|
| 1. | Compound No. 51 | 0.05 | g |
|  | Allethrin | 0.02 | g |
|  | Piperonyl butoxide | 0.07 | g |
| 2. | Compound No. 63 | 0.07 | g |
|  | Allethrin d-trans chrysanthemate | 0.01 | g |
|  | Piperonyl butoxide | 0.1 | g |
| 3. | Compound No. 80 | 0.5 | g |
|  | 5-Propargyl furylmethyl chrysanthemate | 0.02 | g |
|  | Piperonyl butoxide | 0.15 | g |
|  | BHT | 0.1 | g |
| 4. | Compound No. 82 | 0.04 | g |
|  | Allethrin | 0.04 | g |
|  | Piperonyl butoxide | 0.08 | g |
|  | BHT | 0.1 | g |
| 5. | Compound No. 88 | 0.05 | g |
|  | 5-Propargyl-2-methyl-3-furyl-methyl chrysanthemate | 0.02 | g |
|  | Piperonyl butoxide | 0.15 | g |
| 6. | Compound No. 103 | 0.05 | g |
|  | Allethrin | 0.02 | g |
|  | Piperonyl butoxide | 0.15 | g |
| 7. | Compound No. 107 | 0.05 | g |
|  | 5-Phenoxybenzyl chrysanthemate | 0.03 | g |
| 8. | Compound No. 125 | 0.05 | g |
|  | Allethrin | 0.01 | g |

FORMULATION 12

To 1 part of each of Compound Nos. 22, 51, 62, 63, 83, 86, 94, 103, 108 and 125 of this invention was added 5 parts of piperonyl butoxide and the mixture was dissolved in 20 parts of acetone. After 94 parts of 300-mesh diatomaceous earth was added, the resulting blend was thoroughly stirred and mixed in a triturator, and acetone was removed by evaporation to obtain a powder in each case.

EXAMPLE 1

10 third inster larvae of tobacco cutworm (*Spodoptera lituna* Fabricius) were placed in a glass tray having a high side-wall and a diameter of 14 cm, and 1 ml of a 200-fold dilute solution of each of the emulsifiable concentrates obtained in Formulations 1 and 3 diluted with water was sprayed on the larvae with a sprayer and the larvae thus treated were then transferred into a glass tray containing feeds followed by allowing to stand. Two days after the treatment, greater than 80% of the larvae was found to be killed in each case.

EXAMPLE 2

In an area of a radish field in the 5–6 leaf stage, a number of green peach aphids (*Myzus persicae* Sulza) was atomized with a 200-fold dilute solution of each of the emulsifiable concentrates obtained in Formulations 1, 2 and 4 diluted with water at a level of 424 l/acre. Investigation two days after treatment revealed that the density of aphids is reduced to less than 1/10 the density before treatment in each case.

EXAMPLE 3

A piece of plywood board (15 cm × 15 cm) was applied with a 200-fold dilute solution of each of the emulsifiable concentrates obtained in Formulations 1 and 2 diluted with water in an amount of 50 ml/m² followed by drying. Adult German cockroaches (*Blatuella germanica* Linne) were then brought into contact with the plywood board thus treated for 1 hour, and it was found that more than 80% cockroaches was killed three days after contact with the board.

EXAMPLE 4

A field of egg-plant (ripe plant) having a number of larvae of potato lady beetle (*Epilachna sparsa orientalis* Dieke) was atomized with a 200-fold dilute solution of each of the emulsifiable concentrates obtained in Formulation 1 in an amount of 424 l/acre. Investigation on knock-down thirty minutes after the treatment revealed that 90% larvae fell to the ground. A further investigation on larvae density 24 hours after the treatment revealed that almost 100% larvae had been controlled as compared with the larvae density before the treatment.

EXAMPLE 5

Forty-five day-old rice plants after seeding were grown in Wagner pots (1/50000) and sprayed with a 400-fold dilute solution of each of the wettable powders obtained in Formulation 8 in an amount of 10 ml/pot. The pots were then covered with a cylindrical metal net and about 20 larvae of leaf hopper (*Cicadula sexnotata*) were released therein. In each case, more than 80% larvae were found to be killed one day after the release.

EXAMPLE 6

Each of the dusts obtained in Formulation 12 was placed uniformly at the bottom of glass trays having a diameter of 14 cm and a high side-wall in an amount of 2 g/m² and butter was applied to the glass wall except for about 1 cm portion of the bottom. 10 adult German cockroaches per group were then released in the glass trays and, 30 minutes after contact, the larvae were transferred to a fresh glass container. In each case, more than 80% of the larvae was found to be killed three days after the treatment.

EXAMPLE 7

Each of the oil preparations obtained in Formulation 5 was atomized using Campel's turn table apparatus [Soap and Sanitary Chemicals, Vol. 14, No. 6, 119(1938)] in an amount of 5 ml. 20 seconds after atomizing, the shutter was opened and 100 adult oriental house flies (*Musca domestica vicina* Maquant) per group were exposed to the falling atomized fumes for a period of 10 minutes. The flies thus treated were then fed and followed by allowing to stand. More than 80% of the flies were found to be killed in each case.

EXAMPLE 8

Each of the oil preparations obtained in Formulation 7 was sprayed in a (70 cm)³ volume glass box containing about 50 adult oriental house flies in an amount of 0.7 ml under a pressure of 1.5 Kg/cm² and it was found that more than 80% of the flies was knocked down in 10 minutes after the treatment in each case.

EXAMPLE 9

About 50 adult mosquitoes (*Culex pipiens*) per group were released in a (70 cm)³ volume glass box and sprayed with each of the oil preparations obtained in Formulation 6 in an amount of 0.7 ml under a pressure of 1.5 Kg/cm². It was found that more than 80% of the flies was knocked down in 10 minutes after the treatment in each case.

EXAMPLE 10

A nylon net of about 15 mesh was sprayed on the lower part of a glass cylinder having a diameter of 20 cm and a height of 20 cm and butter was applied on the upper part of the glass cylinder in a width of about 3 cm. Then 20 adult German cockroaches were released therein. The glass cylinder containing the cockroaches was plied on another glass cylinder of the same size, and further another glass cylinder having a diameter of 20 cm and a height of 40 cm was placed thereon. 0.5 ml of each of the oil preparations obtained in Formulation 7 was sprayed from the upper cylinder using a glass atomizer under a pressure of 0.75 Kg/cm² and then sealed followed by allowing to stand. It was found that more than 90% of the cockroaches were knocked down in 30 minutes after the treatment and that more than 90% of the cockroaches were killed 3 days after the treatment.

EXAMPLE 11

Insecticidal activity of each of the aerosols obtained in Formulation 10 on oriental house flies was tested by an aerosol test method using a Peet grady chamber [a method reported in Soap and Chemical Specialities Bluebook (1965)]. The test results revealed that knockdown of more than 80% of the flies was observed in 15 minutes after the treatment and more than 70% of the flies was killed one day after the treatment in each case.

EXAMPLE 12

About 50 adult mosquitoes (*Culex pipiens*) were released in a (70 cm)³ volume glass box and a mosquito coil both ends thereof having been ignited, was placed in the center of the box bottom. After 20 minutes more than 80% of the flies was found to be knocked down.

EXAMPLE 13

About 50 adult mosquitoes (*Culex pipiens*) were released in a (70cm)³ volume glass box and a heating mat obtained in Formulation 11 fixed on an electrothermic plate was placed in the glass box followed by heating to smoke. Within 20 minutes, more than 90% of the mosquitoes was found to be knocked down.

While the invention has been described in detail and with reference to specific embodiments thereof, it will be apparent to one skilled in the art that various changes and modifications can be made therein without departing from the spirit and scope thereof.

What is claimed is:

1. A phenylacetate compound of the formula:

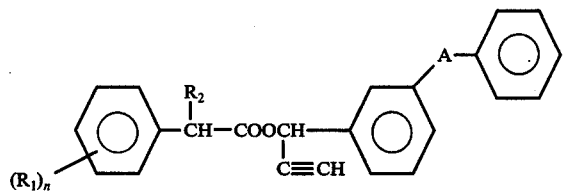

wherein $R_1$, in which the $R_1$'s may be the same or different, is halogen or $C_1$-$C_4$ alkyl,; n is 1 or 2; $R_2$ is $C_1$-$C_4$ alkyl; and A is oxygen or —$CH_2$—.

2. A compound of the formula;

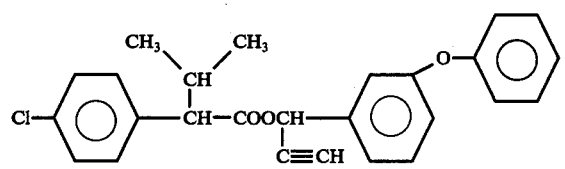

according to claim 1.

3. A compound of the formula;

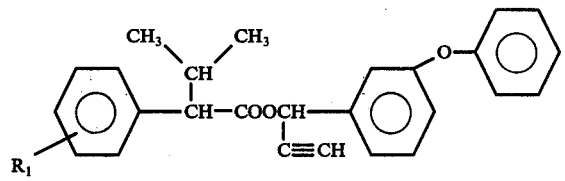

wherein $R_1$ is halogen.

4. A pesticidal composition consisting essentially of a pesticidally effective amount of a phenylacetate compound of claim 1 and an inert carrier.

5. A method for knocking down and killing injurious insects, ticks and mites by contacting a pesticidal composition of claim 4 to their habitats.

* * * * *